(12) United States Patent
Al Ahmad

(10) Patent No.: US 11,619,589 B2
(45) Date of Patent: Apr. 4, 2023

(54) METHOD AND SYSTEM FOR DETECTION, QUANTIFICATION AND/OR IDENTIFICATION OF AN ANALYTE IN A SPECIMEN BASED ON ELECTRICAL AND/OR OPTICAL RESPONSE TO AN ELECTRIC FIELD

(71) Applicant: United Arab Emirates University, Al Ain (AE)

(72) Inventor: Mahmoud F. Y. Al Ahmad, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

(21) Appl. No.: 17/514,078

(22) Filed: Oct. 29, 2021

(65) Prior Publication Data

US 2022/0120692 A1     Apr. 21, 2022

Related U.S. Application Data

(63) Continuation-in-part of application No. 17/379,496, filed on Jul. 19, 2021.

(Continued)

(51) Int. Cl.
*G01N 21/66* (2006.01)
*G01N 33/569* (2006.01)

(52) U.S. Cl.
CPC ....... *G01N 21/66* (2013.01); *G01N 33/56983* (2013.01); *G01N 2800/26* (2013.01)

(58) Field of Classification Search
None
See application file for complete search history.

(56) References Cited

U.S. PATENT DOCUMENTS 11,029,282 B2 * 6/2021 Vilkov ............... H01J 49/0031
2014/0255916 A1   9/2014 Sigal
(Continued)

FOREIGN PATENT DOCUMENTS

| WO | 2011060184 A1 | 5/2011 |
| WO | 2015116083 A1 | 8/2015 |
| WO | 2021081476 A1 | 4/2021 |

OTHER PUBLICATIONS

Mran et al. 2021; Micromachines. 2021; (12) 2: 174.*
(Continued)

*Primary Examiner* — Shanon A. Foley
(74) *Attorney, Agent, or Firm* — Boyle Fredrickson, S.C.

(57) ABSTRACT

A method and a system of detecting, identifying and quantifying an analyte, for example coronavirus, in a specimen comprising, comprising: apportioning the suspended specimen into one or more test samples; optionally adding a reagent to the test samples; and applying an electric field with a first magnitude and with a second magnitude over the test samples for a selected period of time. The second magnitude should be higher than the first magnitude. The method and system further comprises: measuring electrical properties of said one or more test samples in response to said applied electric field for said first magnitude and for said second magnitude over said period of time; identifying characteristics of said electrical properties responses; and determining the presence, the identification and/or the quantity of coronavirus based on the characteristics of said electrical properties responses to said first magnitude and to said second magnitude of the applied electric field.

11 Claims, 26 Drawing Sheets
(25 of 26 Drawing Sheet(s) Filed in Color)

Related U.S. Application Data

(60) Provisional application No. 63/107,191, filed on Oct. 29, 2020, provisional application No. 63/054,022, filed on Jul. 20, 2020.

(56) References Cited

U.S. PATENT DOCUMENTS

| | | | |
|---|---|---|---|
| 2015/0203925 | A1 | 7/2015 | Israel et al. |
| 2017/0234801 | A1 | 8/2017 | Unlu et al. |
| 2017/0362668 | A1 | 12/2017 | Glezer et al. |
| 2021/0123883 | A1 | 4/2021 | Tabib-Azar |
| 2022/0120692 | A1* | 4/2022 | Al Ahmad ....... G01N 33/56983 |

OTHER PUBLICATIONS

International Search Report for Application No. PCT/IB2021/056520 filed Jul. 19, 2021, dated Sep. 23, 2021, 6 pages.

Written Opinion for Application No. PCT/IB2021/056520 filed Jul. 19, 2021, dated Sep. 23, 2021, 8 pages.

Bakr Ahmed Taha et al., An Analysis Review of Detection Coronavirus Disease 2019 (COVID-19) Based on Biosensor Application, Sensors, Nov. 26, 2021, 29 pages.

Xiuyuan Ou et al., Characterization of spike glycoprotein of SARS-CoV-2 on virus entry and its immune cross-reactivity with SARS-CoV, Nature Communications, 2020, 12 pages.

Mahmoud Al Ahmad et al., Development of an Optical Assay to Detect SARS-CoV-2 Spike Protein Bindng Interactions wth ACE2 and Disruption of these Interactions Using Electric Current, Nov. 28, 2020, 21 pages.

Aaron T. Fafarman et al., Quantitative, directional measurement of electric field heterogeneity in the active site of ketosteroid isomerase, PNAS, Feb. 7, 2012, 10 pages, vol. 109, Issue No. 6.

Marc C. Johnson et al., Optimized Pseudotyping Conditions for the SARS-COV-2 Spike Glycoprotein, Journal of Virology, Nov. 2020, 10 pages, vol. 94, Issue 21.

Jun Lan et al., Structure of the SARS-CoV-2 spike receptor-binding domain bound to the ACE2 receptor, Nature, May 14, 2020, 16 pages, vol. 581.

\* cited by examiner

Spike

ACE2

Spike + ACE2

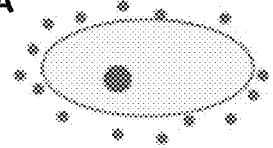
FIG. 4A
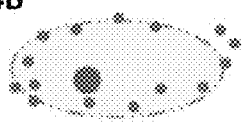
FIG. 4B
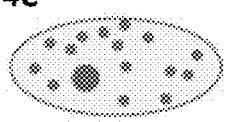
FIG. 4C
FIG. 5A
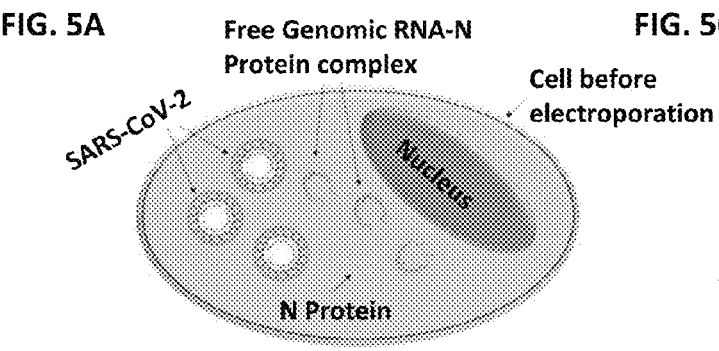
FIG. 5B
FIG. 5C
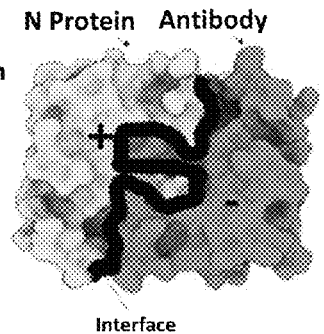
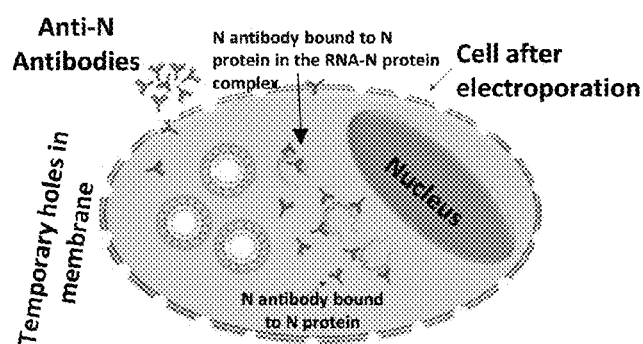
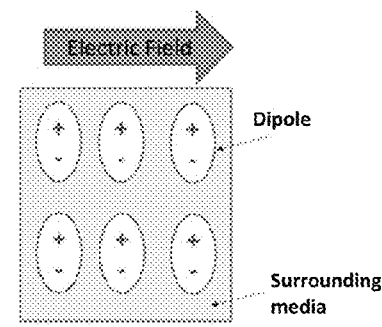
FIG. 5D

FIG. 24A  FIG. 24B

METHOD AND SYSTEM FOR DETECTION, QUANTIFICATION AND/OR IDENTIFICATION OF AN ANALYTE IN A SPECIMEN BASED ON ELECTRICAL AND/OR OPTICAL RESPONSE TO AN ELECTRIC FIELD

CROSS-REFERENCE TO RELATED APPLICATIONS

This application is a non-provisional application claiming priority to U.S. Provisional Application No. 63/107,191 and filed on Oct. 29, 2020, the entire contents of which are incorporated herein by reference. This application is also a continuation-in-part and claims priority to U.S. Non-Provisional application Ser. No. 17/379,496 filed on Jul. 19, 2021, which claims priority to U.S. Provisional Application No. 63/054,022 filed on Jul. 20, 2020, the entire contents of both are incorporated herein by reference.

FIELD OF THE INVENTION

The present disclosure relates in general to a method and system for analyte detection and monitoring, and more specifically to a method and system for detection, quantification and/or identification of an analyte such as a coronavirus, using analyte and reagent interactions detection and monitoring based on electrical and/or optical response to an electric field. More specific embodiments of the present disclosure relate in general to a method and system for virus detection and monitoring, and more specifically to a method and system for detection, quantification and/or identification of a coronavirus, using virus and protein-antibody interactions detection and monitoring based on electrical and/or optical response to an electric field.

BACKGROUND

In late December 2019, patients with an atypical pneumonia due to a novel coronavirus were reported in Wuhan, China. Since then, the novel coronavirus disease 2019 (COVID-19) has become a pandemic that has spread worldwide to virtually every country. This pandemic has caused massive social and economic disruptions in nearly every country and therefore global research and development efforts are being geared towards development of vaccines and therapeutics for the prevention and treatment of COVID-19, in order to normalize the situation.

Unfortunately, the complete clinical picture of COVID-19 is not yet fully known and most likely depends upon a number of factors, including virus characteristics. As of Jul. 7, 2020, more than 11,645,109 cases of COVID-19 infection had been confirmed worldwide with 538,780 deaths, revealing a case fatality rate (CFR) of 4.6%. Successful detection of SARS coronavirus 2 (SARS-CoV-2) plays an important role in stopping the spread.

The novel severe acute respiratory syndrome coronavirus 2 (SARS-CoV-2) that causes COVID-19 enters the susceptible cells primarily via endocytosis using its spike (S) protein (3-5). The viral S protein is a homotrimer that protrudes from the virion surface (6) and is responsible for entry into susceptible cells by binding to the human angiotensin converting enzyme 2 (ACE2) protein (3-5). Once internalized, the virus starts to replicate within the cell (7). The nucleocapsid (N) protein of SARS-CoV-2, is the largest structural protein of the virus which coats its large genomic RNA and is responsible for creating its helical structure (8).

Compared to the viral S protein, the N protein is much more conserved (~90%), is expressed at high levels during infection, and is highly immunogenic (8). This is for example described in the publication Y. Cong, M. Ulasli, H. Schepers, M. Mauthe, P. V'kovski, F. Kriegenburg, V. Thiel, C. A. M. de Haan, F. Reggiori, *Nucleocapsid Protein Recruitment to Replication-Transcription Complexes Plays a Crucial Role in Coronaviral Life Cycle. J. Virol.* 94 (2019), doi:10.1128/JVI.01925-19.

Currently, oropharyngeal and nasopharyngeal swabs are primarily used for virus detection. However, it is not clear how many virus particles of SARS-CoV-2 are needed to trigger an infection. It has been anticipated that the corresponding dose to establish an infection in exposed people could be as little as 10 virus particles. Other studies suggest a relatively higher dose, ranging from a few hundred to thousands of particles. It has early been estimated and later confirmed in international medical reports that SARS-CoV-2 exhibits a higher rate of virus replication compared to SARS-CoV-1. The high level rate of virus replications of SARS-CoV-2 can quickly cause increased disease severity. Statistically, confirmed COVID-19 cases worldwide are 100 times higher than the confirmed cases of SARS and MERS. This is because, 1) SARS-CoV-2 replicates to much higher levels in the nose and mouth than SARS and MERS, and 2) this leads to very high levels of virus shedding in the environment by people who are either pre-symptomatic or asymptomatic. Thus, a huge percentage of infected people can transmit the virus without realizing that they are even infected.

Rapid detection methods independent of lab setting have been identified as one of the foremost priorities for promoting epidemic prevention and control. Currently, there are two main strategies for the detection of COVID-19. The first is a real time reverse transcriptase (RT) polymerase chain reaction (RT PCR)-based strategy that detects the viral nucleic acid in patient samples (presence of the viral RNA). The second strategy is an immunological assay that detects viral protein antigens or serum antibodies produced as a result of the body's immune response to the viral infection. The two strategies complement each other, with the qPCR strategy detecting the virus during its active phase, while the immunological assay identifies individuals who have developed antibodies to fight the disease.

Currently, the molecular technique of quantitative real time polymerase chain reaction (qRT PCR) is the gold standard for SARS-CoV-2 detection using samples from respiratory secretions. However, it is a time consuming and cumbersome procedure that takes long processing times over days for results. Several other molecular assays have been developed to detect SARS-CoV-2, such as enzyme-based assays like ELISAs, and rapid tests that aim to detect either antibodies against the virus or the viral antigen themselves. Nevertheless, most of these antigen-antibody-based assays have failed quality control due to their rapid development without proper testing and result in either false negative or false positive detection due to the long time it takes to develop serum responses to the viral infection (from days to two weeks). Although capacity for PCR testing as well as the quality of quick tests for coronavirus detection have been developed, the testing is inflexible and does not give a reliable quantification of virus present in a sample.

Another approach for virus detection that is applicable to the detection of coronavirus and protein-antibody interactions has been described for example in the patent application by the same applicant, U.S. patent application Ser. No. 17/379,496 for "Method and system for virus and protein-antibody interactions detection and monitoring based on optical light intensity and electrical parameters" based on U.S. 63/054,022 in the name of the United Arab Emirates University, inventors: Mahmoud F. Y. Al Ahmad, Tahir A. Rizvi, Farah Mustafa.

The advancement in the integration of bio sensing mechanisms and electrical characterization techniques, such as the approach mentioned above, have provided a powerful potential and huge impact in developing point of care systems. In principle biosensors are capable to transform biochemical information, such as analyte or particles concentrations into a corresponding electrical useful signal: current or voltage. Signal processing along with parametric modelling techniques have been developed for the purpose of deciding the outcome about a sample under test. Combining biosensor with wireless connectivity platforms and analysis capabilities have reduced the cost for employing such technology.

RELATED ART

Examples of related art with different assay methods and analysing techniques are found in various publications. For example, the patent publication US2017362668A1 to Meso Scale Technologies with the title Co-binder assisted assay methods disclose methods for reducing cross-reactivity between species employed in multiplexed immunoassays.

Another example of related art is found in the patent publication US2021123883A1 to University of Utah Research Foundation with the title Whole virus quantum mechanical tunnelling current and electronic sensors. This publication discloses a field effect transistor (FET) biosensor for virus detection of a selected virus within a sample volume.

A further example of related is the patent publication WO2021081476A1 to University of Utah Research Foundation with the title Zero Power visible colorimetric pathogen sensors. This piece of related art shows a method in which a visibly perceived colorimetric pathogen sensor comprises a substrate and a molecular recognition group coupled to the substrate. The molecular recognition group can bind a target pathogen and when that occurs, the reflected light cab be altered thereby changing apparent color, thus indicating the detected target pathogen.

The article with the title *An Analysis Review of Detection Coronavirus Disease 2019 (COVID-19) Based on Biosensor Application* by Bakr Ahmed Taha et al. summarizes technologies for the detection of coronavirus disease 2019 (COVID-19) technologies with biosensors that operate using laser detection technology.

The related art patent publication WO2011060184 to Cermed Corporation with the title Cervical cancer screening by molecular detection of human papillomavirus-induced neoplasia further shows point-of-care tools for screening biological samples for markers associated with pathogenic microbial infections. This publication discloses a technology for screening cervical cells for the expression of proteins that occur because of human papillomavirus infection and progression to invasive cervical cancer.

Another related art patent publication WO2015116083 to Hewlett Packard Development with the title Microfluidic sensing device. This publication discloses a microfluidic sensing device that comprises a channel and an impedance sensor within the channel. A particle in a fluid passing the sensor is identified based on the sensed impedance characteristics.

On a general level there is a need for efficient methods and systems for detection, identification and quantification of analytes in specimen comprising cells, such as virus of any kind, coronavirus, bacteria, fungus, protein or other analyte.

A more specific and current need is the need for a cost effective method and system that yields fast, cheap and accurate results of detection, identification and quantification of a coronavirus such as SARS-CoV-2, which may be used to slow the spread of the virus and monitor the vaccine development process.

SUMMARY OF THE INVENTION

The present disclosure describes embodiments for a method and a system of detecting, identifying and quantifying an analyte in a specimen comprising one or more cells using detection and monitoring interactions between an analyte in the specimen and a reagent being prone to engage in a binding activity with such an analyte present in said one or more cells, using detection and monitoring of interactions based on electrical and/or optical response to an electric field. The analyte may be virus of any kind, coronavirus bacteria, fungus, protein or other analyte. The specimen may be taken from a living being for example in a bodily from a human patient, or from an object subject to possible analytes being present for example on a surface.

The present disclosure further describes more specific embodiments for a method and system for coronavirus detection and quantification using virus and protein-antibody interactions detection and monitoring based on electrical and/or optical response to an electric field.

Embodiments disclosed herein comprises a system and an electrical method that measures the viral nucleocapsid protein and anti-N antibody interactions to differentiate between SARS-CoV-2 negative and positive samples for example captured on nasal swab samples. Under electrical bias, the cell opens up by the formation of pores in the cell membrane. The antibodies penetrate the cell through these pores and binds with the N protein of SARS-CoV-2 virus that is expressed during infection. In exemplifying usage of embodiments disclosed herein, it has been found empirically that SARS-CoV-2 in patient nasal swab samples would be detected within five minutes if gaussian-like binding profile are detected, otherwise, the sample is considered negative. The calculated cost of such a test would be less than 3$, which is the cheapest ever one can have compared to existing tests.

Embodiments disclosed herein comprises a method of detecting, identifying and quantifying an analyte in a specimen comprising one or more cells, the specimen being accommodated in a suspension medium, comprising: apportioning the suspended specimen into one or more test samples; optionally, adding a reagent to the one or more test samples, said reagent being prone to engage in a binding activity with an analyte present in a said one or more cells; applying an electric field with a first magnitude and with a second magnitude over said one or more test samples for a selected period of time, said second magnitude being higher than said first magnitude; measuring one or more electrical properties of said one or more test samples in response to said applied electric field for said first magnitude and for said second magnitude over said period of time; —identifying characteristics of said electrical properties responses; determining the presence, the identification and/or the quantity of the analyte based on the characteristics of said electrical properties responses to said first magnitude and to said second magnitude of the applied electric field.

In different embodiments of the method, the analyte is any of coronavirus, virus of any kind, bacteria, fungus, protein or other analyte.

Further embodiments of the method comprise:

determining of the presence, the identification and/or the quantity of analyte in addition or alternatively is based on differences in the characteristics of said electrical properties responses to said first and second magnitude applied electric field; and/or measuring optical properties responses of said one or more test samples in response to said applied electric of said first and second magnitudes; and determining the presence, the identification and/or the quantity of analyte based on the characteristics or on the differences in characteristics of said optical properties responses to said first magnitude and to said second magnitude of the applied electric field.

In embodiments of the method:

quantification of analyte is determined by detecting and estimating a count of binding events occurring between analyte and reagent as indicated in the electrical properties response characteristics after an electric field has been applied over the test sample; and/or detection of analyte is determined based on non-linearities found in the electrical properties response characteristics after an electric field has been applied over the test sample; and/or identification of a analyte is determined based on a detected occurrence and/or pattern of non-linearities in the electrical properties response characteristics after an electric field has been applied over the test sample; and/or the reagent is in the form of ACE2 antibodies, NC antibodies or anti-N antibodies, other suitable antibodies or a fluorescence based reagent; and/or the applied electric field is induced by applying a DC voltage or a pulsating AC voltage over said one or more test samples.

Embodiments of the method, comprises:

apportioning the suspended specimen into a first, a second and a third test sample;

arranging said first test sample to contain purely the suspended specimen;

adding a reagent in the form of ACE2 antibodies to said second test sample;

adding a reagent in the form of NC antibodies to said third test sample;

applying an electric field with a first magnitude and with a second magnitude over said first, second and third test samples for a selected period of time, said second magnitude being higher than said first magnitude;

measuring one or more electrical properties of said test samples in response to said applied electric field for said first magnitude and for said second magnitude over said period of time;

identifying characteristics of said electrical properties responses;

determining the presence, the identification and/or the quantity of analyte dependent on the characteristics and/or on differences in the characteristics of said electrical properties responses to said first magnitude and to said second magnitude of the applied electric field.

Further embodiments of the method comprise providing two or more test samples with specimen and an added reagent, and for said two or more test samples, simultaneously: —measuring electrical properties responses for an applied low magnitude electric field over said test samples; —measuring electrical properties responses for an applied high magnitude electric field over said test samples; —analyze characteristics of said electrical properties responses for said two or more test samples; thereby processing two or more test samples in parallel for increased efficiency; said electrical properties responses preferably being capacitance versus applied voltage responses.

In embodiments of the method there is comprised measuring optical properties responses, preferably light intensities, of said two or more test samples for said applied low and high magnitude electric fields.

Embodiments of the method, comprises:

providing a first set of two or more test samples with specimen and a second set of test samples with specimen and added reagent;

for one or more first pair of test samples with specimen and test samples with specimen and added reagent, measuring electrical properties responses for an applied low magnitude electric field over said first pairs of test samples;

for one or more second pairs of test samples with specimen and test samples with specimen and added reagent, measuring electrical properties responses for an applied high magnitude electric field over said second pairs of test samples;

analyze characteristics of electrical properties responses for said one or more first pairs and for said one or more second pairs of test samples;

optionally, comprising measuring optical properties responses, preferably light intensities, of said one or more first pairs and of said one or more second pairs of test samples for said applied low and high magnitude electric fields;

thereby processing multiple test samples in parallel for increased efficiency;

said electrical properties responses preferably being capacitance versus applied voltage responses.

Embodiments described herein comprises a system for detecting, identifying and quantifying an analyte in a specimen comprising one or more cells, the system comprising:

—a testing apparatus having a test sample holder arranged to house one or more test sample containers in a position in relation to one or more sets of electrodes configured to apply an electric field over a test sample in a test sample container and to conduct measurements of one or more electrical properties of a test sample in a test sample container.

In embodiments of the system the analyte is any of coronavirus, virus of any kind, bacteria, fungus, protein or other analyte.

Embodiments of the system further comprises a test sample container for a test sample of a specimen accommodated in a suspension medium, the test sample container being configured for applying an electric field over a test sample in the test sample container and/or configured to enable light passing through the test sample and the test sample container.

In embodiments of the system, the testing apparatus is configured to apply an electric field of a first, lower, magnitude and of a second, higher, magnitude over a said test sample in a said test sample container, wherein the applied electric field is induced by applying a DC voltage or a pulsating AC voltage over said test sample, said high magnitude electric field being generated by an applied voltage in the range of preferably 0.5 to 1 volt.

In other embodiments of the system the testing apparatus is configured to measure one or more parameters indicating electrical properties of a said test sample in a said test sample container for different magnitudes of applied electrical fields, for example a parameter indicating the capacitance of said test sample.

In embodiments of the system the test sample holder of the testing apparatus is further configured to hold the one or more test sample container in a position in relation to a light source to enable light to pass through the test sample and onto a light detector coupled to a device configured to measure parameters indicating optical properties of the test sample; and preferably said testing apparatus being configured to measuring optical properties responses of said one or more test samples in response to said applied electric of said first and second magnitudes.

Embodiments of system, further comprises: a processor provided with computer program code configured to determine the presence, the identification and/or the quantity of coronavirus based on the characteristics and/or on differences in the characteristics of said electrical properties responses to said first magnitude and to said second magnitude of the applied electric field; and/or a processor provided with computer program code configured to determine the presence, the identification and/or the quantity of coronavirus based on the characteristics and/or on the differences in characteristics of said optical properties responses to said first magnitude and to said second magnitude of the applied electric field.

Other aspects and embodiments of the invention will be apparent as will be shown in the detailed description of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings illustrate non-limiting example embodiments of the invention.

FIG. 1A to FIG. 1D illustrate SARS CoV-2 with spike protein structure and statistics of distribution and length of spike protein on a virus particle, wherein: FIG. 1A shows a β-coronavirus particle in a 3D illustration. FIG. 1B shows an example of the coronavirus particle structure in a vector image illustration. FIG. 1C shows a diagram of spike protein position distribution over the surface of the virus particle. FIG. 1D shows a diagram of spike protein variation in length.

FIGS. 25A to 26D show graphs of optical detection of the binding affinities between proteins and antibodies, wherein:

FIG. 26D shows NCP binding with the antibody after mixing outside.

FIGS. 27A to 27B show graphs of opto-electrical measurements of nucleocapsid protein (indicated NCP or NC protein) with direct current DC biasing, wherein:

FIG. 27A shows measured NC protein optical response versus time at different DC bias voltages.

FIG. 27B shows binding measurements between NC protein and its corresponding antibody after subjected the solution to an electric field.

FIGS. 28A to 28B show graphs of illustrating examples of protein-protein interaction measurements on paper based nitrocellulose membrane (NM), wherein:

FIG. 28A shows optical responses on nitrocellulose membrane (NM) alone, nitrocellulose membrane and spike protein (NM+P), and nitrocellulose membrane and antibody to spike protein (NM+AB) alone.

FIG. 28B shows optical responses to spike protein-antibody binding on the nitrocellulose membrane.

DETAILED DESCRIPTION

Figure 1A:
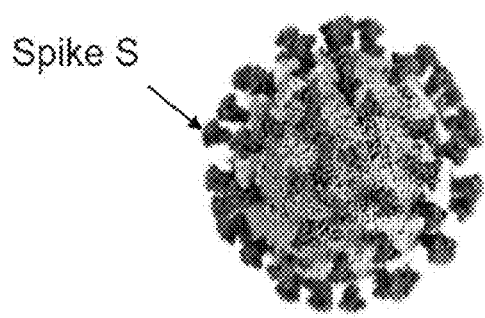

Throughout the following description, specific details are set forth in order to provide a more thorough understanding to persons skilled in the art. However, well known elements may not have been shown or described in detail to avoid unnecessarily obscuring the disclosure of embodiments. The following description of examples of the technology is not intended to be exhaustive or to limit the system to the precise forms of any example embodiment. Accordingly, the description and drawings are to be regarded in an illustrative, rather than a restrictive, sense.

Introduction

As has been seen with the recent COVID-19 pandemic, viral outbreaks or pandemics can result in numerous global, social and economic problems. In particular, this outbreak has highlighted the need for rapid diagnosis and detection mechanisms that can play major role in stop spreading the virus. Although some studies show that anywhere from a few hundred to a few thousand COVID-19 viruses are required for a person to contact COVID-19, other studies have shown that even as few as 10 viral particles can result in viral infection. Embodiments disclosed herein comprise a technology that is scaled to detect down to few virions.

The technology with electrical detection of specific viral antigen binding to a specific antibody has the potential to accelerate the development of a new generation viral detectors. Techniques as described herein enable high sensitivity, specific detection and quantitative signature based on the binding characteristics. Moreover, the application of electrical conditions over a sample can be used to enable and accelerate such binding interactions that are required for efficient electrical detection. In a more general sense, the technique enables the control of chemical reactions using electric field gradients.

The need for rapid cost efficient detection of analytes is in fact universal for several different kinds of target analytes, such as virus of any kind, bacteria, fungus, protein or other analyte, in particular for supporting the health care sector around the world.

Cell Characteristics

The typical structure of a biological cell is that a cell membrane encloses a nucleoid region with components such as a nucleus and/or other cell components suspended in cytoplasm. These components can interact in different manners with the environment of the cell. This is explained by means of an example detailing coronavirus characteristics.

Coronavirus Characteristics

The coronavirus SARS-CoV-2 appears as a spherical particle with external spike protein that displays crown-like appearance, as has been observed under an electron microscope. Corona virus (herein in short also called CoV) consist of positive-sense single-stranded RNA of approximately 27-32 kb (kilobase, unit equal to 100 base pairs bp of RNA or DNA). Its envelope is approximately 100 nm (nanometer) in diameter and the spikes are oligomers of the 180-200 kDa (kilodalton, atomic mass unit) S glycoprotein that can bind to the host cell. Thus, SARS-CoV-2 belongs to the betaCoVs category (betacoronavirus genus). It has round or elliptic and often pleomorphic form, and a diameter of approximately 60-140 nm (nanometer). Like other CoVs, it is sensitive to ultraviolet rays and heat. Ultraviolet (UV) is electromagnetic radiation with wavelength from 10 nm to 400 nm (750 THz). The spike protein appearances are much smaller much smaller in size than the particle itself with high aspect ratio, where the spike protein measures 1-5 nm and has an atomic mass of less than 200 kDa and has an arm of sub-nanometer dimension.

Several published reports suggest that SARS CoV-2 could be able to bind to the angiotensin-converting enzyme 2 receptor in humans. Nevertheless, the complete virus structure analysis and its future evolution, adaptation, still require further investigations.

The genomic characteristics of 2019-nCoV as well as similarities and differences to other coronaviruses has been discussed in the publication titled "Genomic characterisation and epidemiology of 2019 novel coronavirus: implications for virus origins and receptor binding" Lu et al, 2020. Based on the genome sequences of 2019-nCoV it could be concluded that the outbreak was detected relatively rapidly after the first occurrences of infection in human patients. It has been found that the recombinant RBD protein bind strongly to human ACE2 (hACE2) and bat ACE2 (bACE2) receptors and it blocked the entry of SARS-CoV-2 and SARS-CoV into their respective hACE2-expressing cells, as discussed also in the publication titled "Characterization of the receptor-binding domain (RBD) of 2019 novel coronavirus: implication for development of RBD protein as a viral attachment inhibitor and vaccine", Tai et al, 2020.

A coronavirus is composed of four structural proteins incorporating spike (S), envelope (E), membrane (M), and nucleocapsid (N) proteins. S protein plays the most important roles in viral attachment, fusion and entry. The S protein mediates viral entry into host cells by first binding to a host receptor through the receptor-binding domain (RBD) in the S1 subunit and then fusing the viral and host membranes through the S2 subunit. Furthermore, it serves as a target for development of antibodies, entry inhibitors and vaccines.

SARS-CoV-2 particle diameter approximately ranges from 60 to 140 nm with distinctive spikes about 8 to 12 nm in length, as disclosed in the publication titled "A Novel Coronavirus from Patients with Pneumonia in China, 2019", Zhu et al, 2020. In average the virus volume is of about $10^{-3}$ femtoliter with mass of 1 femtogram as disclosed in the publication titled "Science Forum: SARS-CoV-2 (COVID-19) by the numbers", Bar-On et al, 2020. The virus concentration levels have been reported in several diagnoses as per follow: Nasopharynx $10^6$-$10^9$ RNAs/swab; throat $10^4$-$10^8$ RNAs/swab, Stool $10^4$-$10^8$ RNAS/g and Sputum $10^6$-$10^{11}$ RNAS/mL, the RNA counts can markedly overestimate infectious virions, which is discussed in the publications titled "Virological assessment of hospitalized cases of coronavirus disease 2019", Wölfel et al. 2020, and another publication titled "Viral load of SARS-CoV-2 in clinical samples", Pan et al, 2020.

Figure 1B:
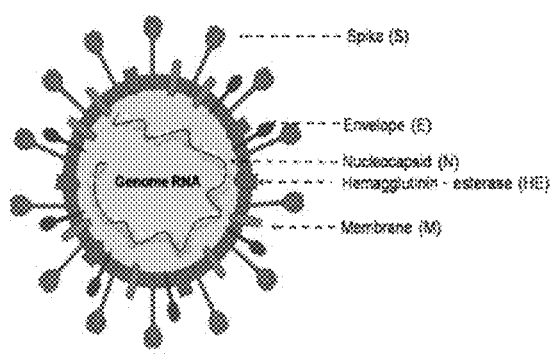
Figure 1C:
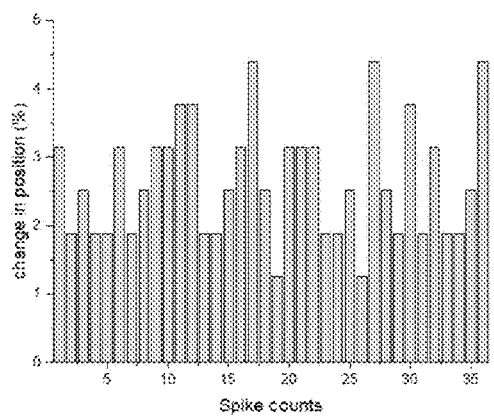
Figure 1D:
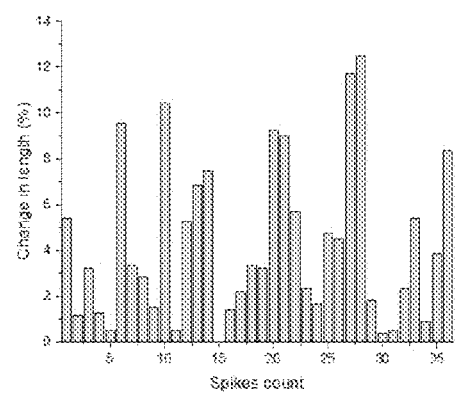

FIG. 1A to FIG. 1D illustrate SARS CoV-2 with spike protein structure and statistics of distribution and length of spike protein on a virus particle. FIG. 1A shows a β-coronavirus particle in a 3D illustration. FIG. 1B shows an example of the coronavirus particle structure in a vector image illustration. FIG. 1C shows a diagram of spike protein position distribution over the surface of the virus particle. FIG. 1D shows a diagram of spike protein variation in length.

FIG. 1A illustrates the three-dimensional (3D) structure of a SARS CoV-2 virus particle. The SARS CoV-2 virus particles are ranging in shape from round to elliptical and often pleomorphic form, as for example described in the publication titled "Architecture of the SARS coronavirus prefusion spike", Beniac et al, 2006. Spikes S appear distributed over the surface of an envelope protecting the virus genome.

The cross section of a virion, i.e., a virus in the form of an independent particle when appearing not inside an infected cell or in the course of infecting a cell, is depicted in FIG. 1B. The virus is composed of several viral components incorporating several compositions, as described in the publication titled "Severe Acute Respiratory Syndrome Coronavirus 2 (SARS-CoV-2): An overview of viral structure and host response", Astuti et al, 2020. The SARS-CoV-2 main components are: a double-layered lipid envelope, Spike glycoprotein (S), Envelope protein (E), Membrane glycoprotein (M), and Nucleocapsid protein (Nucleocapsid protein (N), as described in the publication titled "Coronavirus envelope protein: current knowledge", Schoeman et al, 2019. The virion's crown-like spike proteins constitute a multifunctional molecular machine that not only mediates coronavirus entry into host cells, as described in the publication titled "Structure, Function, and Evolution of Coronavirus Spike Proteins", Fang li, 2016. The multifunctional molecular machine will also drive the interactions between the virus particles with its surrounding media, as described in the publication titled "Crystal structure of SARS-CoV-2 main protease provides a basis for design of improved α-ketoamide inhibitors", Zhang et al, 2020.

The spike protein distribution across the virus particle surface can be explored with the help of electron microscopy images, as described in the publication titled "Brief Review on COVID-19: The 2020 Pandemic Caused by SARS-CoV-2", Damian N. Valencia, 2020. With the help of image processing tools the spike protein variation in position and in in length have been extracted and their distribution versus spike protein counts are represented by FIG. 1C and FIG. 1D, respectively.

As illustrated in FIG. 1A and FIG. 1B, SARS-CoV-2 is densely decorated with a forest of spike proteins. FIG. 1C shows a diagram of spike protein position distribution over the surface of the virus particle. The width of the protein spikes in SARS CoV-2 extends from ~1% to 4.5% of the virion diameter. FIG. 1D shows a diagram of spike protein variation in length. The spikes length varies between 0.5% up to 13% of its diameter.

As an example for a virion of 100 nm diameter, the distances between the spikes varies from 1 nm to 4.5 nm; and its length varies from 0.5 nm to 13 nm. These features have been extracted using imported SEM images relying on image pixel assessment. The number of spikes per virus circumference is approximate of 35 spikes, and of around more than 300 spikes per virus particle with complex randomly distributed pattern and not equal spaced.

Figure 2:
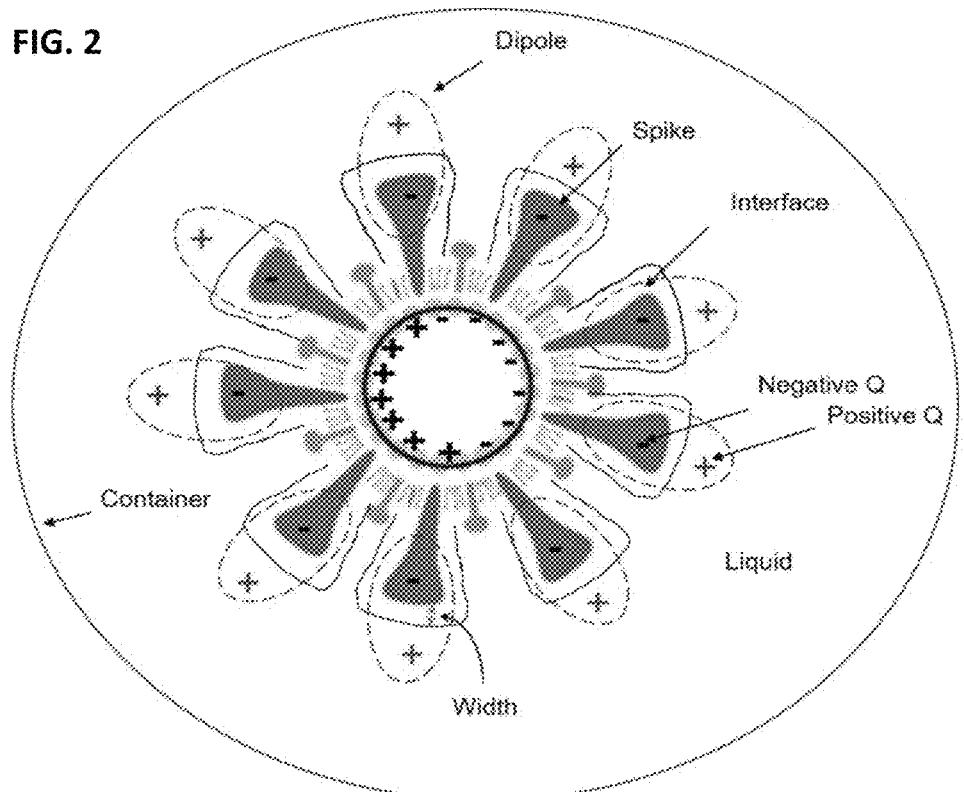
FIG. 2 shows an illustration of SARS-CoV2 virus interaction with its surrounding aqueous suspension medium in a container with the application of an electric field.

FIG. 2 shows an illustration of SARS-CoV-2 virus interaction with its surrounding aqueous and liquid suspension medium in a container with the application of an electric field. The electrical interactions between the SARS-CoV-2 virions and its surrounding enables their electrical detection. Thus, as shown in FIG. 2 a SARS-CoV-2 virion has a number of spikes projecting from its surface and having a width in relation to an interface layer. The polarization pattern under an applied electric field, as illustrated in FIG. 2, is such that the heads of the spikes have a negative charge (Q) and particles present in the suspension medium has a negative charge (Q). Dipoles are formed when negatively charged particles bind to the positively charged spikes.

Figure 3A:
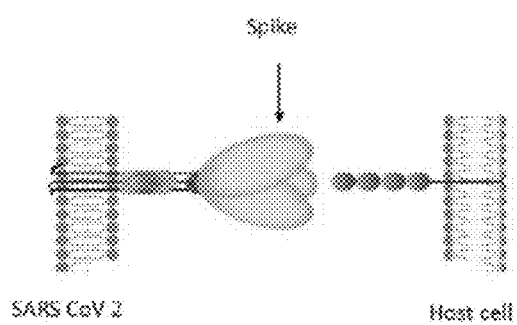
FIG. 3 shows an exemplifying illustration and modelling of binding mechanisms, w
Figure 3B:
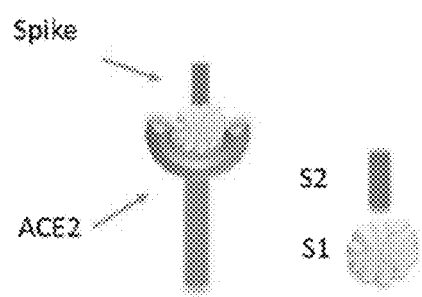
Figure 3C:
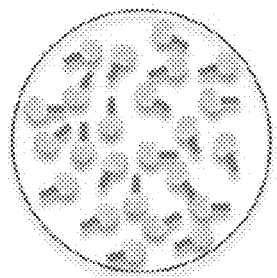
Figure 3D:
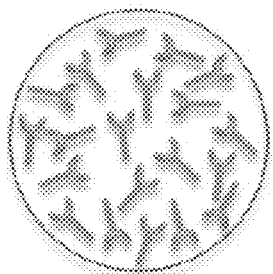
Figure 3E:
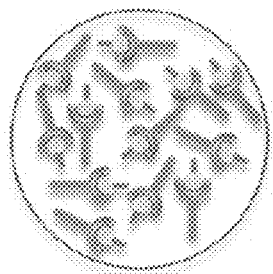

In the illustration of FIG. 2, the virion, i.e., the virus particle, is assumed to be suspended in aqueous transportation medium of nasopharyngeal swabs. With applied electric field, current will be induced and flows on the virus surface. Due to the SARS-CoV-2 capsid structure and its internal composition, the overall net charge assumes zero, as described in the publication "Coronavirus envelope protein: current knowledge" Schoeman et al, 2019. The spikes protein will have the maximum current flows at their surfaces and sharp edges. An interface effective layer is formed because of the interaction between the surface charge density on the spikes and the surrounding medium, as described in the publication titled "Electrical Detection, Identification, and Quantification of Exosomes", Mahmoud Al Ahmad, 2018. FIG. 2 further illustrates this interface layer and its width. The interface layer exhibits its maximum width when both of them have same polarity, and exhibits its minimum width when they have opposite polarity. As the width decreases the coupling increases enabling the virus electrical detection, as described in the publication titled "Reversible Voltage-Induced Assembly of Au Nanoparticles at Liquid|Liquid Interfaces", Su et al, 2004. When both the net charges of the medium and virion have opposite polarity, an electrical dipole with infinitesimal separation are created as shown in FIG. 2. This is due to the variations in spike lengths and a non-uniform array of non-identical dipoles that is equivalent to the surface charges. Those dipoles will be aligned with the application of electric field whether it is constant or time varying, which enables the impedance measurements, as described in the publication titled "Virus detection and quantification using electrical parameters", Al Ahmad et al, 2014. Due to its spikes forming crown-like thorns the SARS CoV-2 virions exhibits stronger polarization than other viruses.

FIG. 3 shows an exemplifying illustration and modelling of binding mechanisms of virus to surrounding media. FIG. 3A schematically illustrates SARS-CoV2 binding with a host cell. FIG. 3B In this example, binding of ACE2 (angiotensin converting enzyme 2) and Spike protein along with illustration of the spike protein subunits, S1 and S2. FIG. 3C schematically shows the distribution of the, in this example, spike protein in suspension. FIG. 3D schematically shows the distribution of ACE2 in suspension. FIG. 3E In this example, schematically shows the distribution of ACE2 and S protein after binding in suspension.

There are several antigens and elements in SARS-CoV2 virus that are active in binding and/or interaction, ACE2 is one example, nucleocapsid is another example and the technology of the present disclosure is applicable to other antigens and elements as well. The technology of embodiments disclosed herein can, as described herein, be applied on any virus, antigens, antibodies or elements.

For the sake of example, embodiments herein are explained with application of the technology on ACE2 and nucleocapsid. In terms of detection, one of the most prominent features of the SARS-CoV-2 virus, like other coronaviruses, is the spike protein (S) that protrudes out of the virus particle essentially like “spikes”; hence the name. The spike protein forms a trimer that is used by the virus to enter susceptible cells using the angiotensin-converting enzyme 2 (ACE2) protein as the cellular receptor, the same protein used by the SARS-CoV-1 virus that caused the first SARS epidemic in 2003 (FIG. 3A). The spike protein is cleaved by host cell membrane proteases into two subunits: the surface subunit S1, and the transmembrane subunit S2 (FIG. 3B). It is the surface S1 subunit that is used by the virus to interact with ACE2 protein using its receptor binding domain (RBD). This allows the virus to attach to the susceptible cells, while the S2 protein is used for the actual fusion of the virus with the cell membrane, allowing the virus to be endocytosed into the cytoplasm and release its genomic RNA cargo, wrapped up in the nucleocapsid protein (NCP), into the cytoplasm. It is this RNA that is immediately used to translate viral proteins and use them for successful virus replication in the susceptible cells. The spike protein is also the most immunogenic domain of the virus towards which most of the neutralizing antibody responses against the virus are generated in infected individuals, making it an ideal candidate for vaccine as well as a target of drug development. In the context of COVID-19, it has been observed that the SARS-CoV-2 spike glycoprotein binds ACE2 with much higher affinity than SARS-CoV-1 spike protein, which may explain the higher transmissibility of SARS-CoV-2 in the human population.

A reagent such as the ACE-2 as well as the nucleocapsid antibody NC, or any other possible antibody or other suitable reagent, can be introduced into the virus cell by electro-poration methods or any other type of method that can allow the cell content to go outside in the suspended media or allowing the antibodies to go inside the cells. In embodiments an electrical pulse is applied to the cells in the specimen of a test sample to stimulate interaction between a reagent and the virus cell. The cell permeability increases, due to pore formation in the cell membrane. The pores only stay open for the duration of the applied constant field or its time domain variation. The corresponding antibody penetrates the cell through these pores and binds with the antigen. In case of ACE-2 antibody it will bind with the Spike protein of SARS-CoV-2 virus. This Spike protein can be used as reliable markers for the indication of the presence of infection and of virus replication, since it causes the COVID-19 disease.

FIG. 4A to FIG. 4C show an illustration of how a cell is acting at different stages when an electric field is applied, and the FIG. is used to illustrate electro-poration based insertion of a reagent. The drawings in FIG. 4 illustrates a cell, such as a virus cell or virion, or a normal cell with a content of genetic material depicted as a solid red blob surrounded by a membrane depicted as an oval outline and with green dots representing reagent particles such as protein, antibodies or other chemicals. In FIG. 4A no electric field is applied over the cell and the reagent particles remain outside the cell membrane. FIG. 4B shows an initial stage with an electric field applied over the cell, illustrating how pores are formed in the cell membrane allowing reagent particles to enter into the cell. FIG. 4C shows a later stage with an electric field applied over the cell, and illustrates how the membrane is closed and reagent particles are trapped inside the cell membrane. This mechanism is used by embodiments described herein.

FIG. 5A to FIG. 5D show an illustration of SARS-CoV-2 N protein and with anti-N Ab binding (also called NC antibody binding) in a cell infected with SARS-CoV-2 virus. FIG. 5A illustrates a cell before electroporation, i.e., without any electric biasing, the cell thus having a closed membrane. The depicted cell contains a nucleus, SARS-CoV-2 virions, free genomic RNA-N protein complex and N protein. FIG. 5B depicts the cell with electrical biasing caused by an electric field being applied over the cell or, more specifically, over a test sample containing the cell in a suspension medium and with a reagent in the form of anti-N antibodies (also called NC antibodies) present in the suspension medium surrounding the cell. As illustrated the cell membrane have temporary holes and anti-N antibodies passes through the temporary holes by electroporation. After anti-N antibodies having entered into the cell there will be occurrences of anti-N antibodies bound to N protein in the RNA-N protein complex and anti-N antibodies bound to N protein, as illustrated. FIG. 5C shows an illustration of the binding interaction modelling with an antibody bound to an N protein. FIG. 5D shows an illustration of the orientation of protein-protein dipoles in surrounding media with the application of electrical bias by an electric field.

Detection, Quantification and Identification of Coronavirus and Other Analytes

In embodiments, negative and positive specimen from COVID 19 patients and suspected patients are loaded into individual test samples. A regent, such as ACE-2 antibodies or NC antibodies also called anti-N ab. The selected reagents bind specifically to components of the SARS-CoV-2 virus. Under electrical bias, the virus cell opens up by formation of pores in the cell membrane. So, for example the anti-N antibody penetrates the cell through these pores and bind with the N protein (i.e., the nucleocapsid protein which herein is also called NC protein) that is expressed during infection. For the purpose of embodiments this binding event is used as a reliable marker for the presence of SARS-CoV-2 infection.

In accordance with the concepts described herein different embodiments are applied on different analytes, such as coronavirus, virus of any kind, bacteria, fungus, protein or other analyte. In embodiments of such a system including a method and an apparatus, of detecting, identifying and quantifying an analyte in a specimen comprising one or more cells, the specimen is accommodated in a suspension medium. The suspended specimen is preferably apportioned into one or more test samples. Optionally, a reagent is added to the one or more test samples, wherein said reagent is prone to engage in a binding activity with an analyte present in a said one or more cells. An electric field with a first magnitude and with a second magnitude is applied over said one or more test samples for a selected period of time, wherein the second magnitude is higher than said first magnitude. One or more electrical properties of said one or more test samples in response to said applied electric field are measured for said first magnitude and for said second magnitude over said period of time. Characteristics of said electrical properties responses are identified, and the presence, the identification and/or the quantity of the analyte are determined based on the characteristics of said electrical properties responses to said first magnitude and to said second magnitude of the applied electric field.

Figure 6:
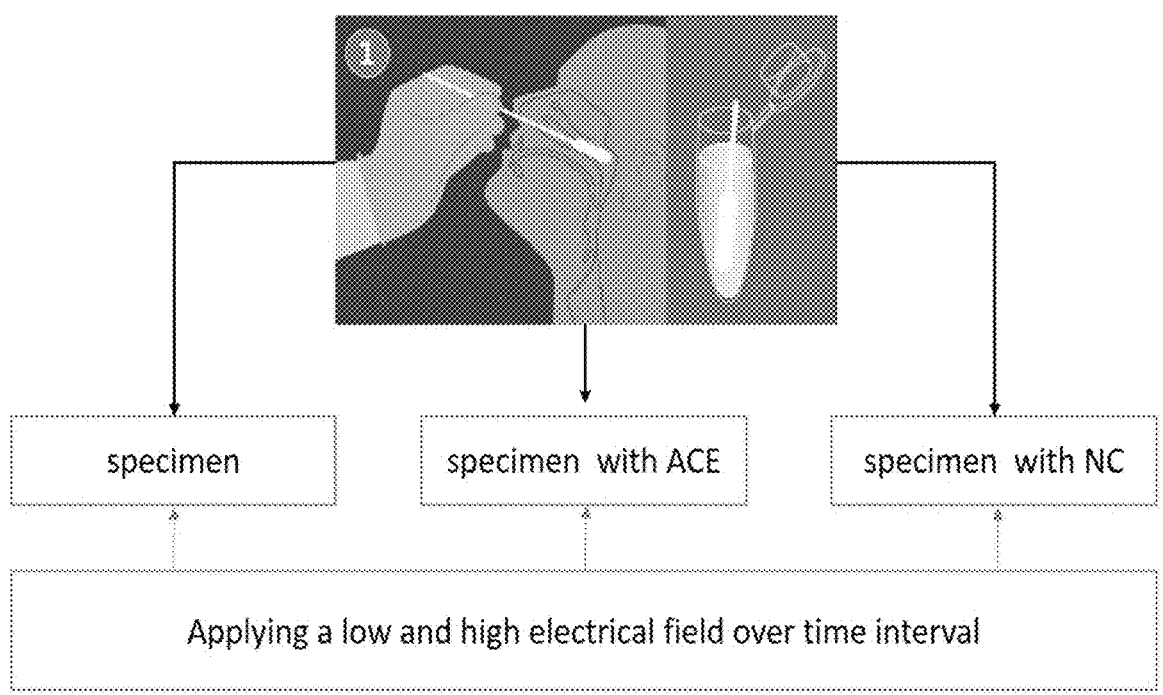

FIG. 6 shows an overview of an exemplifying embodiment of a system for detection, quantification and identification of coronavirus. The system comprises method and apparatus in accordance with embodiments exemplified herein.

In exemplifying embodiments of such a system for detection, quantification and identification of coronavirus, a specimen is obtained from a patient using a nasopharyngeal swab. The swab is placed in a suspension medium such as a viral transport medium (VTM) solution or any other possible suspension liquid media, for example but not limited to blood, urine and saliva, and gently shaken to transfer the viruses from the swab to the suspension medium. The specimen accommodated in a suspension medium is put in a test sample container. A pure specimen test sample and/or a test sample with an added reagent are prepared and are for testing placed in a testing apparatus. An electric field, preferably a low magnitude and a high magnitude electric field is applied over the test sample in the testing apparatus. After or during the application of the electric field, electrical and/or optical responses are measured and recorded individually or simultaneously. The responses are processed individually or simultaneously to extract or determine one or more sets of parameters that in different embodiments are used for detection, quantification and identification of coronavirus. In different embodiments, determining the presence, the identification and/or the quantity of coronavirus is based on the characteristics and/or on the differences in characteristics of said electrical responses and/or said optical properties responses to said first magnitude and to said second magnitude of the applied electric field.

Figure 7A:
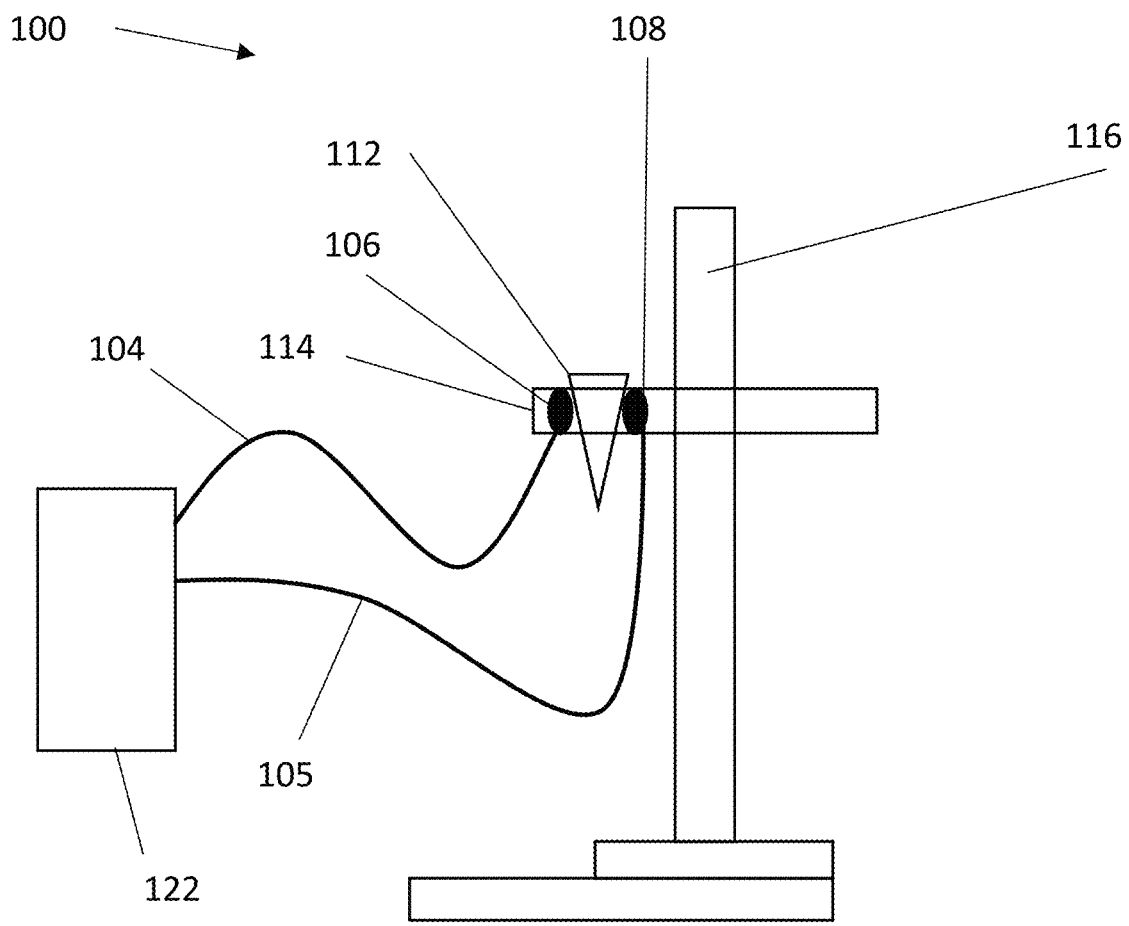
Figure 7B:
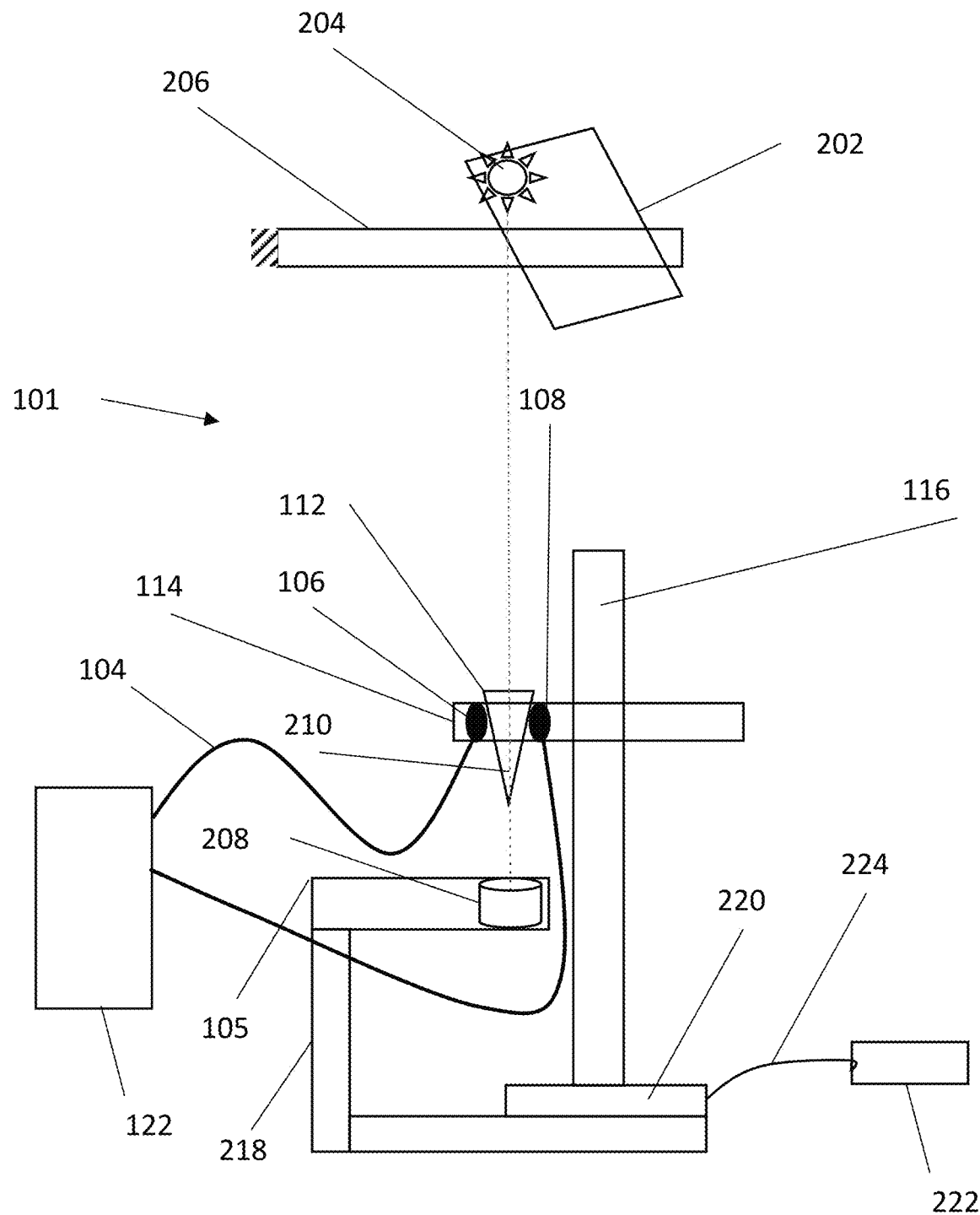

FIGS. 7A and 7B show illustrations of the concept of electrical and/or optical detection in accordance with embodiments in an experimental setup utilized to illustrate an exemplary embodiment of a testing apparatus.

FIG. 7A shows an embodiment equipped for electrical detection 100. A stand 116 is provided with a test sample holder 114 configured to hold a test sample container 112 in a position in relation to first and second electrodes 106, 108. In FIG. 7 the electrodes are coupled to an electrical analyzer 122 via a set of cables 104, 105. In such an exemplifying embodiment, the electrical analyzer is for example a Gamry reference 3000 electrical analyzer devised to apply a voltage over the test sample as well as to measure electrical parameters indicating the electrical properties response of a test sample in the test sample container. Such an analyzer may also be devised to record measurement values and/or be further coupled to a processing device, for example a PC or other computer, configured to record and process measured parameter values.

Figure 20:
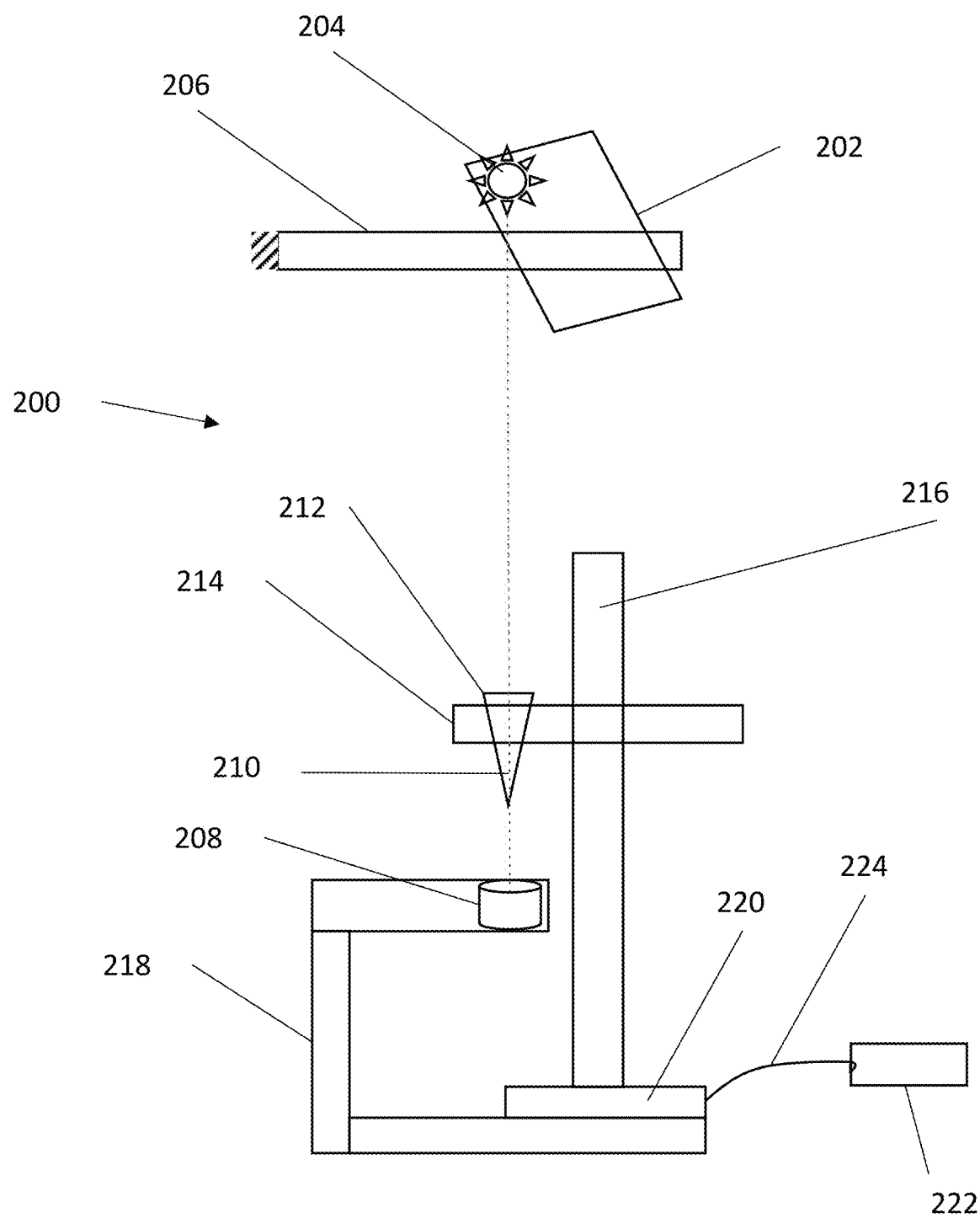

For the purpose of embodiments employing measurement of electrical as well as optical response parameter values, embodiment apparatuses would be configured as a combination of an arrangement comprising features configured for applying an electric field and measuring electrical response parameters as outlined in the example in FIG. 7A with an arrangement comprising features configured for measuring optical response parameters as outlined in the example described in conjunction with FIG. 20. This is shown in FIG. 7B, which thus shows an embodiment of an electrical and optical measurement setup 101 comprising a light source unit 202,204 here illustrated as a smart phone 202 with a built in LED-light as a light source 204. The light source 204 is, with the light source unit 202 mounted on fixture 206, aligned with a spectrometer for example in the form of a mini-spectrometer 208 utilized to collect light waves passing through a sample 210 to be analyzed. The sample 210 is kept in a container 112 in the form of a cuvette placed in a holder 214 that is mounted on a stand 116. The spectrometer 208 is mounted in a spectrometer stand 218 with its electronics 220 coupled to a PC 222 or other control or processing device via control and/or data cable 224. The electrical measurement values and the optical measurement values are in some embodiments captured and collected separately and in other, preferred embodiments partly common, coupled and/or synchronized for capturing and collecting electrical and optical measurement values. A processing device is configured to process electrical and/or optical measurement values dependent on preset rules, relations and/or with AI functionality in order to determine detection, identification and/or quantification of analytes, for examples corona virus.

Thus, in a use case example of operating this experimental setup, the electrical analyzer is used to apply the required electrical condition over the test sample and to collect the corresponding electrical responses. For example, positive and negative specimen samples from patients may be extracted from the upper respiratory tract by nasopharyngeal swabs suspended in viral transport media (VTM) to form positive and negative test samples. In order to confirm and calibrate the test results of embodiments, specimen have been confirmed clinically for their virus status using real-time RT PCR identification of SARS-CoV-2 RNA, following all relevant guidelines and regulations. The individual specimen are loaded as test samples into test sample containers, for example in the form of 0.4 cm-gap micropulser electroporation cuvettes from Bio-Rad. This exemplifying test sample container cuvette incorporates aluminum electrodes plates with an area of 1 cm by 0.8 cm. Its outer dimensions are 12.5×12.5×45 mm with a path length of 10 mm and a functional volume between 50-1,500 μl. With a test sample container comprising electrode plates, the electrical analyzer may be coupled via cables 104, 105 directly to the test sample container or via electrodes 106,108 in contact with such electrode plates or positioned in close proximity to the test sample container.

In a general embodiment of detecting and quantifying coronavirus in a specimen from a patient, the specimen is accommodated in a suspension medium, such as the mentioned viral transport medium (VTM) or other suitable suspension liquid medium. Exemplifying embodiments show nasal swabs being used in the procedure of obtaining a specimen and preparing a test sample. However, the system and methods are not limited to that and in different embodiments any specimen taken from living beings such as humans or animals, or non-living entities such as object surfaces, wastewater, liquid substances or food.

The suspended specimen is apportioned into one or more test samples and a reagent, for example in the form of an antibody, is added to the one or more test samples. An electric field with a first magnitude and with a second magnitude is applied over said one or more test samples for a selected period of time, where said second magnitude is higher than said first magnitude. One or more electrical properties of said one or more test samples in response to said applied electric field are measured for said first magnitude and for said second magnitude over said period of time. Characteristics of said electrical properties responses are identified. The presence, the quantity and/or the identification of coronavirus is determined dependent on characteristics or on differences in characteristics of said electrical properties responses to said first magnitude and to said second magnitude of the applied electric field.

The reagent is in different embodiments ACE2 antibodies, NC antibodies, other suitable antibodies or a fluorescence-based reagent. In other embodiments, the reagent may be a protein devised for testing on protein-protein binding or other reaction, an antibody or an antigen devised for testing on antibody-antigen binding or reaction with embodiments of the method and system adapted to that. The reagent may in different embodiments be in the form of a single type or a mix of a plurality of types, for example a single type antibody or a mix of different type antibodies. For analytes in the form of virus in general, the reagent is for example the specific antibody to bind with the specific antigen and/or the specific nucleocapsid antibody to bind with the nucleocapsid protein specific antigen. In embodiments, testing on a test sample with pure specimen, i.e., having no reagent added, is comprised either as a stand-alone test or in combination with the testing of one or more test samples having a selected reagent added.

In order to apply the electrical field over the one or more test samples and to measure the electrical properties responses to the applied electrical field of the test samples, the one or more test samples in their test sample containers are placed in or on a test sample holder arranged to house the test sample containers in a position in relation to a selection of electrodes. Such an arrangement comprises electrodes that are configured to apply an electric field over the test samples as well as probe electrodes configured to conduct measurements of one or more electrical properties of the test sample. In different embodiments the electrodes have different configurations. For example, the electrodes for applying an electric field and the probe electrodes may be the same set of electrodes coupled in different circuits. In other examples, the electric field application electrodes and the probe electrodes may be arranged in different sets of electrodes. Some embodiments of test sample holders are adapted to house and test one test sample at a time. Other embodiments of test sample holders are adapted to house and test a plurality of test samples in parallel or serially, for example two, three or more test samples at a time. The test sample holder and electrode arrangement may in embodiments for handling a plurality of test sample containers be configured for applying an electric field and measure electrical and/or optical properties per individual test sample container, in parallel or consecutively in series. The test sample holder may in different embodiments for example be configured as a chamber, an adaptor, a container or a plate that holds the specimen in its test sample container in a defined position in a testing apparatus.

The magnitudes of applied electric field is selected dependent inter alia on the dimension and the materials of the test sample container holding a specimen and of the test sample holder of the testing apparatus. In embodiments the magnitude of the applied electric field may for example be caused by applying a voltage between 0 and about 3 volts over the test sample. In different embodiments the applied electric field may be caused by an applied voltage in a constant or pulsated form, DC or AC voltage. The applied electric field and/or the applied voltage inducing the electric field may range from negative to positive and may in embodiments be swept over negative to positive values as well as zeroes. Different embodiments comprise applying one, two or a further plurality of kinds of applied electric fields, i.e., fields with different magnitudes or caused by different magnitudes of applied voltage, such as low and high. Increasing the applied voltage over about 3 volts will result in essentially burning the suspension medium and destroy it with its content of cells with analytes such as coronavirus, virus of any kind, bacteria, fungus, protein or other analyte and/or reagents. Thus, an applied bias voltage should result in induction of a current across the suspension and if this current is high enough, it should have the potential to destroy the protein physiology and functionality, resulting in the loss of specific protein-protein interactions. So for example, with the analyte coronavirus it has been found that one volt bias, i.e., voltage applied over a test sample is preferable and an optimum value that promotes the entry of the anti-N antibody into cells without changing the configuration and physiology of the viral nucleocapsid protein, the cells, buffer, antibodies or other reagents. The applied voltage may in embodiments be in the range of −3 to 3 volts, for example for coronavirus or other analytes.

The applied electric field may be generated by a DC or AC voltage in any general form, for example as a pulsed electric field. The electric field may in further variants be applied as a plane wave.

The application of a high magnitude electric field induced by a high electric voltage applied over the test samples cause reagents to enter and/or interact, for example in binding events, with a coronavirus virion, which in accordance with embodiments are detected by measuring electrical properties responses and/or optical properties responses of the test samples. In further embodiments, the transport of reagents such as antibodies to the inside the cell or the transport of cell content to the outside of its membrane is carried out also through other methods of cell transport such as for example "Diffusion". This can also be carried out by scratching the cells using the nano or micro-pored electrodes. In such embodiments the cell suspension can be inserted inside sandwiched flexible nanopore electrode-based system, then by exerting force across these two electrodes bringing them close to each other. The cell contents will in this procedure be transported out on the electrode surface and reagents such as antibodies can then be added to this content. These electrodes can be used to collect electrical responses before and after the addition of antibodies of the scratched cell suspensions. In this scenario, there is no need to apply a high magnitude electric field over the test sample.

The electrical properties of the test samples that are measured are different in different embodiments. For example, in embodiments the impedance with its magnitude and phase is measured and recorded over a selected period of time. For this purpose, the testing apparatus comprises an electrical analyzer or other measuring equipment configured to measure selected electrical properties of test samples placed in the testing apparatus. The measurements are in different embodiments, where a plurality of test samples are processed, performed in parallel or in sequence for two or more than two different electric fields. In different embodiments, measurement can be performed on a test sample before a reagent is added, i.e., on a pure specimen test sample, and after the reagent is added. The measurement may in embodiments be conducted for a non-zero applied electric field at different time steps, with such an applied electric field being generated by a DC or AC voltage in any general form, for example as pulsed electric field.

As mentioned, different sets of electrical measurements are conducted in different embodiments to extract parameters representing the electrical properties responses to applied electric field. For example, impedance related parameters with magnitude and phase versus an entity representing the applied electric field, and/or capacitances versus voltages applied over the test sample at operating frequency which can be ranged from $\theta$ to infinity.

In further embodiments, responses of optical properties of the test sample to an applied electric field are measured and recorded, as an alternative to or in combination with measurement of electrical properties. In such embodiments, light passing through a test sample is detected by a suitable optical detector such as described in embodiments in the present disclosure. Based on the refractive index and dielectric constant relationship, and as the capacitance changes with the applied electric field, the optical responses will also change with the applied electric field. The optical properties response profile will also change due to the interaction/binding events due to protein-protein or antibody-antigen reactions occurring in a test sample. This is reflected in for example measured light intensities of one or more of transmitted light, absorbance, scattered light and/or reflected light, as described in embodiments disclosed herein. In embodiments, optical properties response parameters are correlated with electrical properties response parameters in order to further enhance the detection, identification and quantification of coronavirus. Smart chart approaches or relationships may be used to conduct or generate such correlation.

Thus, in embodiments, there are combinations of measurements of optical and electrical properties responses to one or more applied electric fields. In different measurement and/or test sample scenarios the optical and electrical response parameters are measured for single or multiple applied electrical fields at single or multiple operational frequencies, in testing schemes with parallel or sequential testing of different test samples.

The extracted or measured parameters representing the electrical properties or optical properties responses are in embodiments further processed to extract one or more further sets of parameters that are used to determine detection, identification and quantification of coronavirus. In embodiments, a list of reference parameters, also called reference coefficients, is defined or determined from corresponding measurements of test samples with specimen alone or test samples with specimen and added reagent, such as antibody or protein. Measured parameters representing a response after a selected time period, that for example may be sub seconds to sub days long, are then compared with the determined reference parameters. The measured parameters are in embodiments correlated with the reference parameters, for example by means of calibration curves or mathematical modelling, to determine the presence, the identification and/or the quantity of the analyte, for example coronavirus, dependent on differences in parameters from responses to different electric fields and/or different test samples. In further embodiments, these parameters are used to determine the infection stage in an infected human or animal patient.

The selected period of time may, as in different embodiments, be selected to last for intervals ranging from sub seconds to hours, or sub days or days.

Test scenarios are varied in different embodiments. For example, as applied on the analyte coronavirus, single test samples or sets of test samples comprising a test sample:

with a specimen tested alone with no antibodies or protein; and/or with specimen and antibody 1 or protein 1;

with specimen and antibody 2 or protein 2;

with specimen and antibody N or protein N, where N=0 to infinity.

Also, there are embodiments with selected combinations of specimen with antibodies or proteins. Also, the antibodies or proteins could be functionalized particles as well, that is comprising functional features adapted to or selected for the specific usage.

A more specific exemplifying embodiment comprises the employment of three test samples, here exemplified with the analyte coronavirus. The first test sample is purely the specimen. Reagents in the form of ACE-2 and NC antibodies are added to the second and third test samples respectively. The samples are placed in a test sample holder of a testing apparatus and the electrical properties of the test samples are measured. First electrical properties relating to impedance, for example magnitude and phase, of each of the test samples are measured and recorded under the application of 0 volts over the test samples, resulting in a low or a non-existent first magnitude electric field for a selected period of time, for example 400 S (seconds). Then the same electrical properties of each of the test samples are measured and recorded under the application of 1 volt, resulting in a high second magnitude electric field for the same period of time.

The presence, quantity and/or the identification of the analyte, here exemplified with coronavirus, in the test samples are deducted from the characteristics of the measured and recorded electrical responses to the different applied electric fields. So, for example, negative samples show a generally flat rising profile of electrical characteristics response, whereas positive samples exhibit non-linearities. The degree of nonlinearity and the differences between zero or low voltage profiles and high voltage profiles can then be correlated with a measure for the concentration of the virus. The quantification of the virus is in embodiments determined based on the concentration of the virus, or as in other embodiments based on a correlation of the virus quantity with the degree of nonlinearity and the differences between zero or low voltage profiles and high voltage profiles. Similarly, identification of virus present in the test samples are in embodiments based on parameters correlated to for example the characteristics of electrical properties responses.

On a more general level, a detection decision, i.e., determining whether there is an analyte, for example virus, or not present in a test sample is in embodiments carried out by comparing the discrepancy between the measured responses of one or more of electrical and/or optical parameters at different applied electric fields. This discrepancy can be measured in terms of nonlinearity or differences in measured parameters values. In embodiments algorithms are implemented in accordance with such methods to make the detection decision automatically using software or developed programs possibly involving artificial intelligence. The nonlinearity can be expressed in terms of extracted single or multi parameters and their response profiles over time variations be observed manually or automatically.

Determining the quantification is in embodiments carried out with the help of calibration curves that for example are generated with known concentration of analyte or analyte load, for example virus. In other embodiments, quantification is determined from the differences of capacitance versus voltage profiles by subtracting the capacitance per voltage values at an applied low magnitude electric field from the capacitance per voltage values at an applied high magnitude electric field, and as in embodiments processing this difference signal using semiconductor theory to extract single or multi parameters to determine the analyte load, for example virus load, and a quantification of the analyte, for example virus, in a test sample.

Determining identification of analytes, for example coronavirus, is in embodiments made based on single or multi figure of merits extracted from the single or multi parameters used in quantifications.

An embodiment of a more specific example of a method of detecting and quantifying coronavirus in a specimen from a patient, wherein the specimen being accommodated in a suspension medium, comprises: apportioning the suspended specimen into a first, a second and a third test sample; arranging said first test sample to contain purely the suspended specimen; adding ACE2 antibodies to said second test sample; adding NC antibodies to said third test sample; applying an electric field with a first magnitude and with a second magnitude over said first, second and third test samples for a selected period of time, said second magnitude being higher than said first magnitude; measuring one or more electrical properties of said test samples in response to said applied electric field for said first magnitude and for said second magnitude over said period of time; identifying characteristics of said electrical properties responses; determining the presence, the quantity and/or the identification of coronavirus dependent on differences in characteristics of said electrical properties responses to said first magnitude and to said second magnitude of the applied electric field.

FURTHER EXEMPLIFYING EMBODIMENTS

A first exemplifying embodiment procedure comprises:

1. Loading a specimen of a COVID sample as a test sample into a test sample container and placing the test sample container in the test sample holder of a testing apparatus.

2. Applying a first magnitude electric field induced by applying a first voltage over the test sample container for a selected period of time, the first magnitude electric field preferably being a low magnitude electric field induced by a low voltage for example in the range of −0.5 to 0.5 volts. A first low magnitude electric field induced by a voltage of 0 volts, i.e., no actual electric field applied over the test sample is employed in exemplifying embodiments.

3. Measuring electrical properties responses in the form of Capacitance per applied low voltage at a frequency (f0).

4. Applying a second magnitude electric field induced by applying a second voltage over the test sample container for a selected time period, the second magnitude electric field preferably being a high magnitude electric field being induced by a high voltage for example ranging from 0.5 to 3 volts.

5. Re-measuring the electrical properties responses in the form of Capacitance per applied voltage at the same frequency (f0).

6. Optionally measuring optical properties responses in the form of light intensities for the test sample simultaneously with the measuring of the electrical properties responses.

7. Determining, based on the electrical properties response parameters and/or optionally also based on the optical properties response parameters, detection, quantification and/or identification of coronavirus in the test sample.

Variants of this embodiment are conducted: with or without added reagent for example in the form of antibodies such as ACE-2 antibodies or NC antibodies; with DC voltage applied or with pulsating AC voltages applied.

This embodiment is exemplified by application on coronavirus, and may be used on other analytes as well.

A second exemplifying embodiment procedure devised for parallel processing of two samples comprises:

1. Loading a specimen of a COVID sample as a first test sample into a first test sample container (container 1) and placing the first test sample container in the test sample holder of a testing apparatus being configured for testing a plurality of test sample containers.

2. Loading a specimen of the COVID sample as a second test sample into a second test sample container (container 2) and placing the second test sample container in the test sample holder of said testing apparatus.

3. Applying a first magnitude electric field induced by applying a first voltage over the first test sample container (container 1) for a selected period of time, the first magnitude electric field preferably being a low magnitude electric field induced by a low voltage for example in the range of −0.5 to 0.5 volts. A first low magnitude electric field induced by a voltage of 0 volts, i.e., no actual electric field applied over the test sample is employed in exemplifying embodiments.

4. Measuring electrical properties responses of the first test sample container (container 1) in the form of Capacitance per applied low voltage at a frequency (f0).

5. Applying a second magnitude electric field induced by applying a second voltage over the second test sample (container 2) for a selected time period, the second magnitude electric field preferably being a high magnitude electric field being induced by a high voltage for example ranging from 0.5 to 3 volts.

6. Measuring the electrical properties responses of the second test sample container (container 2) in the form of Capacitance per applied voltage at the same frequency (f0).

7. Optionally measuring optical properties responses of the first test sample (container 1) in the form of light intensities simultaneously with the measuring of the electrical properties responses of said first test sample (container 1).

8. Optionally measuring optical properties responses of the second test sample (container 2) in the form of light intensities simultaneously with the measuring of the electrical properties responses of said second test sample (container 2).

7. Determining, based on the electrical properties response parameters and/or optionally also based on the optical properties response parameters, detection, quantification and/or identification of coronavirus in the first test sample (container 1) and the second test sample (container 2).

Variants of this embodiment are conducted: with or without added reagent for example in the form of antibodies such as ACE-2 antibodies or NC antibodies; with DC voltage applied or with pulsating AC voltages applied.

This embodiment is exemplified by application on coronavirus, and may be used on other analytes as well.

A third exemplifying embodiment procedure devised for parallel processing of a plurality of samples simultaneously for the purpose of reducing testing time comprises:

1. Loading a specimen of a COVID sample as a first test sample into a first test sample container (container 1) and placing the first test sample container in the test sample holder of a testing apparatus being configured for testing a plurality of test sample containers.

2. Loading a specimen of the COVID sample as a second test sample into a second test sample container (container 2) and placing the second test sample container in the test sample holder of said testing apparatus.

3. Loading a specimen of the COVID sample with an added reagent for example in the form of antibodies, that may be a single type antibodies or a mix of antibodies as a third test sample into a third test sample container (container 3) and placing the third test sample container in the test sample holder of said testing apparatus.

4. Loading a specimen of the COVID sample with an added reagent for example in the form of antibodies, that may be a single type antibodies or a mix of antibodies as a fourth test sample into a fourth test sample container (container 4) and placing the fourth test sample container in the test sample holder of said testing apparatus.

5. Applying a first magnitude electric field induced by applying a first voltage over the first test sample container (container 1) for a selected period of time, the first magnitude electric field preferably being a low magnitude electric field induced by a low voltage for example in the range of −0.5 to 0.5 volts. A first low magnitude electric field induced by a voltage of 0 volts, i.e., no actual electric field applied over the test sample is employed in exemplifying embodiments.

6. Measuring electrical properties responses of the first test sample container (container 1) in the form of Capacitance per applied low voltage at a frequency (f0).

7. Applying a second magnitude electric field induced by applying a second voltage over the second test sample (container 2) for a selected time period, the second magnitude electric field preferably being a high magnitude electric field being induced by a high voltage for example ranging from 0.5 to 3 volts.

8. Measuring the electrical properties responses of the second test sample container (container 2) in the form of Capacitance per applied voltage at the same frequency (f0).

9. Applying a first magnitude electric field induced by applying a first voltage over the third test sample container (container 3) for a selected period of time, preferably a low voltage in similarity to point 5.

10. Measuring electrical properties responses of the third test sample container (container 3) in the form of Capacitance per applied low voltage at a frequency (f0).

11. Applying a second magnitude electric field induced by applying a second voltage over the fourth test sample (container 4) for a selected time period, preferably a high voltage in similarity to point 7.

12. Measuring electrical properties responses of the fourth test sample container (container 4) in the form of Capacitance per applied high voltage at a frequency (f0).

13. Optionally measuring optical properties responses of the first test sample (container 1) in the form of light intensities simultaneously with the measuring of the electrical properties responses of said first test sample (container 1).

14. Optionally measuring optical properties responses of the second test sample (container 2) in the form of light intensities simultaneously with the measuring of the electrical properties responses of said second test sample (container 2).

15. Optionally measuring optical properties responses of the third test sample (container 3) in the form of light intensities simultaneously with the measuring of the electrical properties responses of said third test sample (container 3).

16. Optionally measuring optical properties responses of the fourth test sample (container 4) in the form of light intensities simultaneously with the measuring of the electrical properties responses of said fourth test sample (container 4).

17. Determining, based on the electrical properties response parameters and/or optionally also based on the optical properties response parameters, detection, quantification and/or identification of coronavirus in the first test sample (container 1) and the second test sample (container 2).

Variants of this embodiment are conducted with DC voltage applied or with pulsating AC voltages applied.

This embodiment is exemplified by application on coronavirus, and may be used on other analytes as well.

In a fourth exemplifying embodiment procedure the example procedure of the second exemplifying embodiments as described above is generalized to a plurality of 2 to N test samples in 2 to test sample containers, where N is an integer 3 and upwards. Specifically configured test sample containers and a test sample holders are devised for simultaneous parallel processing of large numbers of multiple samples in order to reduce testing time.

Variants of this embodiment are conducted: with or without added reagent for example in the form of antibodies such as ACE-2 antibodies or NC antibodies; with DC voltage applied or with pulsating AC voltages applied.

This embodiment is exemplified by application on coronavirus, and may be used on other analytes as well.

Electrical Properties Response Examples of Embodiments

Examples of electrical properties response characteristics of embodiments are shown in FIG. 8-FIG. 11. These examples are obtained in embodiments applied on coronavirus (COVID-19).

Figure 8:
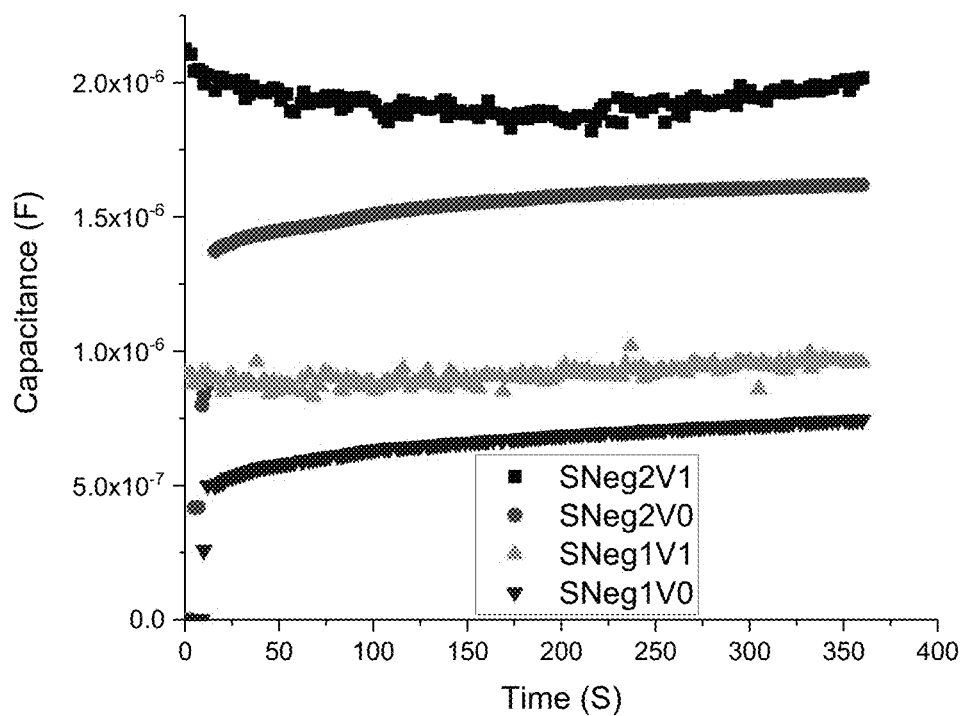
Figure 9:
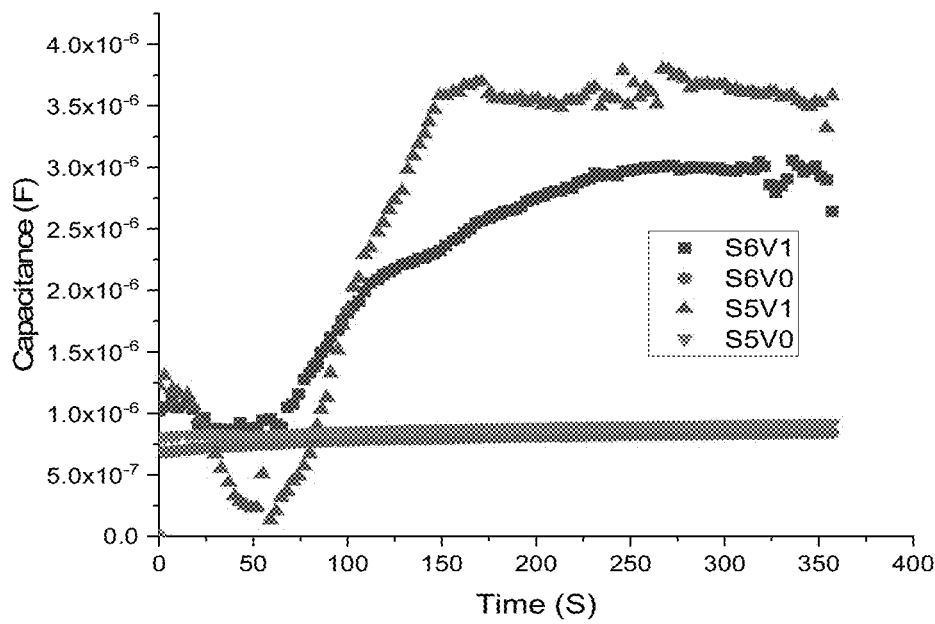

In a first set of examples, FIG. 8 and FIG. 9 depict diagrams that represent electrical properties responses in the form of the capacitance versus time profiles at two different levels of applied voltages, thus inducing a first and a second magnitude electric fields over the test samples, for two negative and two positive test samples at a frequency of 10 Hz, respectively, over a period of time S of about 360 seconds.

The diagram of FIG. 8 depicts the capacitance versus time profiles of two negative test samples at zero and at 1 volt, respectively. In FIG. 8 the capacitance response of: a first negative test sample at zero volt applied, SNeg1V0, is plotted as a series of blue upside down pyramids; the first negative test sample at 1 volt applied, SNeg1V1 is plotted as a series of green pyramids; a second negative test sample at zero volt applied, SNeg2V0, is plotted as a series of red dots; and the second negative test sample at 1 volt applied, SNeg2V1 is plotted as a series of black squares.

The diagram of FIG. 9 depicts the capacitance versus time profiles of two positive test samples at zero and at 1 volt, respectively. In FIG. 9 the capacitance response of: a first positive test sample at zero volt applied, S5V0, is plotted as a series of green upside down pyramids; the first positive test sample at 1 volt applied, S5V1, is plotted as a series of blue pyramids; a second positive test sample at zero volt applied, S6V0, is plotted as a series of red dots; and the second positive test sample at 1 volt applied, S6V1, is plotted as a series of black squares.

Comparing the plotted capacitance responses for the negative test samples in FIG. 8 and the positive test samples in FIG. 9 yield that the capacitance profiles of positive test samples exhibit non-linearity with higher capacitance values, whereas the negative test samples exhibit generally flat profiles. The capacitance profiles of the positive test samples also exhibit a rise in capacitance at applied high voltage of 1 volt after a certain time period that is not observed in the capacitance profiles of the negative test samples. The degree of nonlinearity and the differences between zero voltage profiles and high voltage profiles are in embodiments correlated with the concentration of the virus.

Figure 10:
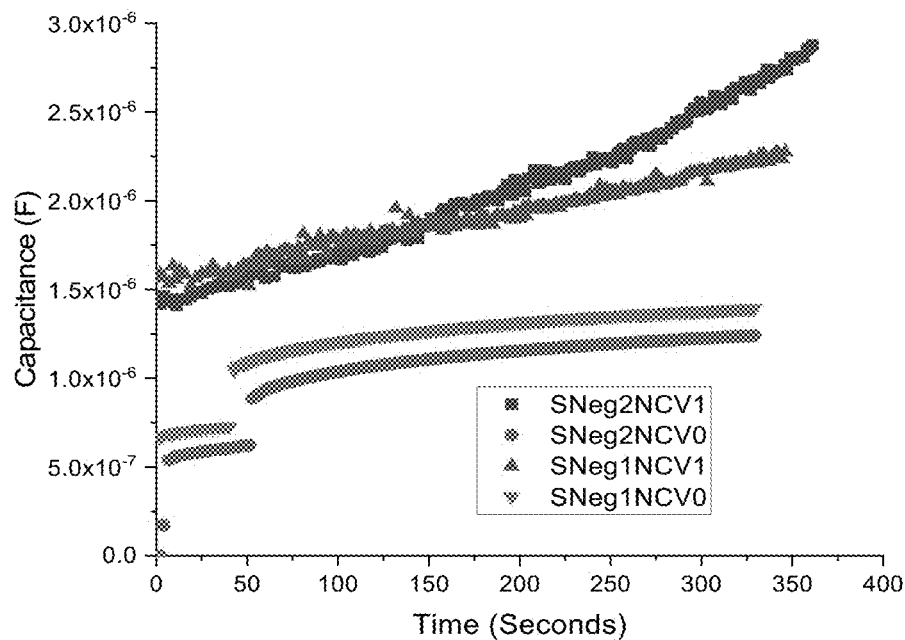
Figure 11:
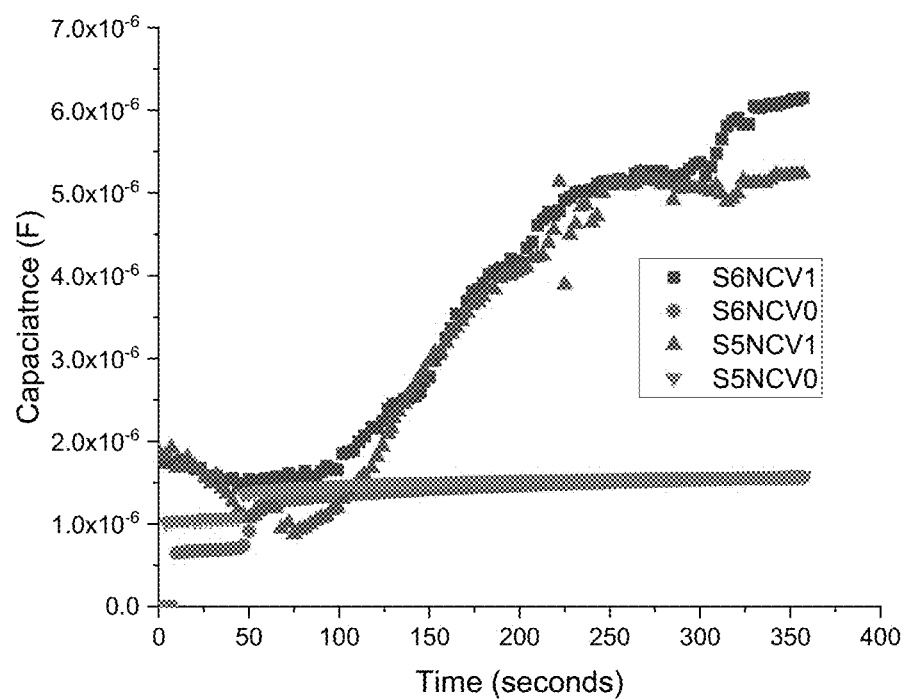

In another set of examples, FIG. 10 and FIG. 11 depict diagrams that represent electrical properties responses in the form of the capacitance versus time profiles at two different levels of applied voltages, thus inducing a first and a second magnitude electric fields over the test samples, for two negative and two positive test samples with added reagent in the form of NC antibodies at a frequency of 10 Hz, respectively, over a period of time S of about 360 seconds.

The diagram of FIG. 10 depicts the capacitance versus time profiles of two negative test samples with added NC antibodies at zero and at 1 volt, respectively. In FIG. 10 the capacitance response of: a first negative test sample at zero volt applied, SNeg1NCV0, is plotted as a series of green upside down pyramids; the first negative test sample at 1 volt applied, SNeg1NCV1 is plotted as a series of blue pyramids; a second negative test sample at zero volt applied, SNeg2NCV0, is plotted as a series of red dots; and the second negative test sample at 1 volt applied, SNeg2NCV1 is plotted as a series of black squares.

The diagram of FIG. 11 depicts the capacitance versus time profiles of two positive test samples with added NC antibodies at zero and at 1 volt, respectively. In FIG. 11 the capacitance response of: a first positive test sample at zero volt applied, S5NCV0, is plotted as a series of green upside down pyramids; the first positive test sample at 1 volt applied, S5NCV1, is plotted as a series of blue pyramids; a second positive test sample at zero volt applied, S6NCV0, is plotted as a series of red dots; and the second positive test sample at 1 volt applied, S6NCV1, is plotted as a series of black squares.

Comparing the plotted capacitance responses for the negative test samples in FIG. 10 and the positive test samples in FIG. 11 yield, in similarity with the previous set of examples, that the capacitance profiles of positive test samples exhibit non-linearity with higher capacitance values, whereas the negative test samples exhibit generally flat linearly rising profiles. The capacitance profiles of the positive test samples also exhibit a rise in capacitance at applied high voltage of 1 volt after a certain time period that is not observed in the capacitance profiles of the negative test samples. As with the previous example, the degree of nonlinearity and the differences between zero voltage profiles and high voltage profiles are in embodiments correlated with the concentration of the virus.

Figure 12:
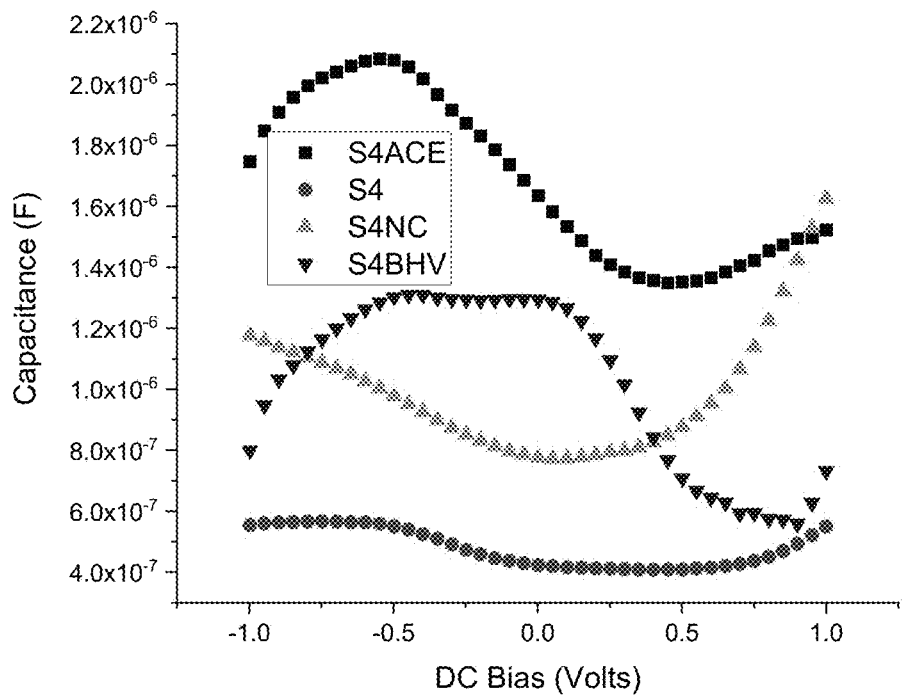

In yet another set of examples, FIG. 12 depicts a diagram that represents electrical properties responses in the form of the capacitance versus DC bias voltage profiles for a positive test sample with specimen only before and after application of a high voltage, for a positive test sample with added reagent of NC antibodies after application if high voltage and for a positive test sample with added reagent of ACE-2 antibodies after application of high voltage at a frequency of 10 Hz, respectively, over a range of DC bias voltage from −1.0 volt to 1.0 volt. In FIG. 12 the capacitance versus DC bias voltage response of: a first positive test sample with specimen only before applied high voltage, S4BHV, is plotted as a series of blue upside down pyramids; a second positive test sample with specimen and added NC antibodies after applied high voltage, S4NC, is plotted as a series of green pyramids; a third positive test sample with specimen only after applied high voltage, S4, is plotted as a series of red dots; and a fourth positive test sample with specimen and added ACE-2 antibodies, S4ACE, is plotted as a series of black squares. The response profiles of the respective test samples have their individual characteristics, and in embodiments such profiles are further processed to be used in determining the detection, quantification and identification of coronavirus.

Further examples of response profiles in embodiments comprising measurement of optical response characteristics are illustrated in FIGS. 13A to 13C and FIGS. 14A to 14B. The optical response characteristics in the form of light intensity have been measured for positive and negative test samples, with and without added reagent in the form of ACE-2 antibodies and NC antibodies/Anti-N antibodies, respectively, at two different bias voltages over time. From time 0 to 250 seconds the applied bias voltage is zero and from time 251 to 500 seconds the applied voltage is high, e.g., 1 volt.

Figure 13A:
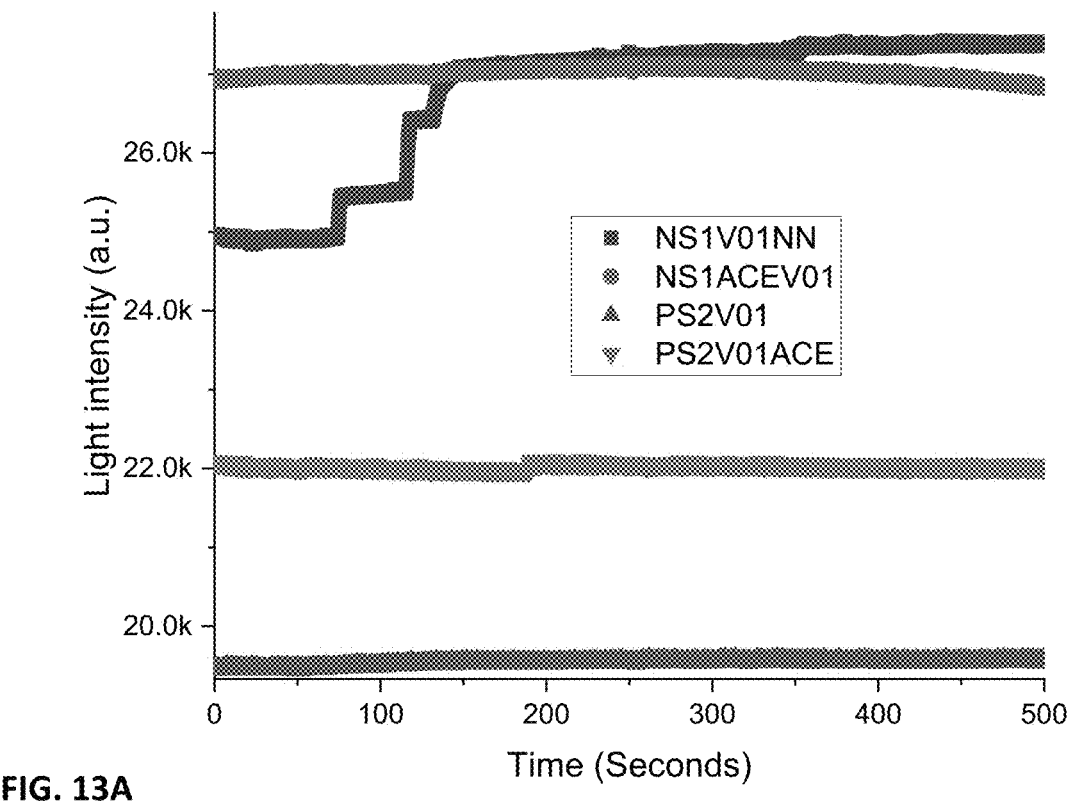

In FIG. 13A the light intensity response versus time of: a first positive test sample with specimen only, PSV01, is plotted as a series of blue pyramids; a second positive test sample with added ACE-2 antibodies, PS2V01ACE, is plotted with green upside down pyramids; a first negative test sample with specimen only, NS1V01NN, is plotted with a series of black squares; and a second negative test sample with added ACE-2 antibodies, NS1ACEV01, is plotted with a series of red dots.

Figure 13B:
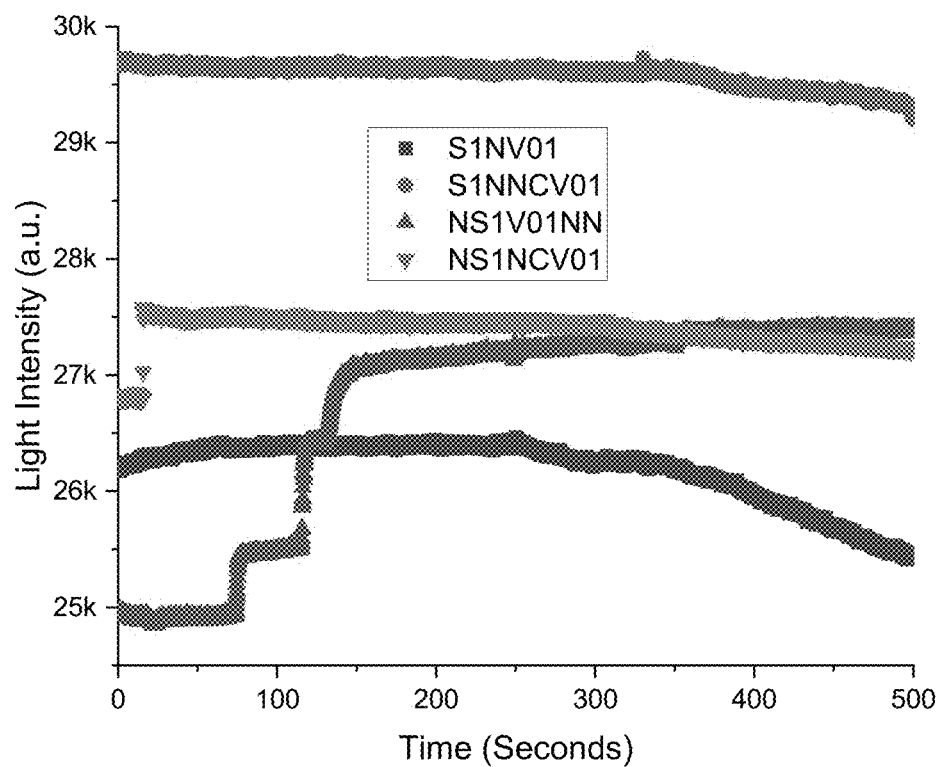

Similarly, in FIG. 13B the light intensity responses versus time of: a first negative test sample with specimen only, NS1V01NN, is plotted with a series of blue pyramids; a second negative test sample with added NC antibodies, NS1NCV01, is plotted with green upside down pyramids; a first positive test sample with specimen only, S1NV01, is plotted with a series of black squares; and a second positive test sample with added NC antibodies, S1NNCV01, is plotted with a series of red dots.

Figure 13C:
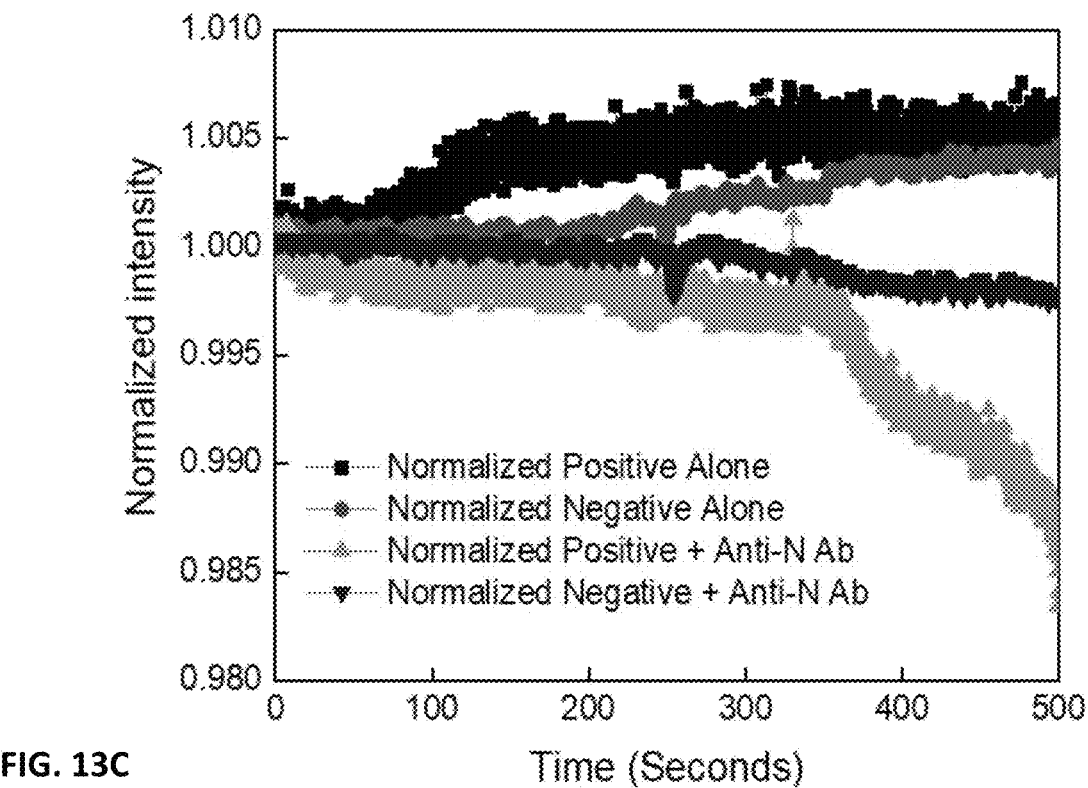

FIG. 13C shows, in a diagram with normalized parameter values, the light intensity responses versus time wherein: a first normalized positive sample with specimen alone, i.e. only specimen and no added reagent, is plotted with a series of black squares; a first normalized negative sample with specimen alone, i.e. only specimen and no added reagent, is plotted with a series of red dots; a second normalized positive sample with added anti-N antibodies is plotted with a series of green pyramids; and a second negative sample with added anti-N antibodies is plotted with a series of upside down pyramids.

In an embodiment of a measurement approach, as e.g., illustrated in FIG. 13C, comprises and is preferably started with a stage of normalizing the measured light intensities, each to its corresponding y-intercept. Such a normalization is conducted in order to compensate for effects due to characteristics of a sample container, for example in the form of a cuvette, electrodes and cable connections that influence the light intensity of light passing through a sample, to unify the scales and to allow determination of the variations clearly.

In the example of normalized curves of light intensities shown in the diagram of FIG. 13C it is clear that the negative sample with and without added reagent, here in the form of anti-N antibodies, exhibits more linear responses than the positive samples. The normalized curves also confirm interactions between antibodies and the coronavirus in the positive sample (see the green curve), which represents the normalized positive sample with anti-N antibodies. For these exemplifying curves, the slopes of the entire time intervals before applying bias voltage were measured. The slopes of the negative and positive samples in FIG. 13C were extracted through the process of linear regression during a bias of 0 volt and of 1 volt applied voltage. In embodiments, it is preferable to have minimum periods of 100 seconds to have a sufficient safety margin to be sure that an interaction has occurred that would be reflected in the measured response characteristics profile.

To illustrate an analysis of the behavior of the samples further, the slopes of the corresponding sample normalized profiles were extracted and have been summarized in Table 1 from ten negative COVID-19(−) and ten positive COVID-19(+) individuals. The table shows the rate of change in the normalized measured light intensity of nasal swab samples from ten negative COVID-19 (−) and ten positive COVID (+) samples.

TABLE 1

Rate of Change in the Normalized Measured Light Intensity of Nasal Swab Samples from COVID-19 (−) and COVID (+) Samples.

| Sample | Slope @ zero | Slope @ 1 V | Variation | Figure of Merit (FOM) |
|---|---|---|---|---|
| Positive alone | 2.25E−06 | 3.95E−08 | 2.21E−06 | |
| Negative alone | 2.29E−07 | 1.01E−06 | −7.82E−07 | |
| Positive + Anti-N Ab | −6.36E−07 | −5.92E−06 | 5.29E−06 | 2.07E+00 |
| Negative + Anti-N Ab | −2.02E−07 | −9.54E−07 | 7.51E−07 | 8.02E−01 |

Figure 14A:
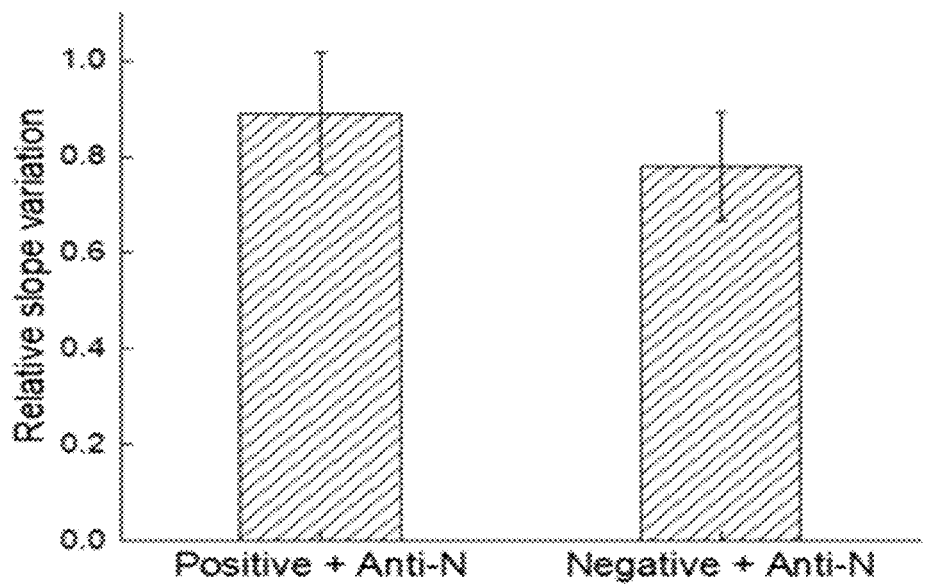
Figure 14B:
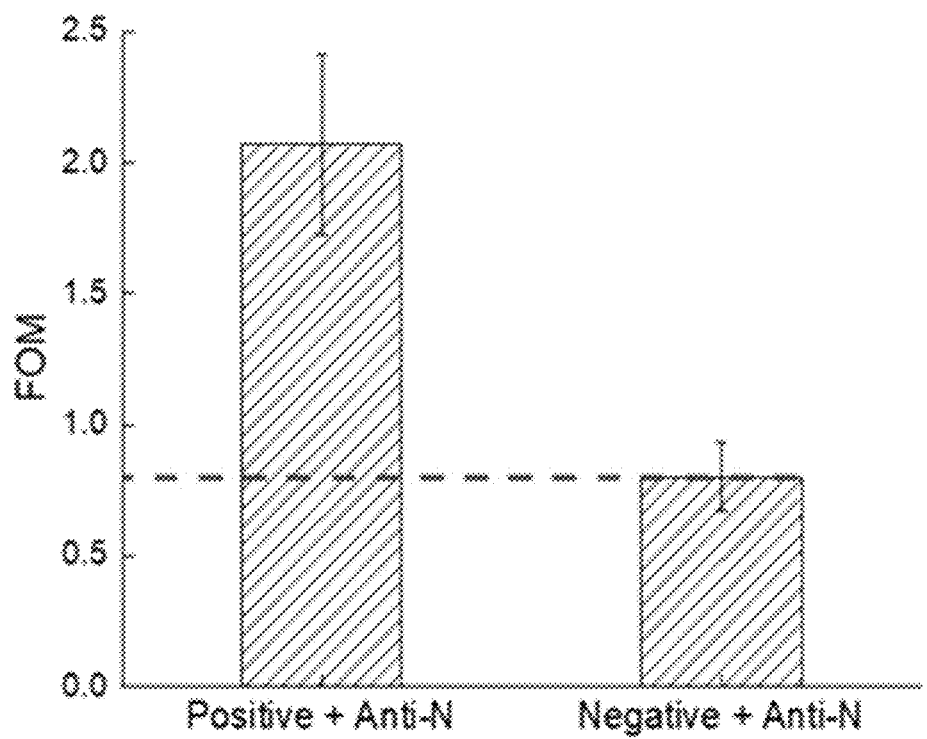

FIGS. 14A and 14B show diagrams that illustrates slope variation observed in the test samples.

In FIG. 14A shows statistics of the slope variation the extracted slopes for the negative and positive samples tested in the presence of the anti-N antibodies. The diagram depicts the relative difference in the measured profile slopes with and without voltage bias. This diagram reveals that the absolute extracted slopes for the positive samples in the presence of anti-N antibodies was approximately two times higher than the extracted slopes for the negative samples in the presence of the anti-N antibodies. Therefore, in embodiments, the slope variation above 10% is set as the threshold of detection of a COVID-19 patient with low accuracy.

Embodiments configured for higher accuracy detection, comprises applying the following Figure of Merit (FOM) in accordance with the relationship:

$$FOM = |-(SA-S)_{\_1V}| / |-(SA-S)_{\_0V}| \quad \text{(FOM relation)}$$

where SA and S are the samples with reagent, e.g., antibody and the same sample alone, i.e., specimen without any added reagent, respectively.

The FOM represents the relative variation of the sample with and without antibody at two different voltages. The corresponding extracted FOM is listed in the last column of Table 1. As illustrated in FIG. 14B, the accuracy of prediction was improved dramatically. For example, based on the results obtained from ten negative and ten positive nasal swab samples each, an FOM of above 1 should be able to successfully predict the COVID-19 status of a patient with 100% accuracy using embodiments with this approach. For rapid and quick detection, the nasal swab can be split into four specimens and the four required tests, i.e., test sample at zero and one volt, test sample with anti-N antibodies at zero and one volts, can be run simultaneously to collect the corresponding optical profiles for 100 seconds. The data can then be processed to extract the slopes and the FOM to have the results.

The optical response profiles of the respective test samples have their individual characteristics, and in embodiments such optical response profiles are further processed to be used in determining the detection, quantification and identification of coronavirus.

Figure 15:
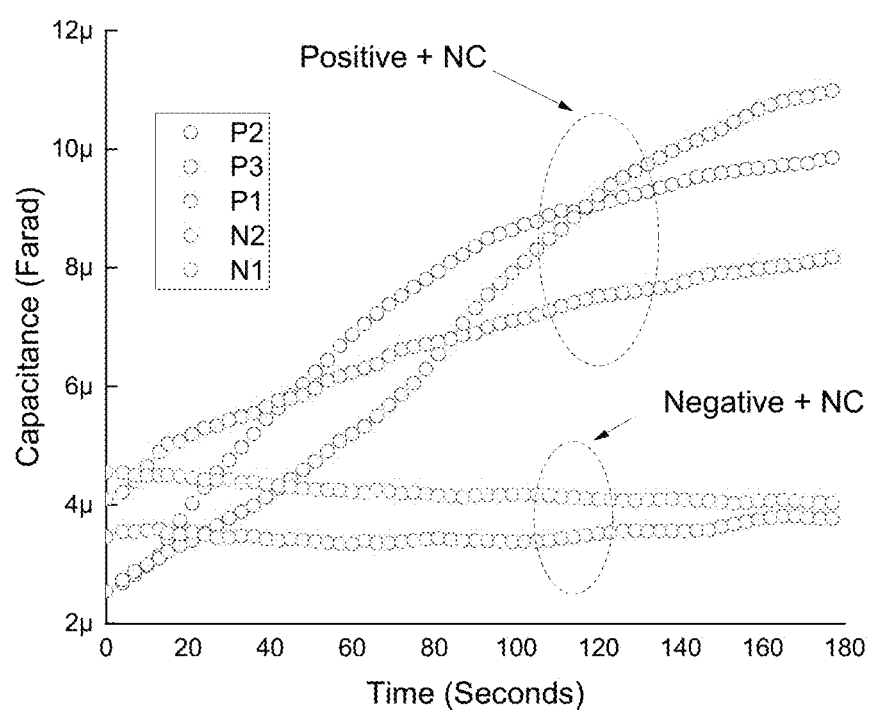

In a further example, with AC voltage applied over test samples, capacitance versus time responses appear as illustrated in FIG. 15. FIG. 15 shows a diagram of capacitance versus time responses for positive and negative samples with added reagent in the form of NC antibodies at frequency of 10 Hz and oscillation amplitude of 1000 mV. In FIG. 15 the capacitance versus time response of: a first negative test sample N1 is plotted with a series of lilac circles; a second negative test sample N2 is plotted with a series of green circles; a first positive test sample P1 is plotted with a series of blue circles; a second positive test sample P2 is plotted with a series of black circles; and a third positive test sample P3 is plotted with a series of red circles. The response profiles of the respective negative and positive test samples have their characteristics, and in embodiments such profiles are further processed to be used in determining the detection, quantification and identification of coronavirus.

FURTHER MEASUREMENT EXAMPLES AND EMBODIMENTS

In a measurement series in one embodiment, a testing apparatus as described above was used first to measure the viral transport medium (VTM) with and without the anti-N antibodies. The corresponding measured electrical current versus time as well as capacitance versus time with the application of one volt electrical bias over the test sample is shown in FIG. 16 and FIG. 17.

Figure 16:
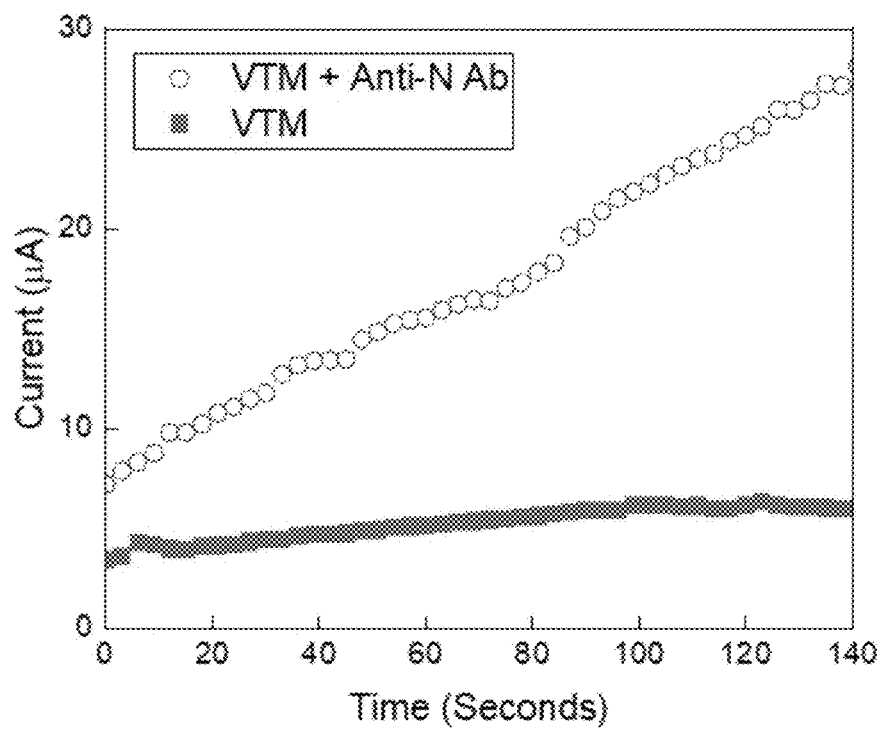
Figure 17:
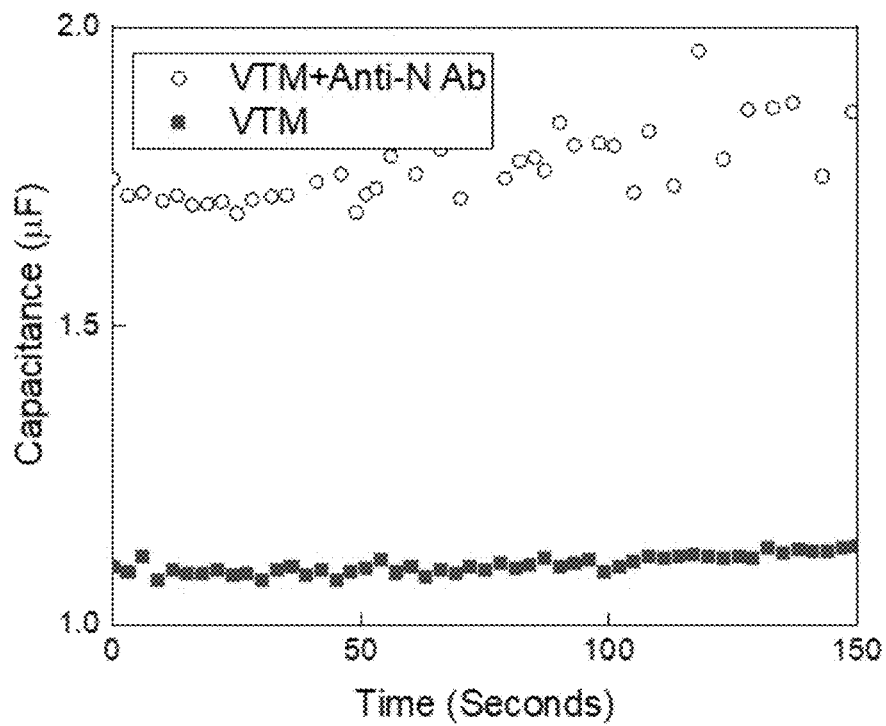

FIG. 16 and FIG. 17 show diagrams of measured electrical response profiles for a suspension medium such as a viral transport medium VTM buffer with and without anti-N antibodies (also called NC antibodies) at an applied bias voltage of 1 volt over a period of time of 0 to 140/150 seconds. The volume of the test sample with a nasal swab is 100 µL and the same volume of anti-N antibodies where the concentration of anti-N antibodies is 1 µg/mL. FIG. 16 shows current versus time profiles and FIG. 17 shows corresponding capacitance versus time profiles for a VTM buffer, where the VTM buffer without antibodies, VTM, is plotted as a series of red squares and the VTM buffer with antibodies, VTM+Anti-N Ab, is plotted as a series if circles, in the respective diagrams.

As illustrated in FIG. 16, the VTM individual profile exhibits a substantially straight line with slope of 25 nano amperes per second, meanwhile the VTM mixed with Anti-N Ab exhibits a slope of 140 nano amperes per second. With the application of a bias voltage, the VTM alone shows stable behavior, the measured current did not vary significantly with time. Meanwhile for the mixed VTM with antibodies, the electrical current still exhibits linear profile but with steep variation with time.

For further understanding this, the corresponding electrical capacitance profiles have been measured as illustrated in FIG. 17. The value of the electrical capacitance goes up when antibodies are added. The antibodies can be considered as impurities that not only contribute to the raise in electrical capacitance but also disturb the stability of the profile when compared with the VTM response alone. The increment in the capacitance value is due to the fact that Anti-N Ab get electrically polarized due to their capability to hold electric charge. The disturbance is due to the interactions between the Anti-N Ab and the suspension VTM medium. The suspended Anti-N bodies exhibit Brownian motion, which cause trapping. This trapping is translated into fluctuations in the capacitance versus time profile.

In a measurement series in another embodiment, similarly a testing apparatus as described above was used to measure negative and positive test samples with and without the anti-N antibodies. The measured capacitance versus time responses as well as detected binding events for negative and positive test samples are shown in FIG. 16 and FIG. 17. The negative and positive test samples had been confirmed by PCR testing.

Figure 18:
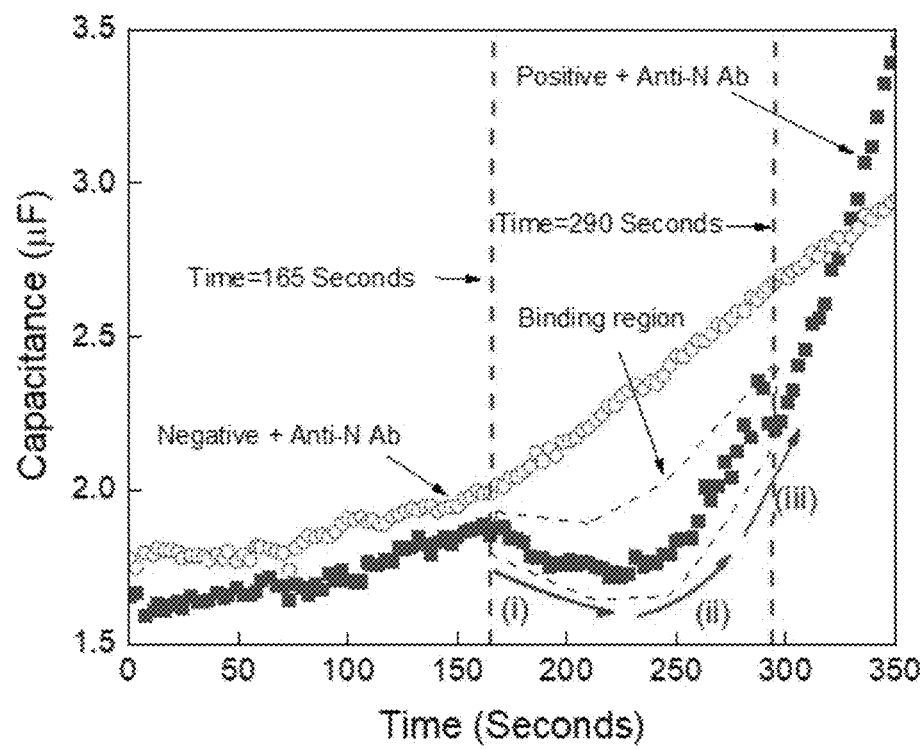
Figure 19:
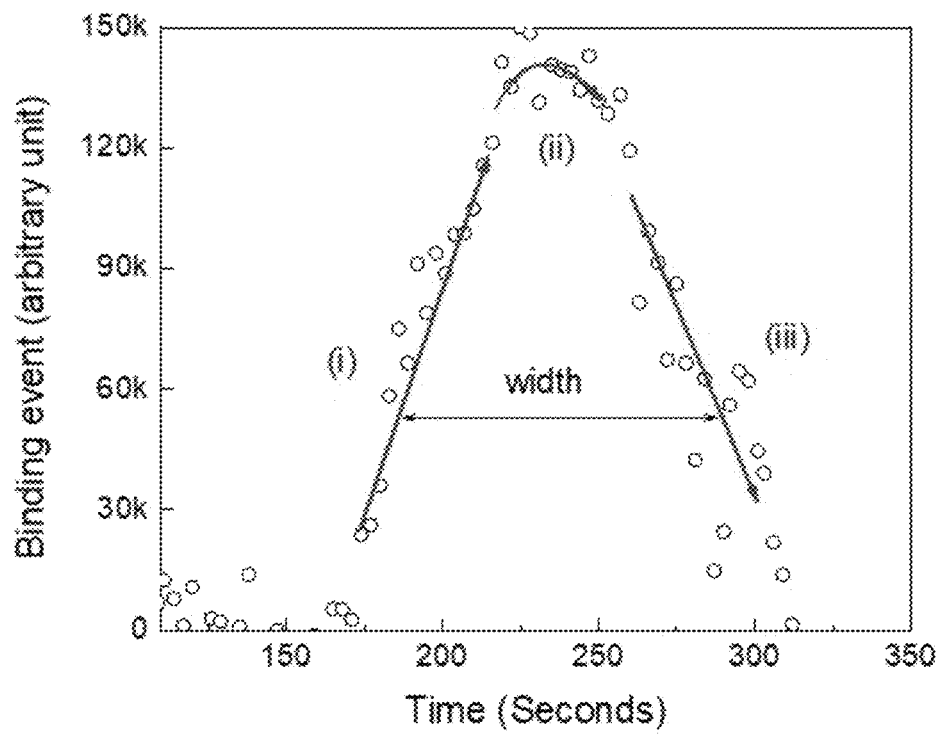

FIG. 18 and FIG. 19 show diagrams of negative and positive test sample measurements with the addition of antibodies (Anti-N Abs) at bias of 1 volt applied over the test sample for a period of time of 350 seconds. FIG. 18 shows measured capacitances versus time response profile wherein: a positive test sample with added antibodies, Positive+Anti-N Ab, is plotted as a series of black squares; a negative test sample with added antibodies, Negative+Anti-N Ab, is plotted as a series of red circles. FIG. 19 shows extracted binding event profile, wherein detected binding events (in an arbitrary unit) versus time is plotted as black circles.

Turning to the measured capacitances profiles displayed in FIG. 18. Specimen taken with nasal swabs were used to detect the presence of rhinovirus in patients using the anti-N antibody, an antibody against the structural gene of the virus as described above. A patient specimen from the nasal swab was preserved as a test sample in the viral transport media, the specimen consisting primarily of epithelial cells from the nasal cavity as well as any free virus that might be present in the nasal passage. Specimen taken with nasal swabs from individuals that were known to be free from rhinovirus infection were used as negative controls.

As illustrated in FIG. 18, the capacitance response profile of a negative test sample with added antibodies, Negative+Anti-N Ab, exhibits stable and smooth behavior substantially devoid of fluctuations. This response profile can be modelled as piecewise linear approximation consisting of two regions, where the first region extends from 0 to 165 seconds and the second region starts from 165 and extends to the end of the depicted time interval, here 350 seconds.

The response profile of the positive test sample with added antibodies, Positive+Anti-N Ab also exhibits stable and smooth behavior however with distinctly different characteristics. This response profile can be split into three regions: the first region extending from 0 to 165 seconds, the next region extending from 165 to 290 seconds and the third region extending from 290 to the end of the depicted time interval, here 350 seconds. The first and third regions both exhibit linear behavior. The middle region exhibits nonlinear behavior and is marked by the binding region as illustrated in FIG. 18. This nonlinearity is due to the binding events occurring between SARS-CoV-2 N proteins with anti-N Ab antibodies. It is noticeable that the first regions of both negative and positive profiles have closely similar behavior. With the application of voltage, an interface effective layer is formed because of the interaction between antibodies and the intercellular composition of the suspension itself. In fact, such a complex electrochemical polarization will enable the detection of SARS CoV-2 by monitoring the corresponding binding interaction.

The binding event profile can be extracted by detrending the positive profiles and consider its first region as its baseline. The binding event profile is depicted in FIG. 19. As described in FIG. 19, as the interaction starts, the corresponding binding profile ascends incrementally, as indicated by (i), due to the increase in occurring binding events. The peak indicated by (ii) occurs at the maximum occurrence of binding events between the antigen and the antibody. The profile then descends till the end as the binding events becomes less and no further interactions occur at the end, as illustrated by (iii). The narrower binding profile width reflects the speed of the interactions. This is mainly due to the physio-chemical properties of the proteins that relates to binding affinity in the contact surface area and incorporates the association process.

As explained above, under electrical bias i.e., with an electric field induced by an electric voltage over the cell, the cell opens up by the formation of pores in the cell membrane. The pores only stay open for the duration of the applied constant field or its time domain variation. The anti-N antibodies penetrate the cell through these pores and binds with the N protein of SARS-CoV-2 virus that is expressed during infection. The application of electric fields will modify the orientation of molecules and alter the ion transport rates, they can modify the quantum states of molecules, which lead to shifts in the energy levels. The infected cell physiology with and without the application of electric field is illustrated in FIG. 18 and FIG. 19, respectively. The cell is assumed to be suspended in the aqueous transport medium of a nasopharyngeal swab along with anti-N antibodies (anti-N Ab). The applied electric field will also affect the binding interactions by inducing dipoles of proteins due to the electrochemical polarization as illustrated in FIG. 5C. The binding of the antigens and antibodies possess net electric charges and their motion will have quite complex charge distributions, which make them sensitive to the presence of external electric fields. Furthermore, the application of the electric field will control the orientation of the created protein-protein dipoles as depicted in FIG. 5D, which will enhance binding signatures. Additionally, SARS-CoV-2 N protein has three distinct but highly conserved parts: the N-terminal RNA-binding domain (NTD) which is responsible for RNA binding via its distinct basic (positively charged) finger and palm regions: a C-terminal dimerization domain (CTD) which is responsible for oligomerization, and intrinsically disordered central Ser/Arg (SR)-rich linker which is responsible for linker for primary phosphorylation, respectively.

As revealed from the corresponding binding measured light intensity profiles, such interactions exhibit Gaussian-like peaks. In embodiments, Brownian motion is fitted with Gaussian function. The fitting parameters of the distributions provide a plurality of features of the binding interactions. In embodiments, this is used to provide a quantitative signature or characterization of a specific antigen binding to a specific antibody such as intrinsic specificity and binding rate.

Embodiments for Detection of Bindings and Interactions Between Analytes in a Sample On a general level, embodiments comprise a system and a method to detect and possibly monitor the possible binding or interactions between proteins and proteins, proteins and antibody, viruses and proteins, viruses and antibodies, cells and proteins, cells and antibodies. Also, virus-cell, or cell-cell interactions, or any interactions between any part of protein, antibody, virus, cell with any part of protein, antibody, virus, cell of the same or different kind.

Embodiments comprises a method of opto-electrical detection of the presence of possible bindings or interactions between analytes in a sample, comprising: exposing a sample to light from a light source; detecting light passing through the sample; applying an electrical field over the sample; determining the values of a selection of light scattering parameters for the light passing through the sample in response to the electrical field; and/or determining the values of a selection of electrical parameters, such as electrical scattering parameters, in response to the electrical field; determining the presence of bindings or interactions between analytes in the sample based on the values of the determined light scattering parameters and/or the determined values of the electrical parameters, for example electrical scattering parameters.

Further embodiments comprises a system of opto-electrical detection of the presence of possible bindings or interactions between analytes in a sample, comprising: a light source configured to emit or transfer natural or manmade light and to expose a sample with said light; an electric field device configured to apply a biasing electric field over the sample; a light detector configured to detect light passing through a said light exposed sample; an electric parameter detector configured to detect electric parameters. Such embodiments further comprise a processing device having code portions configured direct the processor to: determine the values of a selection of one or more light scattering parameters of the detected light passing through a said light exposed sample; determine the values of a selection of electrical parameters, for example electrical scattering parameters, in response to the electrical field, and to determine the presence of bindings or interactions between analytes in the sample based on the values of the determined light scattering parameters and the determined values of the electrical parameters, for example electrical scattering parameters.

An underlying mechanism for the concept of embodiments is that when two proteins bind or a molecular interaction takes place between them, due to this interaction, a possible form of kinetic energy is produced, perhaps emitted as a cloud. This kinetic energy can cause disturbances, such as altering the Brownian motion of the molecules which can change or alter light distribution on the surface of the sample or inside the sample. The generation of a cloud-like response due to the biochemical interaction should also disturb the light intensity distribution and accordingly the measured light intensities.

Further, the linear electro-optic effect is the change in the index of refraction that is proportional to the magnitude of an externally applied electric field. As mentioned herein. the electro-optic effect may also be non-linear, for example over a wider range. Hence, the measured light intensity varies with DC electric voltage. The DC bias will also change the current and capacitance as they depend on the applied voltage. This relationship/dependency may for example be converted to a chart that could be used for detection enhancement and further identification of the sample under test. For a specific virus type, the corresponding capacitance and light intensity at zero bias could also be used for further detection purposes.

In method embodiments, the presence of bindings or interactions between analytes in the sample is determined is determined based on a determined characteristic of the detected light scattering parameters, and/or electrical scattering parameters for specific values of the electric parameters. In system embodiments, the processing device comprises code portions configured to determine the presence of bindings or interactions in the sample based on determined characteristic of the detected light scattering parameters, and/or electrical scattering parameters, for specific values of the electric parameters.

Method embodiments comprises determining the presence of bindings or interactions between analytes in the sample by comparing the discrepancy between the measured responses at different applied electrical fields. In system embodiments, for this purpose the processing device comprises code portions configured to determine the presence of bindings or interactions between analytes in the sample by comparing the discrepancy between the measured responses at different applied electrical fields. Further method and system embodiments are configured to determine the presence of bindings or interactions between analytes in the sample by comparing the discrepancy between the measured responses at different applied electrical fields; and/or wherein the measured light intensity varies with DC electric voltage and/or values for the capacitance, for example, can be extracted from scattering parameters or impedance measurements or from determined relations between the parameters; and/or to determine information about the viral load and/or identifying the viral stage infection based on the voltage dependency. In embodiments of system, the processing device comprises code portions configured account for these possible features.

The emitted or transferred, manmade or natural, light from the light source may comprise the whole spectrum of wavelengths.

In such method and system embodiments the light detector is one or more of: an image-based system such as a camera, a spectrometer or any light-based detector, sensor or device that is capable to detect light intensity dependent or derivable parameter values. The method and system are in embodiments configured to detect light intensity and to determine light scattering parameters based on one or more of absorbance, reflectance, transmittance or any other type of light scattering, corresponding intensity or other parameter that is extractable or collectable by means of a light detector.

In method and system embodiments a selection of one or more light scattering parameters, for example intensities, are measured and possibly recorded over a time-period and/or mapped to a time domain. In system embodiments the processing device comprises code portions configured to measure and possibly record a selection of one or more light scattering parameters over a time-period and/or to map said parameters to a time domain.

In method and system embodiments the sample is loaded into a transparent holder or container allowing light to pass through the material without appreciable scattering of light and being configured for holding a sample, for example on or more of a plate, box, tube or any type of transparent paper or other transparent material. For this purpose, system embodiments, may further comprise a transparent holder or container allowing light to pass through the material without appreciable scattering of light and being configured for holding a sample, for example on or more of a plate, box, tube or any type of transparent paper or other transparent material.

A sample may, as in method embodiments, be tested in place in close connection with or in the proximity of the taking of the sample or be stored and/or transported for testing spatially and/or temporally remote from the taking of the sample. For this purpose, in system embodiments, the transparent holder or container is configured to store and/or transport a sample.

In method and system embodiments, the light source, a sample and the light detector are aligned such that measurement of light passing through the sample is enabled, for example by alignment in a straight line or other possible such alignment.

The electric field device comprises, in method and system embodiments, two electrodes configured or configurable at respective sides of a sample and being coupled or couplable to an electric energy source.

In method and system embodiments, the sample is added to a holder or container aligned with the light source and the light detector such that measurement of light passing through the sample is enabled; and measured responses in the form of the determined values of said selection of optical or electrical parameters, for example electrical scattering parameters, in response to the electrical field are collected to determine the presence of bindings or interactions between analytes in the sample. In system embodiments, the processing device comprises code portions configured to collect measured responses in the form of the determined values of said selection of optical or electrical parameters, for example electrical scattering parameters, in response to the electrical field for a sample that is added to a holder or container aligned with the light source and the light detector such that measurement of light passing through the sample is enabled.

Such method embodiments comprises steps, and in such system embodiments the processing device comprises code portions, configured to collect measured responses comprising one or more of: collecting directly measured light intensity; and/or collecting directly measured light intensity and establishing direct relationship with time; and/or processing direct measured data to extract parameters or a set of parameters and correlating said parameters with time to establish relationship with the presence of bindings or interactions between analytes in the sample.

Method and system embodiments further comprise determining the type of binding and/or interaction between analytes in the sample based on a relationship between the values of determined light scattering parameters and/or of determined electrical scattering parameters, and time, for example by direct judgement or by further processing. For this purpose, in system embodiments the processing device comprises code portions configured to determine the type of binding and/or interaction between analytes in the sample based on a relationship between the values of the determined light scattering parameters and time, and/or of the electrical scattering parameters and time.

In method and system embodiments, a mathematical relation for the determined parameters represents the process of bindings or interactions between analytes in the sample. For this purpose, in system embodiments, the processing device comprises code portions configured to apply a mathematical relation for the determined parameters to represent the process of bindings or interactions between analytes in the sample.

In examples of such method and system embodiments, with a mathematical relation between determined light scattering parameters, and/or electrical scattering parameters, and time for measured responses at selected applied electrical fields, binding and/or interaction between analytes is determined to be present if the relations shows nonlinearity and not to be present if the relation shows constant behaviour. In system embodiments, for this purpose, the processing device comprises code portions configured to, for a mathematical relation between determined light scattering parameters, and/or electrical scattering parameters, and time for measured responses at selected applied electrical fields, determine that binding and/or interaction between analytes is present if the relations show non nonlinearity and not present if the relation shows constant behaviour. In case of linear relationship that can be represented with a slope, the two kind of elements or more than two elements under investigation, their individual intensities should be measured and considered accordingly, in method and corresponding system embodiments. Further, in such embodiments the non-linearity may be expressed in terms of extracted single or multi-parameters, the non-linearity may be observed manually or automatically and the variation of response profiles of the one or more parameters may be detected over time. In corresponding system embodiments, the processing device comprises code portions configured to express the non-linearity in terms of extracted single or multi-parameters, to enable the non-linearity to be observed manually or automatically and to detect the variation of response profiles of the one or more parameters over time. Further method embodiments and corresponding system embodiments comprises or are configured to determining a mathematical relation for the light scattering parameters, and/or electrical scattering parameters, and values of the electric parameters to represent the presence and/or the process of one or more of said bindings or interactions between analytes in the sample based on the value of light scattering parameters for the detected light passing through the sample.

Method and system embodiments further comprise the use of and configuration with a chronoamperometry or a chronopotentiometry measurement method used to detect and/or monitor the presence and/or the process of one or more of said bindings or interactions.

In method and system embodiments the measured value, for example either current or voltage over time, can be used to explore the interaction. When an interaction occurs, the measured profile over time will increase or decrease in trend, depending upon the nature of the test samples, resulting in either an exponential growth or a decay behaviour. Furthermore, current voltage or capacitance voltage, impedance, or any other possible electrical-based measurements can also be considered. In method embodiments, the presence and/or the process of one or more of said bindings or interactions is determined, detected and/or monitored based on measurements of an electrical parameter, for example an electrical scattering parameter, for example a parameter based on one or more of the voltage, the current, the capacitance and/or the impedance over time in relation to a said applied electric field. For this purpose, in system embodiments, the processing device comprises code portions configured to determine, detect and/or monitor the presence and/or the process of one or more of said bindings or interactions based on measurements of an electrical parameter, for example one or more of the voltage, the current, the capacitance and/or the impedance over time in relation to a said applied electric field.

In further embodiments of method and system, low and high frequency scattering parameters or propagating waves, or any other possible form of measurements can also be considered. For this purpose, method and system embodiments, further comprise or are configured to measure and process parameter values based on low and high frequency scattering parameters or propagating waves.

In method embodiments, and in corresponding system embodiments comprising configured code portions, a characteristic of the determined light scattering parameters, and/or electrical scattering parameters, for specific values of the electric parameters is determined to represent the response of the determined light scattering parameters and/or electrical scattering parameters, due to the possible binding or interaction between one or more analytes in a sample, such as between proteins and proteins, proteins and antibody, viruses and proteins, viruses and antibodies, cells and proteins, cells and antibodies as well as virus-cell, or cell-cell interactions, or any interactions between any part of protein, antibody, virus, cell with any part of protein, antibody, virus, cell of the same or different kind.

Method and system embodiments are configured and/or used to monitor a vaccine or drug development process.

Method and system embodiments described herein may be configured for virus detection. A method embodiment is for this purpose used for virus detection and comprises collecting and processing electrical and optical responses individually or simultaneously to extract a set of parameters for detection, quantification and identification of virus. In a system embodiment for this purpose, the processing device comprises code portions configured to collecting and processing electrical and optical responses individually or simultaneously to extract a set of parameters for detection, quantification and identification of virus. In variants, such method and system embodiments comprise, or are configured to enable that, a virus cell is contacted by a selected antibody in a sample. Variants of such method and system embodiments are further adapted and used for detection of one or more of virus from the group SARS-CoV-2, SARS, MERS, influenza, respiratory syncytial virus (RSV), adenoviruses, or any other respiratory virus.

Further embodiments of the method and the system adapted for virus detection, further comprises or are configured to applying an electrical pulse over or through a sample containing analytes from a test subject and selected antibodies, thereby enabling electro-insertion of said antibodies into any virus cell present in the sample.

In method and system embodiments adapted for virus detection, a virus cell in a sample is suspended in an aqueous transport medium of a nasopharyngeal swab along with anti-N antibodies (anti-N).

Figure 21:
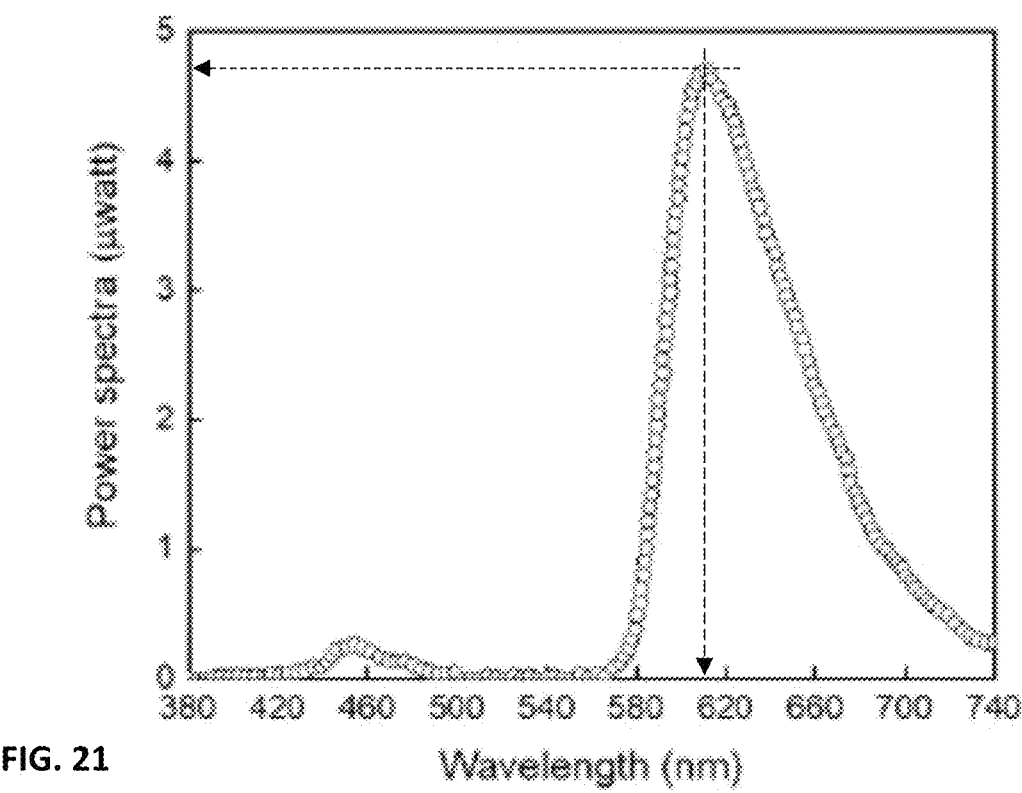

In further method and system embodiment adapted for virus detection, the method comprises steps, and the system the processing device comprises code portions, configured to determine a characteristic of the light scattering parameters, and/or electrical scattering parameters, for specific values of the electric parameters and to measure the viral nucleocapsid protein and anti-N antibody interactions in a sample to differentiate between SARS-CoV-2 negative and positive nasal swab samples.

Embodiments of the method and the system adapted for virus detection, further comprises a sample strip configured for collecting a sample of analytes from a test object, the sample strip comprising a portion coated with antibodies. In variants, the sample strip is coated with an antibody configured to bind or interact with of one or more of virus from the group SARS-CoV-2, SARS, MERS, influenza, respiratory syncytial virus (RSV), adenoviruses, or other respiratory virus.

In further method and system embodiments adapted for virus detection, the sample strip comprises an electrode coated thereon and configured to conduct current measurements directly.

Other method and system embodiments for opto-electric virus detection, further comprises a device for nasal sampling configured such that a sampling strip is attachable at a section of the nasal sampling device that is configured to be insertable in the nose of a human test object, the nasal sampling device comprising two electrodes configured to apply an electric field over a sample of analytes collected on a said sampling strip. In such system embodiments the nasal sampling device may further comprise an integrated light source and detector configured to expose the sample to light and to detect light passing through the sample.

Such integrated method and system embodiments are, in variants, configured such that when the presence of a binding or interaction between a virus and an antibody is detected in a sample from a patient, an indication signal is presented confirming that patient is infected with the tested virus. The indication signal for infection may for example be in the form of light, sound, text or image presented via a corresponding presentation device.

In embodiments of method and system, a sample is taken from bodily tissue or fluid, for example blood, breath, urine, nasal swabs, stool, in the system embodiments with a strip configured for this purpose.

These method and system embodiments are further described and explained by illustrating examples below.

Embodiments described herein, comprises a light-based method to detect SARS-CoV-2 and potentially disrupt its binding ability with its receptor, rendering the virus non-infectious by combining optical detection with electric current. The measured intensity of light is used to determine information about different cellular parameters in a sample under study with method embodiments. Light scattering and electrical scattering is correlated with cell/virus size and reflect the complexity of their exterior or interior structures. When light passes through a cell, the intensity is associated with the DNA/RNA content of the cells. The nuclei size, cell shape and the refractive index variation of cells contribute to light intensity in the cell. It is worth adding that the measured optical spectrum of light passing through a sample consists of many features that in embodiments is used to reveal and determine important information about the sample under test. Usually when the cell/tissue changes from a normal state to infectious, metabolic alterations and genetic modifications occur. This causes dramatic changes in their physiological, biochemical and morphological characteristics. Indeed, the metabolic differences between infected and normal cells leads to several variations in cellular parameters, such as their size. In this text, embodiments with an optical label-free detection method incorporating a smartphone light source and a portable mini spectrometer for SARS-CoV-2 detection are described. The detection of parameters reflecting light interactions with control and viral protein solutions in accordance with embodiments enables a quick decision regarding whether a sample under test is positive or negative, thus enabling SARS-CoV-2 detection in a rapid and label-free manner.

FIG. 2 illustrates a concept of optical detection in accordance with embodiments in an experimental design setup. FIG. 21 shows a graph of the smart phone power spectra versus wavelength and FIG. 22 shows an illustration of the spectrometer detection principle.

An experimental setup utilized to illustrate an exemplary embodiment presented in FIG. 20, incorporating a mini spectrometer and a smart mobile phone that was employed as a light source with the power spectrum depicted in FIG. 21. FIG. 20 thus shows an embodiment of an optical measurement setup 200 comprising a smart phone 202 with a built in LED-light as a light source 204. The light source 204 is, with the smart phone mounted on fixture 206, aligned with a spectrometer in the form of a mini-spectrometer 208 utilized to collect light waves passing through a sample 210 to be analysed. The sample 210 is kept in a container 212 in the form of a cuvette placed in a holder 214 that is mounted on a stand 216. The mini-spectrometer 208 is mounted in a spectrometer stand 218 with its electronics 220 coupled to a PC 222 or other control or processing device via control and/or data cable 224.

The graph in FIG. 21 shows the smart phone power spectra versus wavelength in an example of the experimental setup. In one example the measured optical power of the light beam exhibited a maximum power of approximate 35 µW at a wavelength of 623 nm, and in another example a maximum power of 47 µW at a wavelength of 615 nm as indicated in the graph of FIG. 21. In examples a mini-spectrometer C11708MA (Hamamatsu/Japan) was used to measure the light intensity as the light passes through test substances with spectral response ranging from 640 to 1010 nm. In those examples the wavelength reproducibility varied between −0.5 to 0.5 nm and a maximum of 20 nm full width at half maximum FWHM spectra, under constant light conditions. The sample under test was placed between the, in this example mobile, light source and the minispectrometer, as described and as shown in FIG. 20. The measurements were conducted with the room lights on. The distances between the light source, the spectrometer, and the sample holder were adjusted to eliminate any possible interference and to stabilize the spectrometer performance.

Figure 22:
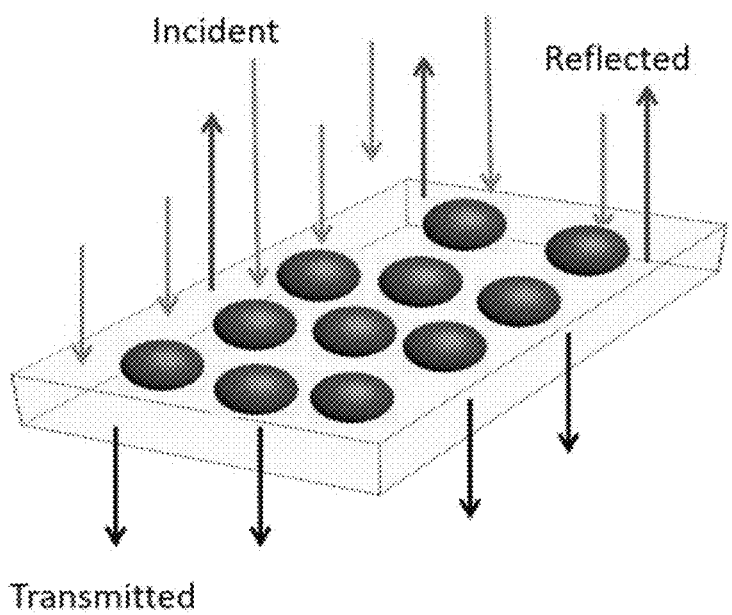

FIG. 22 illustrates the incident, reflected, and transmitted light intensities. The spectrometer was aligned with the light source and a sample cuvette accommodating the sample to achieve a straight path of light. The light intensities were linked through the Kirchhoff's Law of Radiation, which correlates the optical absorbance (A), transmittance (T), and reflection (R) along with the incident wave (I). In this text, the percentage of the relative change in light intensity ($\Delta I_r$) is introduced and defined to be the difference between the two measured peaks divided by their maximum peak times 100%.

An experimental setup in accordance with this embodiment may be used to characterize the two spike proteins subunits, S1 and S2 that are encoded by all coronaviruses and allow virus entry into susceptible cells, as illustrated in FIG. 3B. FIG. 23A shows an example of the optical responses for both spike proteins S1 and S2 along with their corresponding two blank samples. The measured optical intensity changed from 600 to 750 nm, within the light source spectrum measured earlier as illustrated in FIG. 21. The response of the blank samples was performed first, followed by the samples with the two protein suspensions, the responses to which were recorded individually.

The graphs in FIG. 23 show examples of optical measurements of samples with the spike protein subunits S1 and S2 in a microcentrifuge tube, wherein:

FIG. 23A shows measured light intensity over wavelength responses for spike proteins S1 and S2 at the highest concentration individually (S1B and S2B, respectively), along with their corresponding blanks.

FIG. 23B shows time domain measurements of the corresponding samples, the blank here an empty microcentrifuge tube shown to the upper left and the S1B sample with water to the upper right in grey circles, versus the blank again an empty microcentrifuge tube before S2B to the upper left and the S2B sample with water to the lower right in red circles, at a wavelength of 623 nm.

FIG. 23C shows measured optical responses for the mixed proteins versus time. Samples S1 and S2 were at 5000 copies per ml, S2C, S2D, S2E and S2F are the serial dilutions of S2B at 10-, 100-, 1,000- and 10,000-fold, respectively.

FIG. 23D shows relative change in light intensity per light path versus loaded mass.

All optical responses were measured at 623 nm. Light intensity was measured as arbitrary units (a.u).

FIG. 23A reveals that S2 exhibited a higher "back scattering" or absorbance than S1. The response of the two blank samples was quite comparable, showing the reproducibility of the results. Since the maximum difference between the blank and the two protein samples was observed at 623 nm, this wavelength was chosen for further experimentation to illustrate embodiments, which is also the wavelength at which the optical power of the smart phone is at its maximum.

Optimization of the Sample Reading Conditions

Embodiments comprise calibrating a system for opto-electric virus detection in order to correct for errors that may occur when samples are loaded into the sample holder, and the angle and position of a container for a sample for example in the form of a microcentrifuge tube changes which may affect the results obtained. To ensure that the results are reproducible, the measurements for the same samples may, as in embodiments, be conducted over different days. In such embodiments the setup may be standardized for example on each day since the position of the mobile phone, spectrometer and/or samples may vary. To overcome this caveat and have more consistence measurements without constant standardization, advantage may be made of the ability of the spectrometer to provide light intensity measurements over time. Hence, after placing the microcentrifuge tube into the holder, the measurement mode may be started and the corresponding "blank" recorded. Then the sample would be added after for example ~1.5 seconds, while keeping the measurement mode on. FIG. 23B illustrates the corresponding measurement profile for the buffer, in this case water. As would be expected, the blank exhibited the maximum measured light intensity, while the water sample showed lower light intensity than the blank. The shift in response time due to loading of the sample ranged between 1.5 to 2.3 seconds.

Test of the Spike Proteins Using the Experimental Set Up of Embodiments

In an example of conducting a test on the proof-of-principle of these embodiments for experimental design, initially a mixing experiment was conducted at a light wavelength of 623 nm. Towards this end, 250 μL of S1 protein solution was tested at the same maximum concentration at 5,000 copies/mL followed by addition of same amount of S2. FIG. 23C shows the light intensity (as arbitrary units, a.u.) with time as the protein samples were added to the container in a sequential manner. This was followed by addition of 250 μL of ten-fold serial dilutions of the S2 protein at equal time intervals to the S1+S2 samples. As can be seen from FIG. 23C, with the addition of the S2 protein, the light intensity increased. The biggest increase was observed with the concentrated S2 sample followed by its ten-fold dilution samples S2A, S2B, S2C, etc., until S2F addition as a 1:10,000 dilution had no extra effect on the increase in light intensity, indicated the limit of detection of the assay to be 5000 molecules per mL×250 1×1/10, 000=125 molecule per mL. These results indicated that ratio between the S1 and S2 protein concentration plays an important role in the light intensity levels measured. The ratio of S1 and S2 in the virus is the same since both come from the cleavage of S protein. However, the S1 subunit is expressed on the cell surface, while the S2 subunit is embedded in the lipid bilayer of the cell membrane; therefor S2 is less available at the cells surface, which should affect light intensity less than S1 despite equal ratios.

Table 2 below lists the extracted parameters at specific time points. The relative change in light intensity per light path length is a constructed parameter that should correlate with the loaded mass (concentration) of the protein in a suspension.

TABLE 2

List of measured and extracted parameters.

| Sample description | Light Intensity [a.u.] | Length of the Light Path [mm] | Mass of Protein Tested [µg] | $\Delta I_r$ per length [%/mm] |
|---|---|---|---|---|
| S1B | 21215 | 0.11111 | 1 | 104 |
| S1B + S2F | 21080 | 0.22222 | 1.0001 | 55 |
| S1B + S2E | 21265 | 0.33333 | 1.0011 | 34 |
| S1B + S2D | 21785 | 0.44444 | 1.0111 | 21 |
| S1B + S2C | 23440 | 0.55556 | 1.1111 | 4 |
| S1B + S2B | 23875 | 0.66667 | 2.1111 | 0.8 |

Figure 23A:
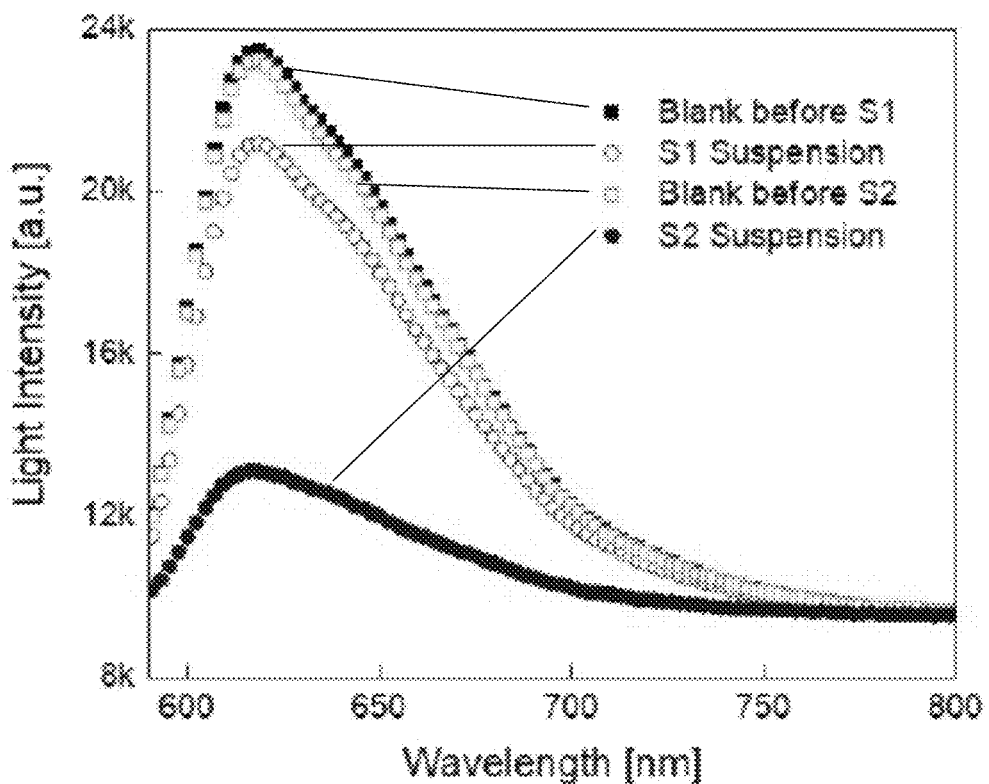
Figure 23B:
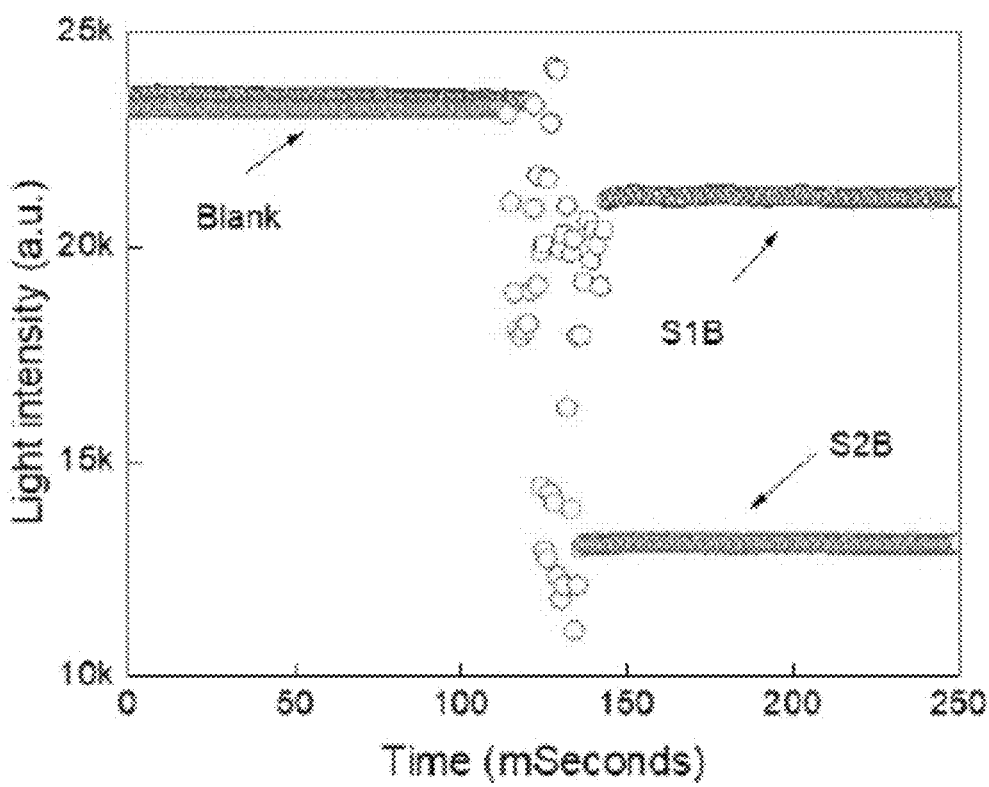
Figure 23C:
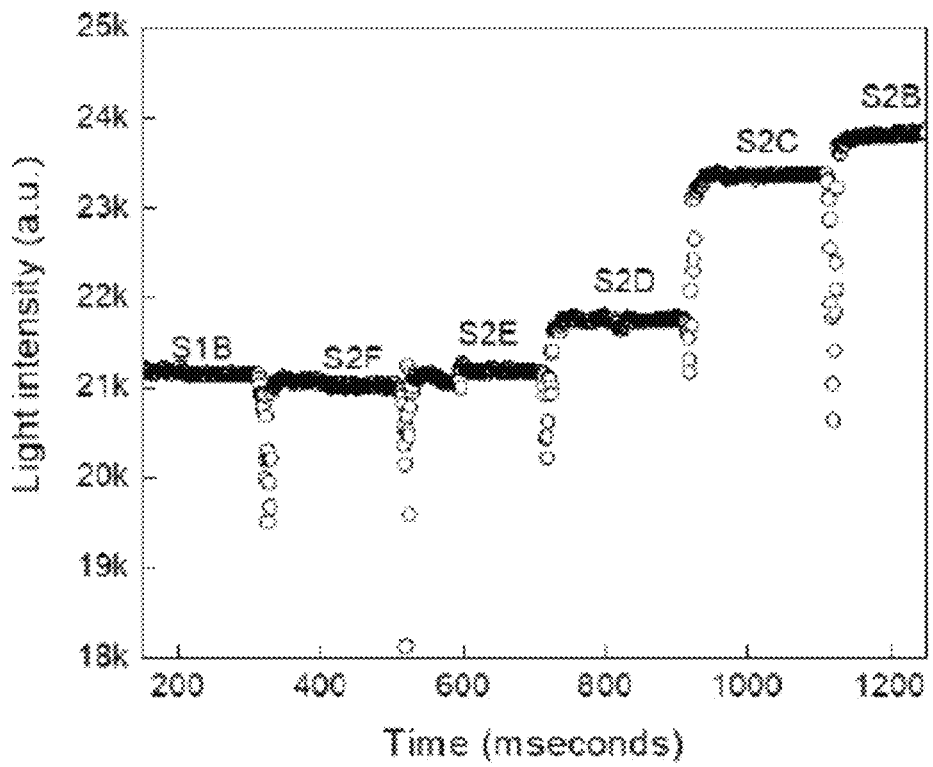
Figure 23D:
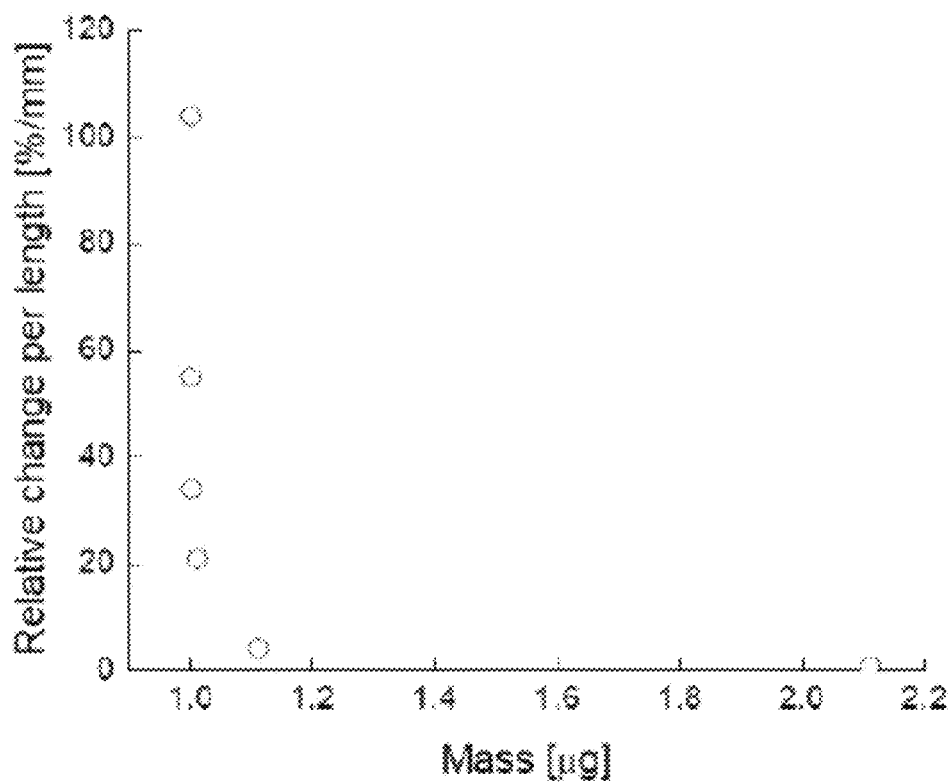
Figure 24C:
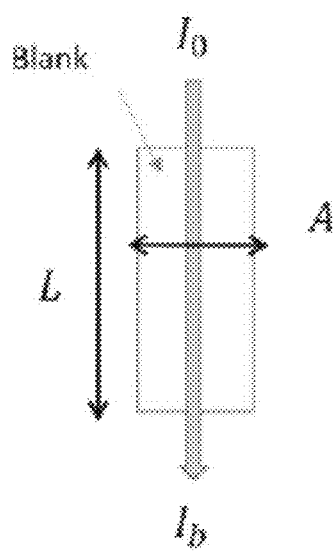
Figure 24C:
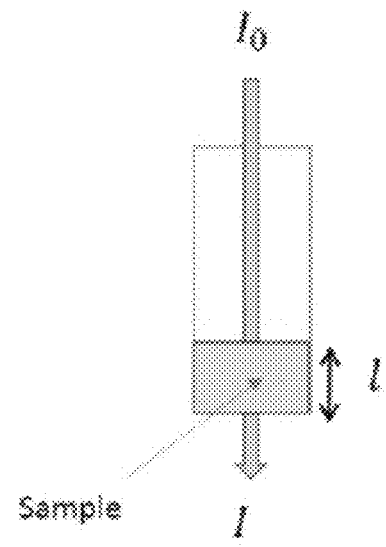
Figure 24C:
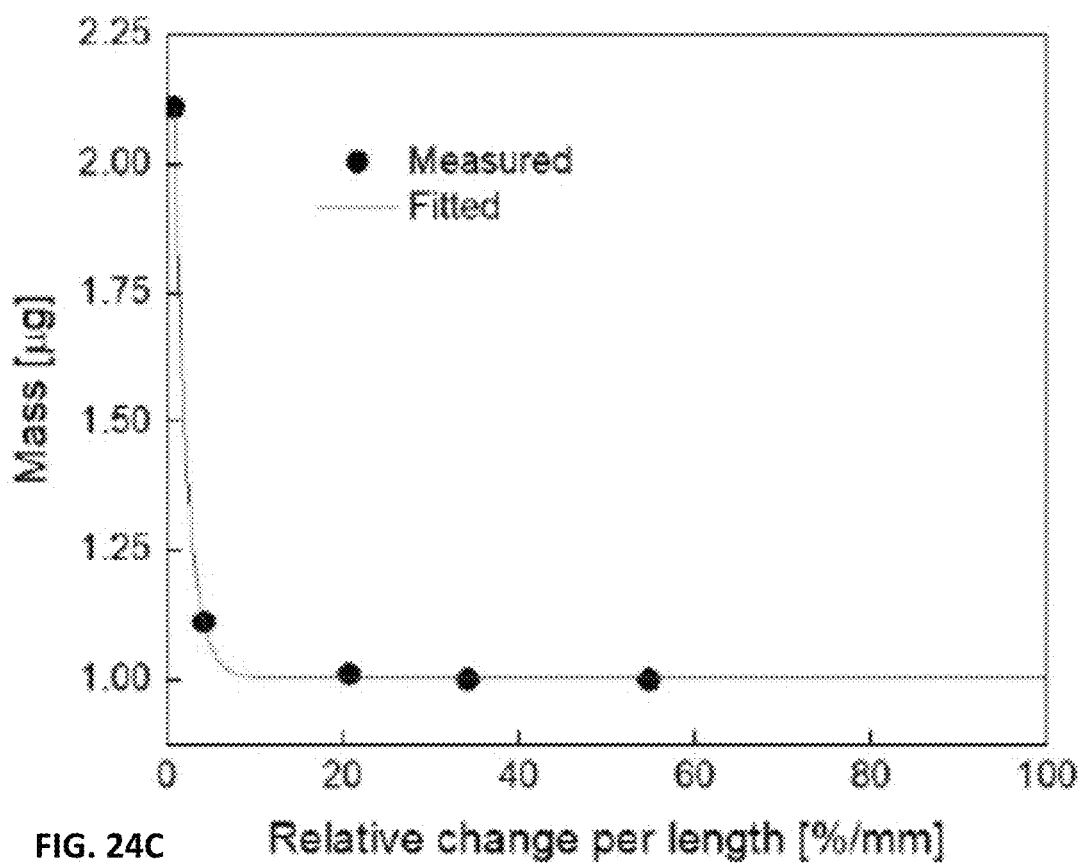

FIG. 23D shows the change in relative light intensity versus the total mass of the tested samples. As shown in Table 2, it indicates that as the mass of the protein increased in our experimental system, the intensity of light also increased, irrespective of the nature of the protein.

FIGS. 24A and 24B illustrate the definitions of the light intensities and light path length. The light source, for example a smart mobile integrated light source, emits a light intensity ($I_0$) that is the maximum intensity that can be measured in an experimental setup in accordance with the above embodiments. The blank intensity ($I_b$) is the measured intensity that goes through the empty container holding the sample such as the microcentrifuge tube used in the examples above. The instantaneous intensity (I) is the recorded light when it passes through the sample. This amount of light intensity strongly depends upon the buffer in which the sample is solubilized/dissolved in, its composition, the light path length, the kind of the suspended analytes and its size in the buffer. The light path length depends upon the loaded amount of suspension inside the container. The path length varies from zero up to the container length (L). For a sample with a specific volume (V), the corresponding path length is equal to the volume over the cross-sectional area of the container (A). Equation (1) expresses the relationship between the relative change in light intensity per light path length and loaded mass (m), as follows in equation (1):

$$m=m_i+m_f e^{-\alpha(\Delta I/l)} \quad (1)$$

In equation (1): $m_i$, $m_f$ and l are the initial mass of the buffer, the mass of the final suspension composite, and the light path length, respectively. α is the decay factor, unique for each control buffer. Its unit is in mm and could be correlated with the material absorptivity. ΔI is the relative changes in light intensity expressed as follows in equation (2):

$$\Delta I=(1-I/I_b)\times 100\% \quad (2)$$

In equation (2): I and $I_b$ are the instantaneous measured light intensity of the suspension and the corresponding blank, respectively. FIG. 24C shows the relationship between mass and the relative change per length after fitting the measured points with the exponential function. As can be seen, with more sample volume the path length increases and light intensity decreases, hence relative change decrease dramatically.

In method and system embodiments, relations for example those described herein, above and/or below, are applied to determine concentration of virus or virus load by serial dilution of antibody and simultaneous measurements using one or more microfluidic channels filled with a virus sample in solution. A microfluidic sensing device comprised in embodiments comprises one or more microfluidic channels. In the case with a plurality of microfluidic channels, the channels are in preferred embodiments arranged in parallel.

A light source may as in some embodiments integrated with the microfluidic sensing device, or the microfluidic sensing device may as in other embodiments be configured to receive light from an external light source. Both variant embodiments are configured such that light passes through the sample in each of the one or more microchannels, or groups of microchannels.

Embodiments of such microfluidic sensing devices further comprise an electric field device configured to apply an electric field over individual microchannels or groups of microchannels. Such an electrical field device may be integrated in the microstructure of the microfluidic device or be configured as a device external to the microstructure of the microfluidic device. The electrical field device may comprise electrodes and/or electrode connectors configured for individual channels, groups of channels or the whole microstructure.

Embodiments of such a microfluidic sensing device comprises a light sensor and/or an electrical sensor. Such sensors may be integrated in the said one or more channels or in the microstructure surrounding the channels, and said sensors are configured such that they can measure light and/or electrical parameters, e.g., scattering parameters, for each individual microchannel or groups of microchannels.

Mathematical models based on such said relations are used to extract a measurement value for the concentration of virus or virus load in the sample, thus reflecting the concentration of virus or virus load of test subject or patient from which the sample is taken. Quantification of the measurement value is for example carried out by means of calibration values e.g., represented in curves or tables. Such calibration values can for example be generated by calibrating parameter values determined in accordance with embodiments herein with known values for virus concentration or virus load. In embodiments, a quantification of concentration of virus concentration or virus load is determined from the differences of capacitance voltage profiles, and by processing a difference signal using semiconductor theory to extract single parameters or a collection of multiple parameters to determine said virus concentration or virus load.

Variants of these microfluidic channel embodiments, as with other embodiments herein, are configured to use for the detection of for SARS-CoV-2 diagnosis, whereas other variants are configured, dependent on selection of the antibody used, for detection of any respiratory virus such as influenza, respiratory syncytial virus (RSV), adenoviruses, or other coronaviruses like SARS and MERS.

Method embodiments for these purposes are configured such that: a said sample is placed and distributed in one or more microfluidic channels; measurement of said light scattering parameters and/or said electrical parameters is conducted for the sample content in each of said microfluidic channels; and virus concentration and/or virus load is determined based on said measured parameters.

In further variants of such embodiments said sample is diluted such that there is stepwise increasing dilution of antibody content in said one or more microfluidic channels and said measurement of parameters is conducted for said dilution steps.

In method embodiments said sample is placed and distributed in a plurality of parallel microfluidic channels; the antibody content is serially diluted in said plurality of parallel channels, simultaneously measuring said parameters in said plurality of channels; and said virus concentration and/or virus load is determined based on said measured parameters.

In further variants of the method the virus concentration and/or virus load is based on a mathematical relationship between said parameters and virus concentration and/or virus load, said mathematical relationship for example being calibrated against known virus concentration or virus load.

System embodiments for the above purposes, comprise: a microfluidic sensing device with one or more one or more microfluidic channels configured for placing and distributing a said sample in one or more of said microfluidic channels; one or more sensors configured for measurement of said light scattering parameters and/or said electrical parameters for the sample content in each of said microfluidic channels; and code portions, in said processing device, configured to determine virus concentration and/or virus load based on said measured parameters.

Further variants of system embodiments are configured for dilution of said sample such that there is stepwise increasing dilution of antibody content in said one or more microfluidic channels and said measurement of parameters is conducted for said dilution steps.

In further system embodiments: said microfluidic sensing device is configured with a plurality of parallel microfluidic channels for placing and distributing said sample; said microfluidic sensing device is configured for serially diluting the antibody content in said plurality of parallel channels, simultaneously measuring said parameters in said plurality of channels; and said system is configured to determine said virus concentration and/or virus load based on said measured parameters.

In some such system embodiments, said code portions are configured such that the virus concentration and/or virus load is based on a mathematical relationship between said parameters and virus concentration and/or virus load, said mathematical relationship for example being calibrated against known virus concentration or virus load.

These embodiments with microfluidic channels may be applied in conjunction with other embodiments described herein or independently.

Figure 25A:
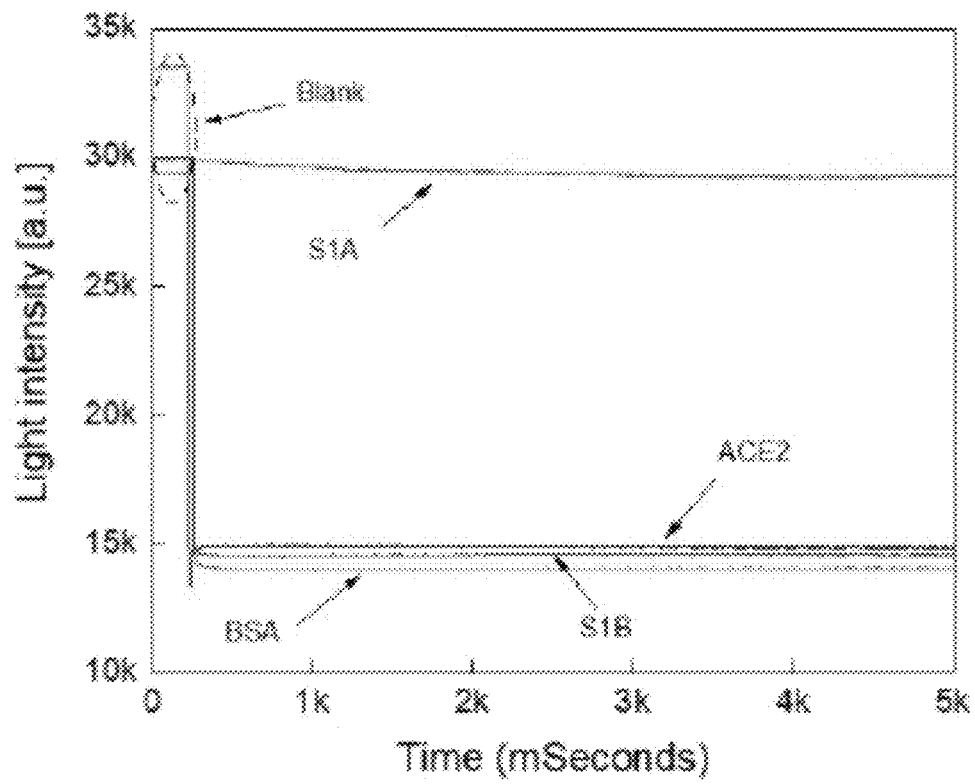
Figure 25B:
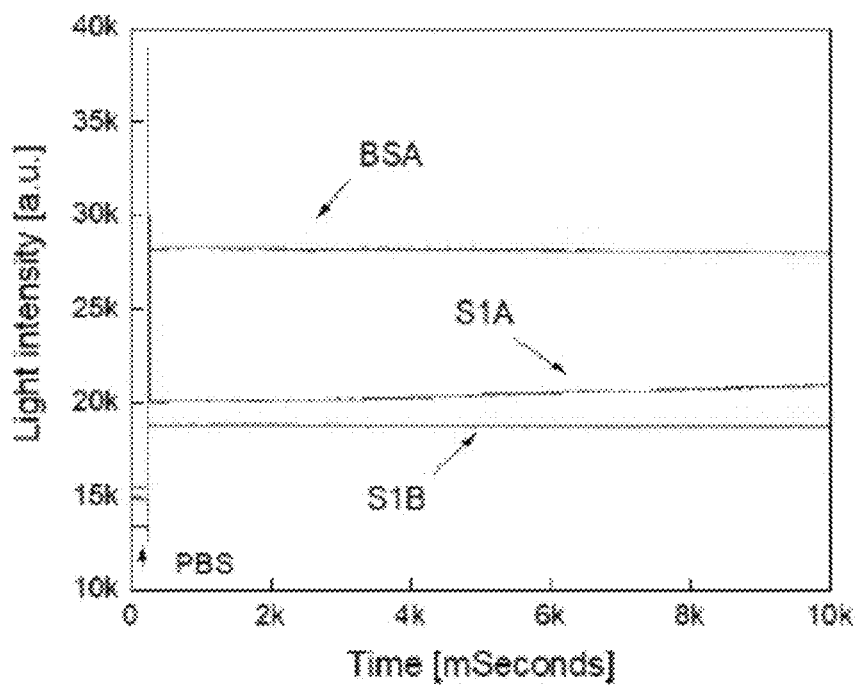
FIG. 25B shows the measured mixed light intensities versus time for ACE2 mixed with either S1A(S1X), or S1B(S1Y), or BSA.
Figure 25C:
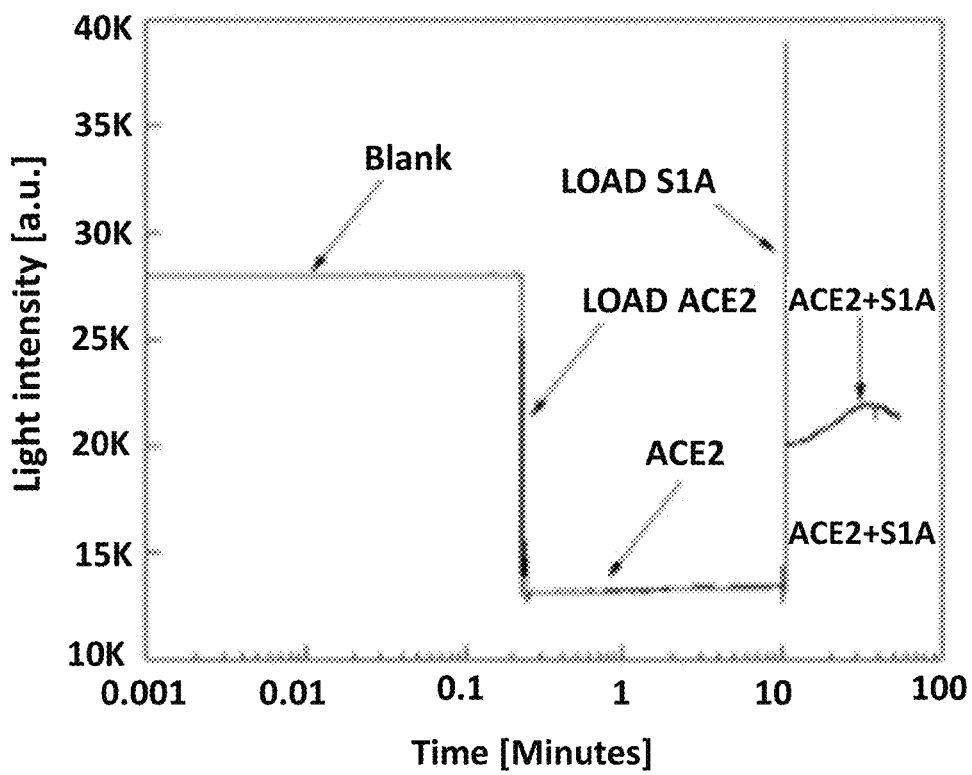
FIG. 25C shows the measured ACE2-S1A interaction profile for an extended time period.
Figure 25D:
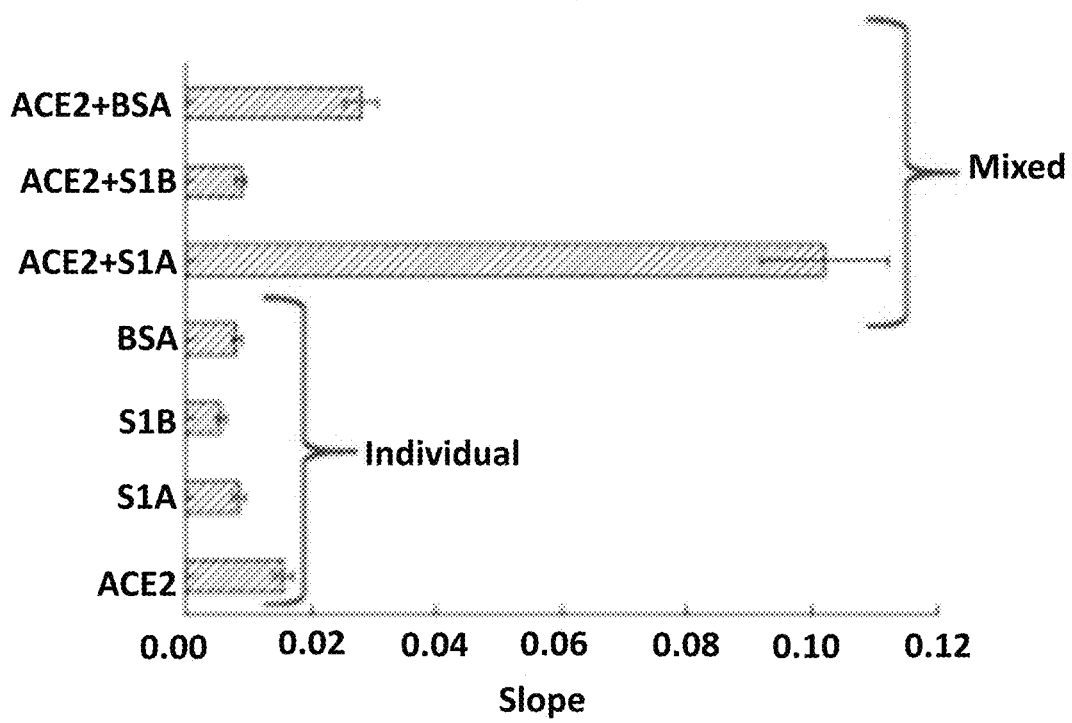
FIG. 25D shows extracted slopes for the individual and mixed protein suspensions.

Above it is described by means of exemplifying embodiments how to detect proteins in solution using light. Further, as in embodiments described herein, light intensity is used to characterize the binding interactions of the spike protein with the viral receptor ACE2. As an exemplifying demonstration of this mechanism, two different variants of the S1 subunit of the spike protein, S1A(S1X) and S1B(S1Y), were tested. One of these variants could bind ACE2 with a much stronger affinity than the other one. The S1 subunit of the spike protein S1A and S1B were tested along with a non-specific control protein, bovine serum albumin (BSA) that should not bind to ACE2. These proteins were selected to demonstrate the detection of the binding process with ACE2 over time. Examples of measurement results are shown in FIG. 25 with graphs of optical detection of binding interactions between ACE2 and other proteins. FIG. 25A shows measured light intensities over time for individual assessment of ACE2, S1A, S1B, and BSA. FIG. 25B shows the measured mixed light intensities versus time for ACE2 mixed with either S1A, or S1B, or BSA. FIG. 25C shows the measured ACE2-S1A interaction profile for an extended time period. FIG. 25D shows extracted slopes for the individual and mixed protein suspensions.

The measurement process in this example started with the blank, and after 200 seconds, 250 μL of ACE2 protein suspension was tested, as depicted in the graph of FIG. 25A. This process was repeated for S1A (S1X), S1B (S1Y), and BSA and their responses to light were measured individually in the same manner as ACE2.

The corresponding individual profiles of ACE2, S1A (S1X), S1B (S1Y) and BSA are depicted in FIG. 25A which showed a straight constant line over time. The responses of the various protein mixtures were read over a period of 15 minutes and are shown in FIG. 25B. This is interpreted to mean that there was no protein-protein interaction if the line was straight and constant, otherwise protein-protein interaction occurs.

To explore the interaction and binding characteristics, by example between ACE2 and S1A (S1X) in more detail, the measurement time between the two proteins was extended over one hour the results of which are plotted in FIG. 25C. As can be seen, a nice "hump" was observed as an increase in arbitrary units with time that was not observed in the other protein mixtures tested. The corresponding intensity of the interaction ($I_{ia}$) versus time (t) was fitted with a quartic polynomial as follows in equation (3):

$$I_{ia} = a + bt + ct^2 + dt^3 + et^4 \qquad (3)$$

In embodiments the following coefficients in equation (3) have the values: a, b, c, d and e are 20215.00393±6.54838, −0.15559±9.83118×10⁻⁴, 1.70666×10⁻⁵±5.093×10⁻⁸, −4.41996×10⁻¹⁰±1.09328×10⁻¹² and 3.46019×10⁻¹⁵± 8.30214×10⁻¹⁸, respectively. These coefficients can be used in embodiments to detect and identify the kind of analyte that binds with the ACE2 receptors. With other antigens and elements, the coefficients would have values characterised by the specific antigens or elements.

FIG. 25D shows the corresponding slopes that represent the change of the light intensities over time. Next, each protein was mixed with, in this example, the ACE2 antigen separately to detect any possible binding effect. The measurements started with first loading the ACE2 in the blank container, then after 200 ms, each protein was added to the ACE2. The ACE2+BSA and ACE2+S1B (S1Y) responses exhibited almost constant lines with corresponding responses shown in FIG. 25D, suggesting highly reduced or lack of any interaction as observed when the proteins were tested individually. However, the ACE2+S1A (S1X) profile showed a linear straight line with the maximum-recorded slope. The corresponding light intensity line increased over time, suggesting an interaction between the S1A (S1X) protein and the ACE2 receptor. It is noticeable that the slopes of the mixed proteins with ACE2 that did not exhibit much interaction, i.e., S1B (S1Y) and BSA, their slopes after mixing were less than the sum of their individual slopes. On the other hand, the ACE2+S1A (S1X) slope was higher than the sum of the individual ACE2 plus S1A (S1X) slopes, revealing a synergistic effect on light intensity. Based on these observations, our results suggest that the S1A (S1X) protein exhibits stronger interactions with ACE2, while BSA and S1B (S1Y) had weaker interactions with ACE2. These observations are confirmed by the fact that whereas S1A (S1X) has a higher affinity for ACE2 (for example 2 μg/mL S1A can bind 1.5-15 ng/mL ACE2), S1B (S1Y) reportedly has a much lower affinity (for example 2 μg/mL S1B binds 0.5-8.7 ng/mL ACE2), as tested in enzyme-linked immunosorbent assays (ELISA) by the company that synthesized these proteins (ProSci, USA).

Figure 26A:
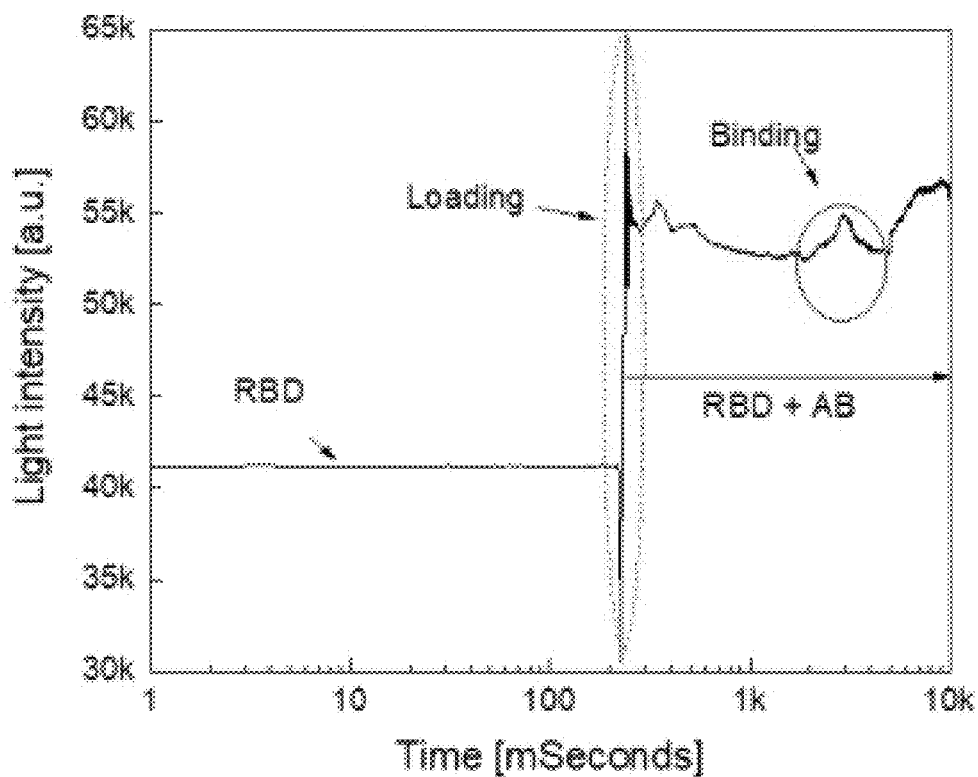
FIG. 26A shows the receptor binding domain (RBD) of the spike protein with its antibody (AB).

In further embodiments, the described optical system is used to detect protein-protein interactions. Using proteins that are well known to interact with each other in such measurements confirm the results described above. In an example, this can be done by testing the molecular interactions between an antigen and an antibody which is similar to the interaction between the spike protein and its receptor. In such an example, two proteins were tested along with their specific antibodies: the first protein was the receptor binding domain RBD of SARS-CoV-2 spike protein and its antibody and the other was the nucleocapsid protein NCP of SARS-CoV-2 and its antibody. Similar to the procedure described above, the two proteins were tested individually in an optical assay as described above followed by addition of their corresponding antibodies that were mixed and their interactions. FIG. 6 shows graphs of optical detection of the binding affinities between proteins and antibodies in this example. FIG. 26A shows the binding between the receptor binding domain RBD, in this example, of SARS-CoV-2 spike protein and its antibody AB. Upon the addition of the antibody, marked Loading in FIG. 26A an interaction peak was recorded as indicated with a circle FIG. 26A.

Figure 26B:
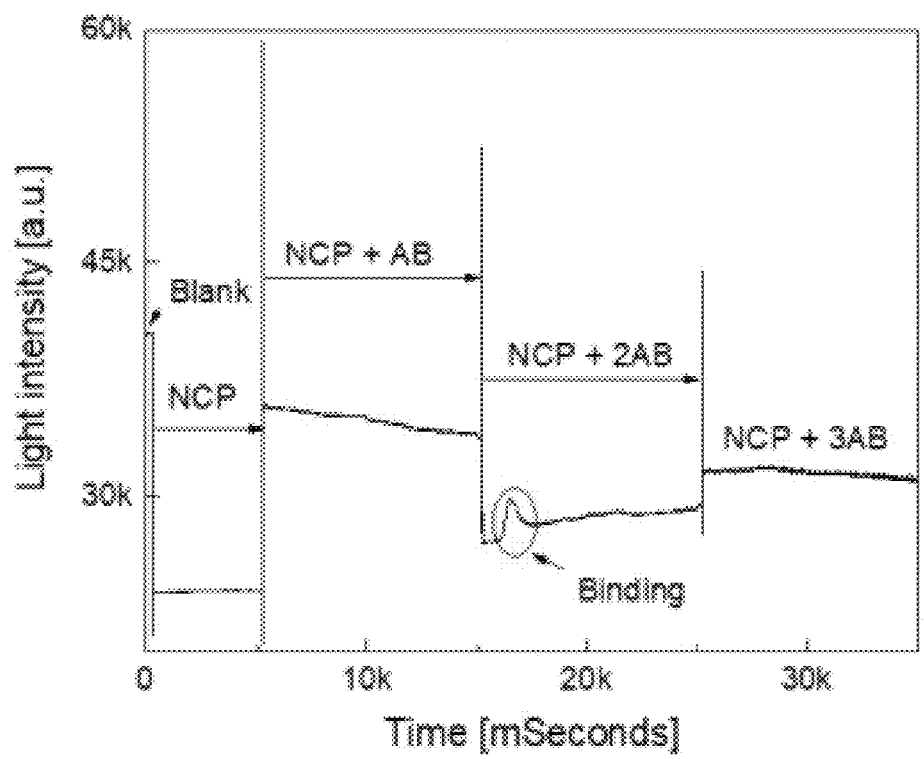
FIG. 26B shows the nucleocapsid protein (NCP) and its antibody.

FIG. 26B shows the binding between, in this example, the nucleocapsid protein NCP of SARS-CoV-2 and its antibody AB. As indicated in the graph, the measurement started with a blank, then with added NCP and after that with added antibody NCP+AB three times, indicated NCP+AB, NCP+2AB and NCP+3AB, respectively. The antibody was added a second time to NCP since no binding interaction was observed the first time. After the second addition of antibodies 2AB a peak in the light intensity indicating binding activity was observed, as indicated with a circle in FIG. 26B. To further confirm the result, the antibody was added a third time NCP+3AB, and this time once again, the binding interaction was not apparent. In this exemplifying case, the conclusion is that the binding effect occurred at specific antibody concentration. For a virus-based suspension, embodiments therefore use a fixed antibody concentration and serially dilute the virus suspensions and conduct the binding measurements. At a specific virus concentration, binding effect will appear on the optical response.

Figure 26C:
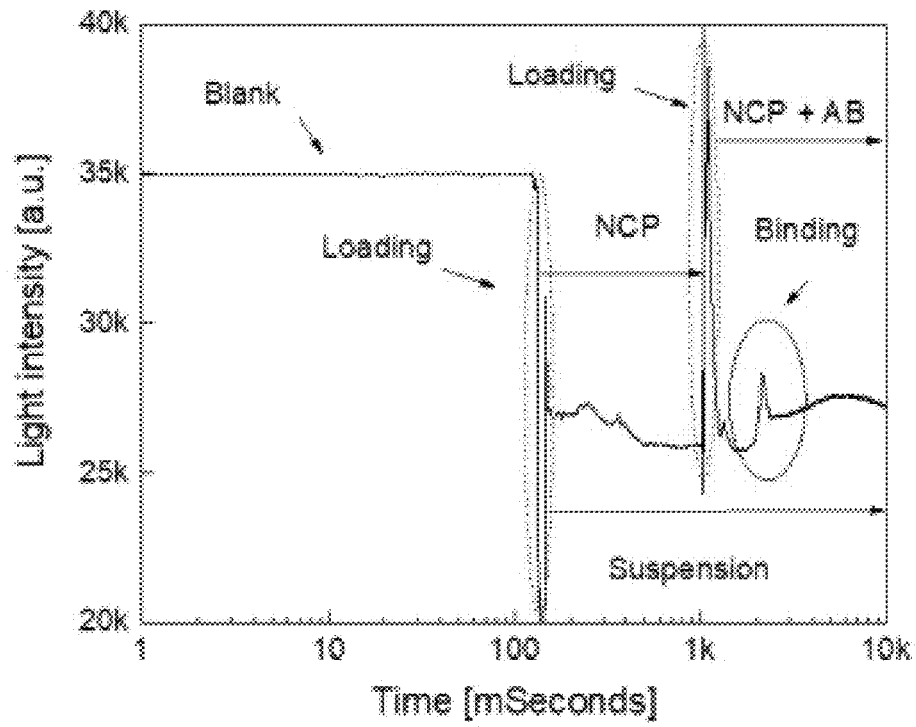
FIG. 26C shows NCP binding with the antibody after mixing inside.
Figure 26D:
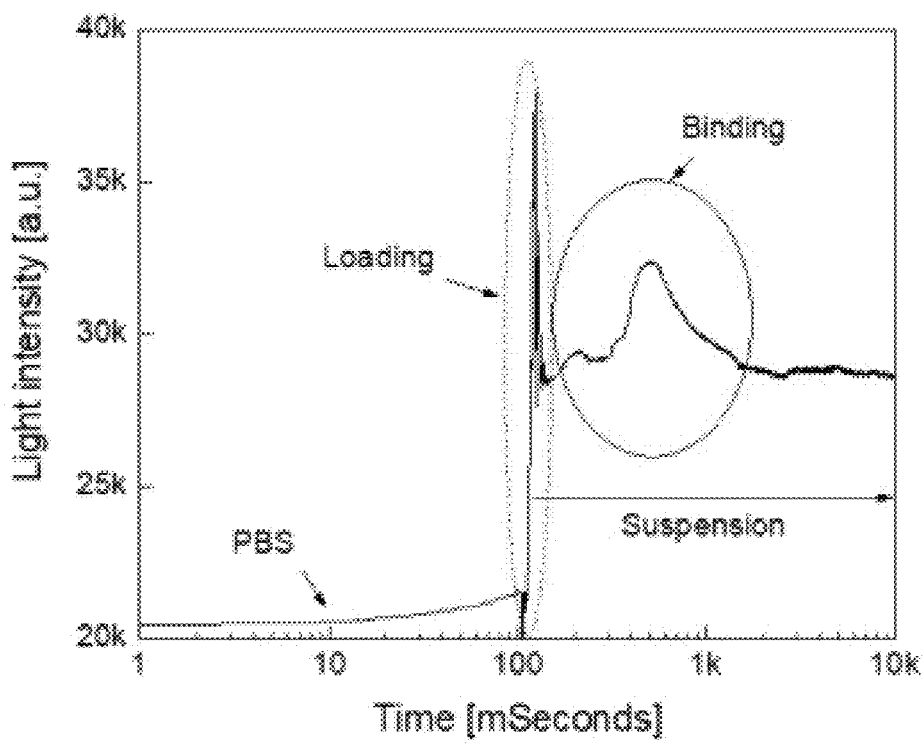

FIGS. 26C and 26D illustrate the corresponding optical responses for, in this example, NC protein and its corresponding antibody when they were mixed either inside (FIG. 26C) or outside (FIG. 26D) the microcentrifuge tube, respectively. Peaks, or humps, in the light intensity indicating binding activities are marked with circles in the graphs. Inside mixing means that the protein was added to the tube and the antibody was added after 100 seconds, while in the outside mixing scenario, both the protein and antibody were mixed prior to being loaded in the tube for optical measurements. As can be seen, the binding response could be detected in each case in the form of the appearance of the hump. However, this "hump" was a lot more pronounced when the protein and the antibody were mixed prior to test testing than when they were added sequentially. When employing embodiments in real life scenarios with patient samples, the antibody should be already bound to the viral or bacterial antigen at the time of detection. Preferably a potentially virus containing sample from a patient should be mixed with antibody before optical detection measurement.

Figure 27A:
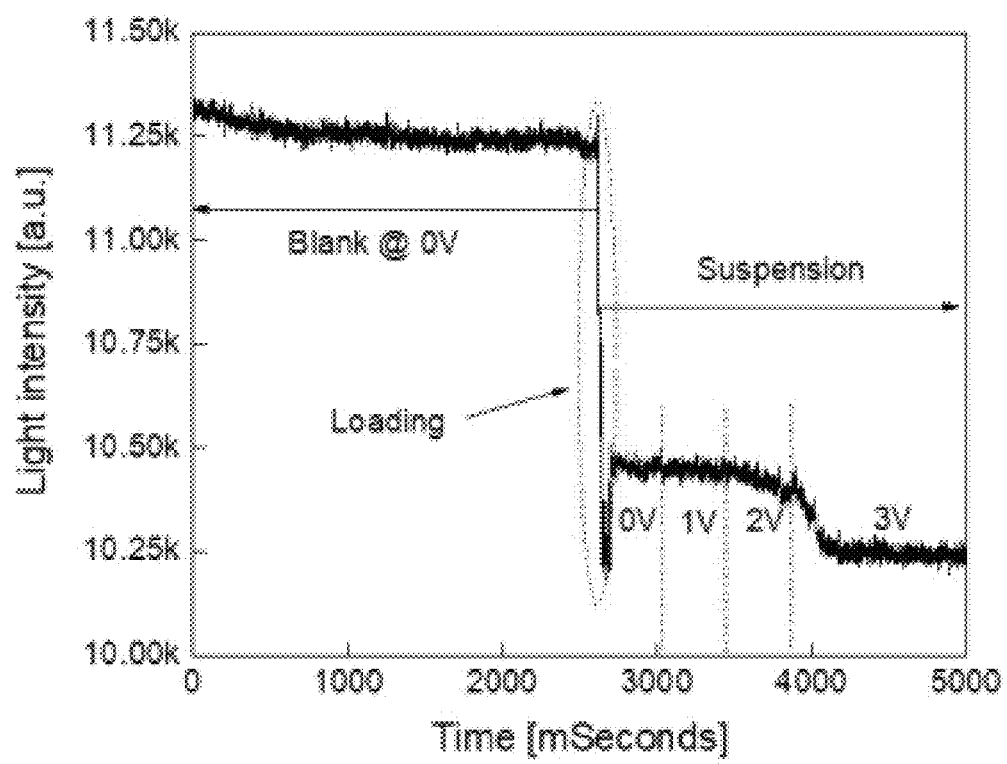

Embodiments makes use of the effect of direct current DC biasing on the ability of two proteins to bind specifically. An example to illustrate this was carried out by subjecting the nucleocapsid protein (NCP or NC protein) solution to DC voltage bias. FIG. 7 shows graphs of Opto-electrical measurements of nucleocapsid protein (NC protein) with direct current DC biasing. FIG. 27A shows an example of measured NC protein optical response versus time at different DC bias voltages. An applied bias should result in an induction of current across the suspension. If this current is high enough, it should have the potential to destroy the protein physiology and functionality, resulting in the loss of specific protein-protein interactions. In this example, the NC protein solution was loaded in an electroporation cuvette (rather than a microcentrifuge tube as in previous examples) that incorporates two electrodes with a volume of 0.5 mL and a separation distance of 0.4 cm. This should result in a breakdown electric field of 7.5V/cm. At this field onwards, the binding between the protein and the antibody should be affected. Above this field the sample will be incapacitated. As shown in FIG. 27A, the optical response decays slowly with the application of DC bias. At 3 volts DC bias, the optical response decays with a considerable step, and increasing the DC bias further should burn the suspension and destroy it.

Figure 27B:
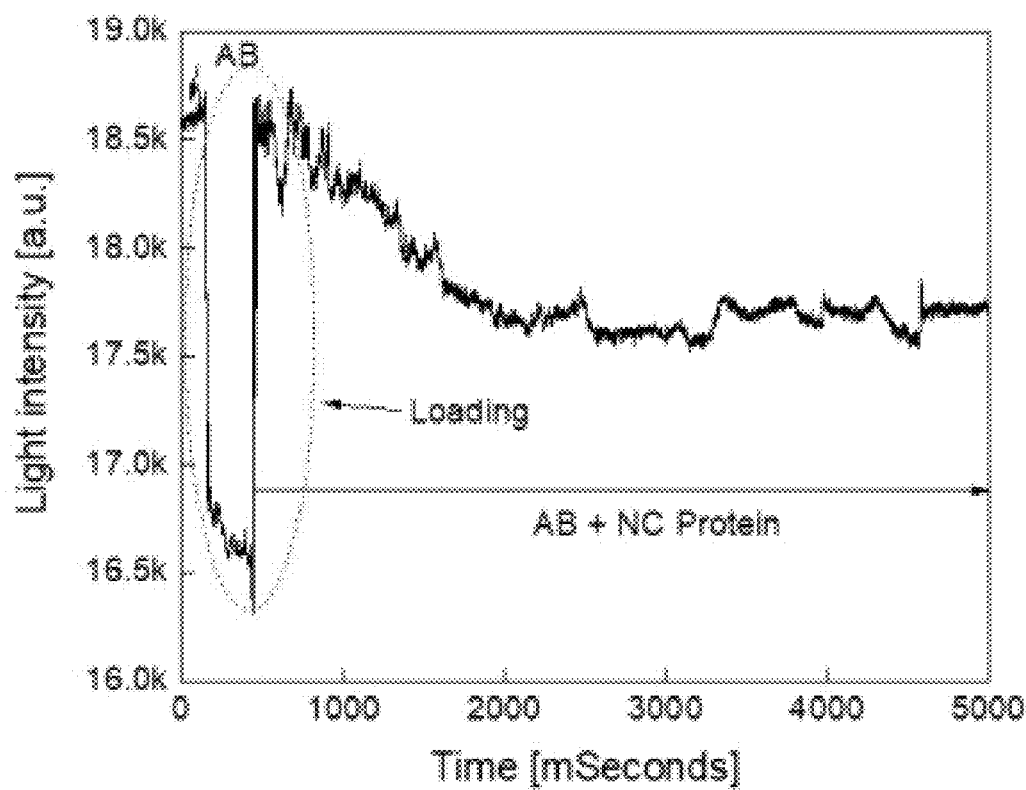

The breakdown field depends on the electrical characteristics of both the buffer and the analyte such as proteins, viruses, etc. In further exemplifying application of embodiments, the suspension of protein was subjected to 3 V for 1 minute and then the antibody to nucleocapsid NC was added to the NC protein solution. The corresponding measured response is shown in FIG. 27B. The measured response was observed to be noisy and did not show a clear binding effect when compared with FIG. 26C that shows the optical response for the same protein and antibody without the application of DC bias. Embodiments are configured to create a corresponding vaccine for a disease by subjecting its corresponding virus to DC bias which will affect its infectivity and destroy its physiology and communicability. Furthermore, embodiments of the optical detection in time domain are configured to be used for monitoring and detecting the efficiency of vaccine process development.

Embodiments are configured for virus detection on samples on paperbased nitrocellulose membrane. The nitrocellulose membrane is a popular matrix that is frequently used due to its high protein-binding affinity with a pore size of 0.25-0.45 μm in paper-based diagnostics. Protein molecules usually bind to the nitrocellulose membranes through hydrophobic interactions. Due to the ease of their handling, cheap cost, and the presence of hydrophobic interactions between them and the suspended proteins, we tested whether the binding between the SARS-CoV-2 spike protein and antibody could be detected optically when both were added to each other on the nitrocellulose membrane. Using embodiments illustrated with the experimental setup described in FIG. 20, the optical responses for nitrocellulose membrane, nitrocellulose membrane and spike protein alone, nitrocellulose membrane and antibody against spike protein alone, and nitrocellulose membrane spike protein-antibody were measured in illustrating example. FIG. 8 shows graphs of this illustrating example of protein-protein interaction measurements on paperbased nitrocellulose membrane (NM).

Figure 28A:
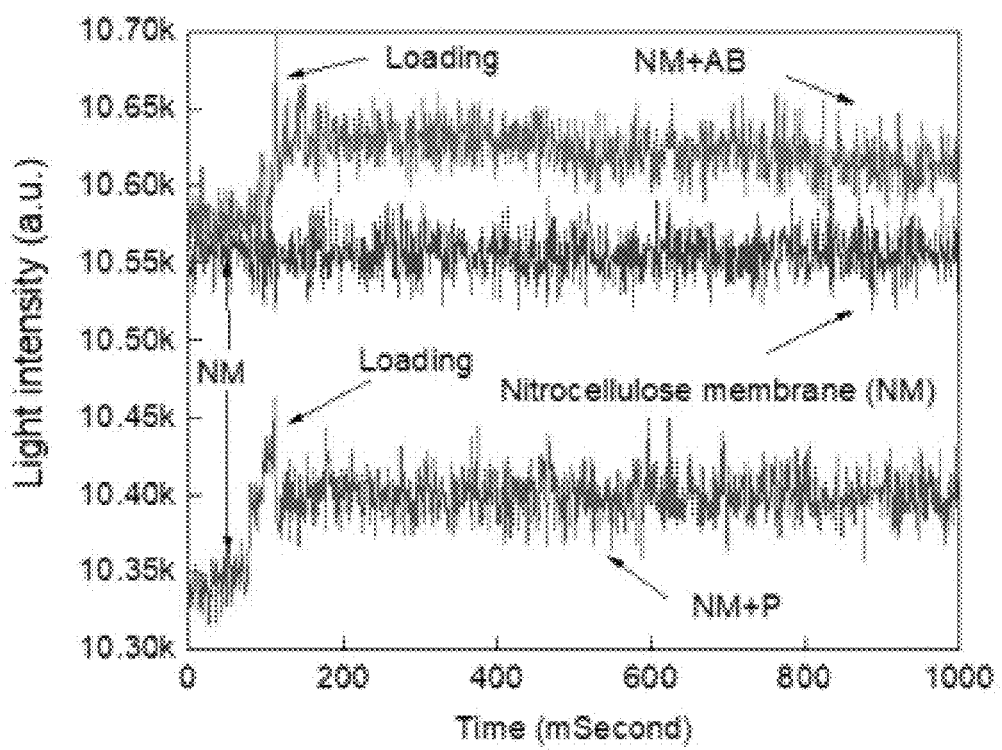
Figure 28B:
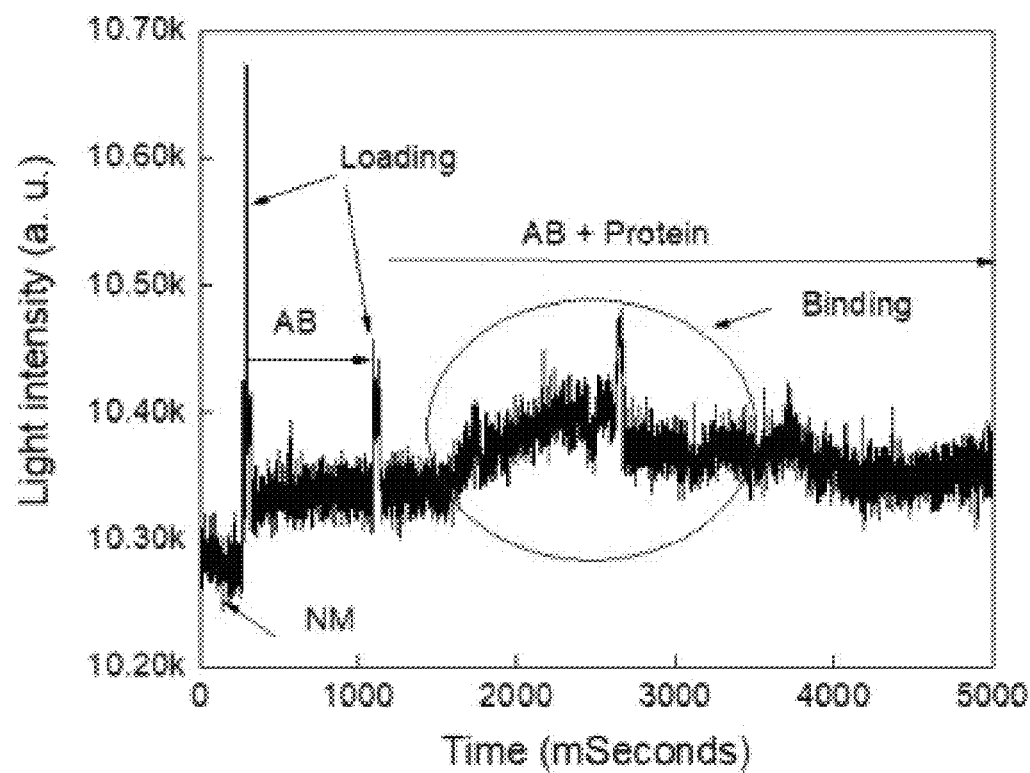

FIG. 28A shows optical responses on nitrocellulose membrane (NM) alone, nitrocellulose membrane and spike protein (NM+P), and nitrocellulose membrane and antibody to spike protein (NM+AB) alone. The graph in FIG. 28A shows that both the antibody alone and spike protein alone exhibited higher light intensity than the nitrocellulose membrane alone with almost a straight line with constant slope over a time period of 10 seconds. The on-paper measured optical responses exhibited fluctuations as in the samples measured using microcentrifuge tubes. This implies that these fluctuations are not due to any kind of interactions, but instead are due to the spectrometer conversion process. FIG. 28B summaries the interaction measurements which start with the membraneNM. After 100 mSecond, the antibody suspension AB was loaded on the membrane and measurements were conducted up to 1000 mSecond. Next, the spike protein sample was loaded AB+Protein and measurements were continued up to 5000 mSecond. As shown in FIG. 28B, the interaction peaks appeared clearly within the indicating circle. It is worth noting that the membrane size, shape, and charge of biomolecules, pH and viscosity of the control buffer, as well as the composition influences the corresponding optical response and binding interactions.

Figure 29:
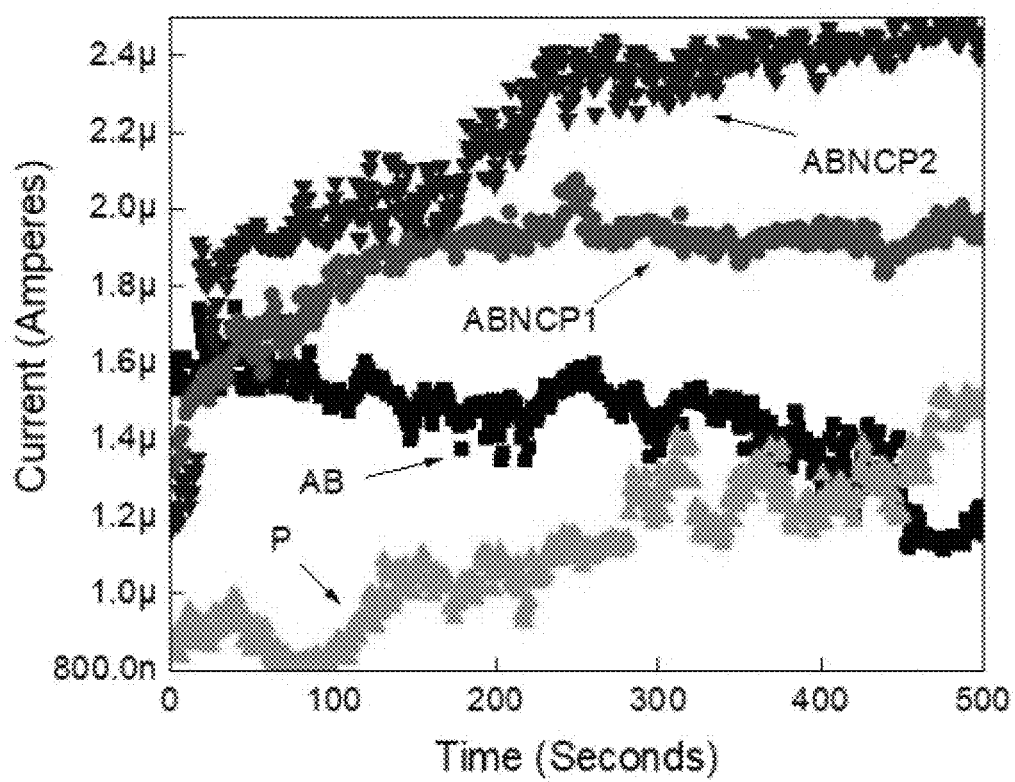
FIG. 29 shows a graph of chronoamperometry measurements indicating current versus time for different sample suspensions, in accordance with embodiments.

As these illustrating protein-antibody interactions took place within a time domain, the measurements are further illustrated using the well-known technique of chronoamperometry to detect this interaction electrically. Chronoamperometry is an electrochemical technique in which an electric potential is applied between two electrodes to measure the resulting current at the surface that is created from faradaic processes over time. The corresponding chronoamperometry measurements were conducted accordingly as plotted in FIG. 29. FIG. 29 thus shows a graph of chronoamperometry measurements indicating current versus time for different sample suspensions, in accordance with embodiments. In FIG. 29, the lowest curve shows protein P (NCP), the second lowest curve shows antibody AB, whereas the next to upper curve shows a first measurement on protein-antibody suspension ABNCP1 and the uppermost curve shows a second measurement on protein-antibody suspension ABNCP2. The two curves ABNCP1 and ABNCP2 pertain to two different measurements that uses the same nucleoprotein and the same antibody.

The applied potential in this example was of 0.5 mVolts, the minimum voltage that can be applied without causing any harm to the protein and antibody; therefore, it should not have affected the interaction process. As shown in FIG. 29, the electrical current measurements for the protein-antibody suspensions ABNCP1 and ABNCP2 exhibited exponential growth profiles, whereas the individual profiles for protein P (NCP) and antibody AB did not exhibit such behaviour. These embodiments can be used in a detection strategy. As shown in FIG. 29, the binding took place between 50 and 250 seconds, a period during which protein-antibody solutions ABNCP1 and ABNCP2 (ABP) exhibited higher measured electrical current values compared with protein P or antibody AB currents alone.

As described and illustrated in the above examples, different embodiments are configured as follows.

Specific examples of device and method have been described herein for purposes of illustration. These are only examples. The technology provided herein can be applied to device and method other than the examples described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

What is claimed is:

1. A method of detecting, identifying and quantifying an analyte in a specimen comprising one or more cells, the specimen being accommodated in a suspension medium, comprising:
   apportioning the suspended specimen into one or more test samples;
   adding a reagent to the one or more test samples, said reagent being prone to engage in a binding activity with an analyte present in a said one or more cells;
   applying an electric field with a first magnitude and with a second magnitude over said one or more test samples for a selected period of time, said second magnitude being higher than said first magnitude, thereby increasing the cell permeability due to pore formation in the cell membrane and allowing the reagent to penetrate the cell membrane through the formed pores and bind with the analyte;
   measuring one or more electrical properties of said one or more test samples in response to said applied electric field for said first magnitude and for said second magnitude over said period of time;
   identifying characteristics of said electrical properties responses;
   determining the presence, the identification and/or the quantity of the analyte based on the characteristics of said electrical properties responses to said first magnitude and to said second magnitude of the applied electric field,
   wherein the reagent is in the form of ACE2 antibodies, NC antibodies, anti-N antibodies, or a fluorescence based reagent; and
   wherein the analyte is SARS-CoV-2.

2. The method of claim 1, wherein said determining of the presence, the identification and/or the quantity of the analyte in addition or alternatively is based on differences in the characteristics of said electrical properties responses to said first and second magnitude applied electric field.

3. The method of claim 1, further comprising:
   measuring optical properties responses of said one or more test samples in response to said applied electric of said first and second magnitudes; and
   determining the presence, the identification and/or the quantity of the analyte based on the characteristics or on the differences in characteristics of said optical properties responses to said first magnitude and to said second magnitude of the applied electric field.

4. The method of claim 1, wherein when the reagent is added quantification of the analyte is determined by detecting and estimating a count of binding events occurring between analyte and reagent as indicated in the electrical properties response characteristics after an electric field has been applied over the test sample.

5. The method of claim 1, wherein detection of the analyte is determined based on non-linearities found in the electrical properties response characteristics after an electric field has been applied over the test sample.

6. The method of claim 1, wherein identification of the analyte is determined based on a detected occurrence and/or pattern of non-linearities in the electrical properties response characteristics after an electric field has been applied over the test sample.

7. The method of claim 1, wherein the applied electric field is induced by applying a DC voltage or a pulsating AC voltage over said one or more test samples.

8. The method of claim 1, comprising:
   apportioning the suspended specimen into a first, a second and a third test sample;
   arranging said first test sample to contain purely the suspended specimen;
   adding a reagent in the form of ACE2 antibodies to said second test sample;
   adding a reagent in the form of NC antibodies to said third test sample;
   applying an electric field with a first magnitude and with a second magnitude over said first, second and third test samples for a selected period of time, said second magnitude being higher than said first magnitude;
   measuring one or more electrical properties of said test samples in response to said applied electric field for said first magnitude and for said second magnitude over said period of time;
   identifying characteristics of said electrical properties responses;
   determining the presence, the identification and/or the quantity of the analyte dependent on the characteristics and/or on differences in the characteristics of said electrical properties responses to said first magnitude and to said second magnitude of the applied electric field.

9. The method of claim 1, comprising providing two or more test samples with specimen and an added reagent, and for said two or more test samples, simultaneously:
   measuring electrical properties responses for an applied low magnitude electric field over said test samples;
   measuring electrical properties responses for an applied high magnitude electric field over said test samples;
   analyze characteristics of said electrical properties responses for said two or more test samples;
thereby processing two or more test samples in parallel for increased efficiency;
said electrical properties responses being capacitance versus applied voltage responses.

10. The method of claim 9, further comprising measuring optical properties responses of said two or more test samples for said applied low and high magnitude electric fields.

11. The method of claim 1, comprising:
   providing a first set of two or more test samples with specimen and a second set of test samples with specimen and added reagent;
   for one or more first pair of test samples with specimen and test samples with specimen and added reagent, measuring electrical properties responses for an applied low magnitude electric field over said first pairs of test samples;
   for one or more second pairs of test samples with specimen and test samples with specimen and added reagent, measuring electrical properties responses for an applied high magnitude electric field over said second pairs of test samples;
   analyze characteristics of electrical properties responses for said one or more first pairs and for said one or more second pairs of test samples;
   optionally, comprising measuring optical properties responses of said one or more first pairs and of said one or more second pairs of test samples for said applied low and high magnitude electric fields;
thereby processing multiple test samples in parallel for increased efficiency;
said electrical properties responses being capacitance versus applied voltage responses.

* * * * *